(12) United States Patent
Rüter et al.

(10) Patent No.: US 8,840,901 B2
(45) Date of Patent: Sep. 23, 2014

(54) YOPM AS DELIVERY VEHICLE FOR CARGO MOLECULES AND AS BIOLOGICAL THERAPEUTIC FOR IMMUNOMODULATION OF INFLAMMATORY REACTIONS

(75) Inventors: Christian Rüter, Münster (DE); Gerhard Heusipp, Havixbeck (DE); Alexander M. Schmidt, Havixbeck (DE)

(73) Assignee: Universitaetsklinikum Muenster, Muenster (DE)

( * ) Notice: Subject to any disclaimer, the term of this patent is extended or adjusted under 35 U.S.C. 154(b) by 638 days.

(21) Appl. No.: 12/933,062

(22) PCT Filed: Mar. 17, 2009

(86) PCT No.: PCT/EP2009/053159
§ 371 (c)(1),
(2), (4) Date: Sep. 16, 2010

(87) PCT Pub. No.: WO2009/115531
PCT Pub. Date: Sep. 24, 2009

(65) Prior Publication Data
US 2011/0183908 A1      Jul. 28, 2011

(30) Foreign Application Priority Data

Mar. 17, 2008  (EP) .................... 08004967

(51) Int. Cl.
*A61K 39/02*       (2006.01)
(52) U.S. Cl.
USPC ....................................... 424/190.1
(58) Field of Classification Search
None
See application file for complete search history.

(56) References Cited

U.S. PATENT DOCUMENTS 6,602,506 B1 *   8/2003   van der Bruggen et al. ........................ 424/200.1

FOREIGN PATENT DOCUMENTS

WO      WO 9952563 A1 * 10/1999 ............. A61K 48/00

OTHER PUBLICATIONS

Goldberg et al. *Yersinia pestis* Cytokine YopM 2006.*
PCT Search Report for International Application No. PCT/EP2009/053159 mailed on Feb. 16, 2010.
Skrzypek E., et al. (1998) *Targeting of the Yersinia pestis YopM protein into HeLa cells and intracellular trafficking to the nucleus.* Molecular Microbiology 30: 1051-1065.
Trülzsch K., et al. (2004) *Contribution of the Major Secreted Yops of Yersinia enterocolitica 0:8 to Pathogenicity in the Mouse Infection Model.* Infection and Immunity, 72: 5227-5234.
Viboud G., et al. (2005) *Yersinia Outer Proteins: Role in Modulation of Host Cell Signaling Responses and Pathogenesis.* Annu. Rev. Microbiol. 59: 69-89.
Skrzypek E., et al. (2003) *Application of a Saccharomyces cerevisiae Model to Study Requirements for Trafficking of Yersinia pestis YopM in Eucaryotic Cells.* Infection and Immunity, 71: 937-947.
Skrzypek E., et al. (2001) *Structure-Function Analysis of YopM of Yersinia pestis: Identification of the Region of YopM Necessary for its Delivery to the Cell Nucleus.* ASM 101$^{st}$ General Meeting Abstracts, p. 300, Abstract D-116.
Benabdillah R., et al. (2004) *Identification of a nuclear targeting signal in YopM from Yersinia spp.* Microbial Pathogenesis, 36: 247-261.
Anisimov A., et al. (2006) *Treatment of plague: promising alternatives to antibiotics*, Journal of Medical Microbiology, 55: 1461-1475.
Kerschen E., et al. (2004) *The Plague Virulence Protein YopM Targets the Innate Immune Response by Causing a Global Depletion of NK Cells.* Infection and Immunity, 72: 4589-4602.
Heusipp G., et al. (2006) *YopM of Yersinia enterocolitica specifically interacts with a1-antirypsin without affecting the anti protease activity.* Microbiology, 152: 1327-1335.
Trülzch K., et al. (2003) *B-431 Differential Attenuation of Yersinia enterocilitica 0:8 Yop Mutants in the Oral C56BL/6 Mouse Model of Infection.* ASM 103$^{rd}$ General Meeting Abstracts, Abstract B-434.
Monnazzi L.G.S., et al. (2004) *Influence of Yersinia pseudotuberculosis outer proteins (Yops) on interleukin-12, tumor necrosis factor alpha and nitric oxide production by peritoneal marcophages.* Immunology Letters, 94: 91-98.
Evdokimov A., et al. (2001) *Unusual Moleular Architecture of the Yersinia pestis Cytotoxin YopM:A Leucine-rich Repeat Protein with the Shortest Repeating Unit*, J. Mol. Biol., 312: 807-821.
McDonald C., et al. (2003) *The Yersinia Virulence Factor YopM Forms a Novel Protein Complex with Two Cellular Kinases.* Journal of Biological Chemistry, 278: 18514-18523.
Sauvonnett N., et al. (2002) *Regulation of mRNA Expression in Macrophages after Yersinia entercolitica Infection.* Journal of Biological Chemistry, 277: 25133-25142.
Boland, A., et al., (1996) *Status of YopM and YopN in the Yersinia Yop virulon: YopM of Y.enterocolitica is internalized inside the cytosol of PU5-1.8 macrophages by the YopB, D, N delivery apparatus*, The EMBO Journal 15: 5191-5201.

* cited by examiner

*Primary Examiner* — Gary B. Nickol
*Assistant Examiner* — Khatol Shahnan-Shah
(74) *Attorney, Agent, or Firm* — Kagan Binder, PLLC

(57) ABSTRACT

The present invention relates to the use of *Yersinia* outer protein M (YopM), a YopM fragment, or a YopM variant, which is capable of autopenetrating the cell membrane and of integrating into the cell cytosol without the requirement of additional factors for delivering a cargo molecule across the membrane to the cytosol of a cell. The present invention also relates to a pharmaceutical composition comprising YopM, a YopM fragment, or a YopM variant being capable of autopenetrating the cell membrane and of integrating into the cell cytosol without the requirement of additional factors for the regulation of inflammatory reactions of the immune system and the treatment of diseases caused by autoimmunity of the host. The present invention further relates to a YopM fragment or variant, which is capable of autopenetrating the cell membrane and of integrating into the cell cytosol without the requirements of additional factors as well as such proteins or YopM linked to a cargo molecule.

16 Claims, 19 Drawing Sheets

Figure 1:
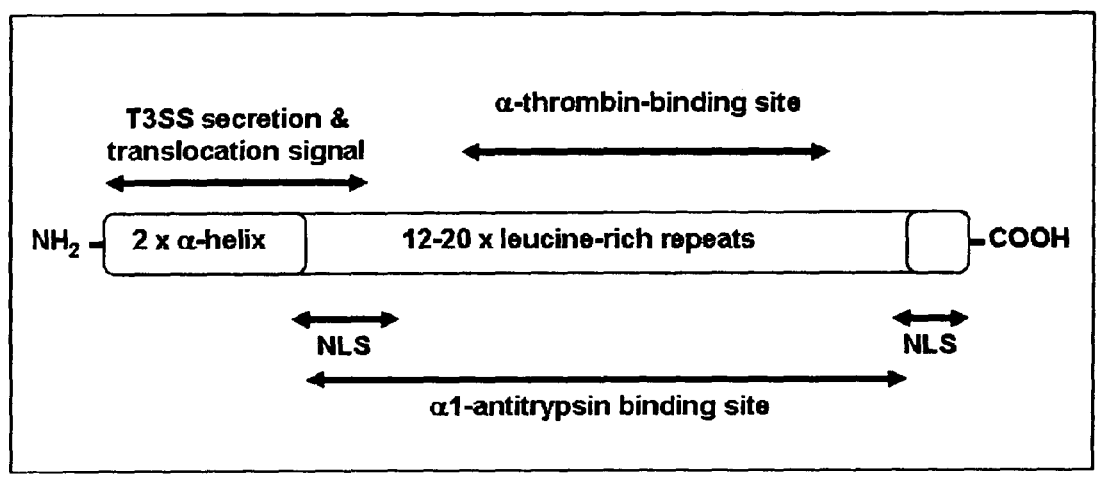

```
                        SEQUENCE LISTING

<160> NUMBER OF SEQ ID NOS: 8

<210> SEQ ID NO 1
<211> LENGTH: 550
<212> TYPE: PRT
<213> ORGANISM: Yersinia enterocolitica
<220> FEATURE:
<221> NAME/KEY: MISC_FEATURE
<223> OTHER INFORMATION: strain IP 32953

<400> SEQUENCE: 1

Met Tyr Gly Phe Val Cys Ser Glu Lys Leu Asp Asn Lys Asn Ile Phe
1               5                   10                  15

Arg Lys Ala Phe Asn Met Phe Ile Asn Pro Arg Asn Val Ser Asn Thr
            20                  25                  30

Phe Leu Gln Glu Pro Leu Arg His Ser Ser Asn Leu Thr Glu Met Pro
        35                  40                  45

Val Glu Ala Glu Asn Val Lys Ser Lys Thr Glu Tyr Tyr Asn Ala Trp
    50                  55                  60

Ser Glu Trp Glu Arg Asn Ala Pro Pro Gly Asn Gly Glu Gln Arg Glu
65                  70                  75                  80

Met Ala Val Ser Arg Leu Arg Asp Cys Leu Asp Arg Gln Ala His Glu
                85                  90                  95

Leu Glu Leu Asn Asn Leu Gly Leu Ser Ser Leu Pro Glu Leu Pro Pro
            100                 105                 110

His Leu Glu Ser Leu Val Ala Ser Cys Asn Ser Leu Thr Glu Leu Pro
        115                 120                 125

Glu Leu Pro Gln Ser Leu Lys Ser Leu Gln Val Glu Asn Asn Asn Leu
    130                 135                 140

Lys Ala Leu Pro Asp Leu Pro Pro Ser Leu Lys Lys Leu His Val Arg
145                 150                 155                 160

Glu Asn Asp Leu Thr Asp Leu Pro Glu Leu Pro Gln Ser Leu Glu Ser
                165                 170                 175

Leu Arg Val Asp Asn Asn Asn Leu Lys Ala Leu Ser Asp Leu Pro Pro
            180                 185                 190

Ser Leu Glu Tyr Leu Thr Ala Ser Ser Asn Lys Leu Glu Glu Leu Pro
        195                 200                 205

Glu Leu Gln Asn Leu Pro Phe Leu Ala Ala Ile Tyr Ala Asp Asn Asn
    210                 215                 220

Leu Leu Glu Thr Leu Pro Asp Leu Pro Pro Ser Leu Lys Lys Leu His
```

-continued

```
225                 230                 235                 240

Val Arg Glu Asn Asp Leu Thr Asp Leu Pro Glu Leu Pro Gln Ser Leu
                245                 250                 255

Glu Ser Leu Arg Val Asp Asn Asn Asn Leu Lys Ala Leu Ser Asp Leu
            260                 265                 270

Pro Pro Ser Leu Glu Tyr Leu Thr Ala Ser Ser Asn Lys Leu Glu Glu
        275                 280                 285

Leu Pro Glu Leu Gln Asn Leu Pro Phe Leu Ala Ala Ile Tyr Ala Asp
    290                 295                 300

Asn Asn Leu Leu Glu Thr Leu Pro Asp Leu Pro Pro His Leu Glu Ile
305                 310                 315                 320

Leu Val Ala Ser Tyr Asn Ser Leu Thr Glu Leu Pro Glu Leu Pro Gln
                325                 330                 335

Ser Leu Lys Ser Leu Arg Val Asp Asn Asn Asn Leu Lys Ala Leu Ser
            340                 345                 350

Asp Leu Pro Pro Ser Leu Glu Tyr Leu Thr Ala Ser Ser Asn Lys Leu
        355                 360                 365

Glu Glu Leu Pro Glu Leu Gln Asn Leu Pro Phe Leu Ala Ala Ile Tyr
    370                 375                 380

Ala Asp Asn Asn Leu Leu Glu Thr Leu Pro Asp Leu Pro Pro Ser Leu
385                 390                 395                 400

Lys Lys Leu His Val Arg Glu Asn Asp Leu Thr Asp Leu Pro Glu Leu
                405                 410                 415

Pro Gln Ser Leu Thr Phe Leu Asp Val Ser Asp Asn Asn Ile Ser Gly
            420                 425                 430

Leu Ser Glu Leu Pro Pro Asn Leu Tyr Tyr Leu Asp Ala Ser Ser Asn
        435                 440                 445

Glu Ile Arg Ser Leu Cys Asp Leu Pro Pro Ser Leu Val Asp Leu Asn
    450                 455                 460

Val Lys Ser Asn Gln Leu Ser Glu Leu Pro Ala Leu Pro Pro His Leu
465                 470                 475                 480

Glu Arg Leu Ile Ala Ser Phe Asn Tyr Leu Ala Glu Val Pro Glu Leu
                485                 490                 495

Pro Gln Asn Leu Lys Gln Leu His Val Glu Gln Asn Ala Leu Arg Glu
            500                 505                 510

Phe Pro Asp Ile Pro Glu Ser Leu Glu Glu Leu Glu Met Asp Ser Glu
        515                 520                 525

Arg Val Val Asp Pro Tyr Glu Phe Ala His Glu Thr Thr Asp Lys Leu
    530                 535                 540

Glu Asp Asp Val Phe Glu
545                 550

<210> SEQ ID NO 2
<211> LENGTH: 367
<212> TYPE: PRT
<213> ORGANISM: Yersinia pestis
<220> FEATURE:
<221> NAME/KEY: MISC_FEATURE
<223> OTHER INFORMATION: biovar Microtus str. 91001

<400> SEQUENCE: 2

Met Phe Ile Asn Pro Arg Asn Val Ser Asn Thr Phe Leu Gln Glu Pro
1               5                   10                  15

Leu Arg His Ser Ser Asn Leu Thr Glu Met Pro Val Glu Ala Glu Asn
            20                  25                  30

-continued

Val Lys Ser Lys Thr Glu Tyr Tyr Asn Ala Trp Ser Glu Trp Glu Arg
            35                  40                  45

Asn Ala Pro Pro Gly Asn Gly Glu Gln Arg Glu Met Ala Val Ser Arg
        50                  55                  60

Leu Arg Asp Cys Leu Asp Arg Gln Ala His Glu Leu Glu Leu Asn Asn
 65                 70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
            100                 105                 110

Leu Lys Ser Leu Leu Val Asp Asn Asn Leu Lys Ala Leu Ser Asp
        115                 120                 125

Leu Pro Pro Leu Leu Glu Tyr Leu Gly Val Ser Asn Asn Gln Leu Glu
        130                 135                 140

Lys Leu Pro Glu Leu Gln Asn Ser Ser Phe Leu Lys Ile Ile Asp Val
145                 150                 155                 160

Asp Asn Asn Ser Leu Lys Lys Leu Pro Asp Leu Pro Pro Ser Leu Glu
                165                 170                 175

Phe Ile Ala Ala Gly Asn Asn Gln Leu Glu Glu Leu Pro Glu Leu Gln
            180                 185                 190

Asn Leu Pro Phe Leu Thr Thr Ile Tyr Ala Asp Asn Asn Leu Leu Lys
        195                 200                 205

Thr Leu Pro Asp Leu Pro Pro Ser Leu Glu Ala Leu Asn Val Arg Asp
        210                 215                 220

Asn Tyr Leu Thr Asp Leu Pro Glu Leu Pro Gln Ser Leu Thr Phe Leu
225                 230                 235                 240

Asp Val Ser Glu Asn Ile Phe Ser Gly Leu Ser Glu Leu Pro Pro Asn
                245                 250                 255

Leu Tyr Tyr Leu Asn Ala Ser Ser Asn Glu Ile Arg Ser Leu Cys Asp
            260                 265                 270

Leu Pro Pro Ser Leu Glu Glu Leu Asn Val Ser Asn Asn Lys Leu Ile
        275                 280                 285

Glu Leu Pro Ala Leu Pro Pro Arg Leu Glu Arg Leu Ile Ala Ser Phe
        290                 295                 300

Asn His Leu Ala Glu Val Pro Glu Leu Pro Gln Asn Leu Lys Gln Leu
305                 310                 315                 320

His Val Glu Tyr Asn Pro Leu Arg Glu Phe Pro Asp Ile Pro Glu Ser
                325                 330                 335

Val Glu Asp Leu Arg Met Asn Ser Glu Arg Val Val Asp Pro Tyr Glu
            340                 345                 350

Phe Ala His Glu Thr Thr Asp Lys Leu Glu Asp Asp Val Phe Glu
        355                 360                 365

<210> SEQ ID NO 3
<211> LENGTH: 388
<212> TYPE: PRT
<213> ORGANISM: Yersinia pestis
<220> FEATURE:
<221> NAME/KEY: MISC_FEATURE
<223> OTHER INFORMATION: Angola

<400> SEQUENCE: 3

Met Tyr Val Phe Val Cys Ser Glu Lys Leu Asp Asn Lys Asn Ile Phe
 1               5                  10                  15

Arg Lys Ala Phe Asn Met Phe Ile Asn Pro Arg Asn Val Ser Asn Thr
            20                  25                  30

Phe Leu Gln Glu Pro Leu Arg His Ser Ser Asn Leu Thr Glu Met Pro
         35                  40                  45

Val Glu Ala Glu Asn Val Lys Ser Lys Thr Glu Tyr Tyr Asn Ala Trp
 50                  55                  60

Ser Glu Trp Glu Arg Asn Ala Pro Pro Gly Asn Gly Glu Gln Arg Glu
 65                  70                  75                  80

Met Ala Val Ser Arg Leu Arg Asp Cys Leu Asp Arg Gln Ala His Glu
                 85                  90                  95

Leu Glu Leu Asn Asn Leu Gly Leu Ser Ser Leu Pro Glu Leu Pro Pro
             100                 105                 110

His Leu Glu Ser Leu Val Ala Ser Cys Asn Ser Leu Thr Glu Leu Pro
         115                 120                 125

Glu Leu Pro Gln Ser Leu Lys Ser Leu Leu Val Asp Asn Asn Asn Leu
130                 135                 140

Lys Ala Leu Ser Asp Leu Pro Pro Leu Glu Tyr Leu Gly Val Ser
145                 150                 155                 160

Asn Asn Gln Leu Glu Lys Leu Pro Glu Leu Gln Asn Ser Ser Phe Leu
                165                 170                 175

Lys Ile Ile Asp Val Asp Asn Asn Ser Leu Lys Lys Leu Pro Asp Leu
             180                 185                 190

Pro Leu Ser Leu Glu Ser Ile Val Ala Gly Asn Asn Ile Leu Glu Glu
         195                 200                 205

Leu Pro Glu Leu Gln Asn Leu Pro Phe Leu Thr Thr Ile Tyr Ala Asp
210                 215                 220

Asn Asn Leu Leu Lys Thr Leu Pro Asp Leu Pro Ser Leu Glu Ala
225                 230                 235                 240

Leu Asn Val Arg Asp Asn Tyr Leu Thr Asp Leu Pro Glu Leu Pro Gln
                245                 250                 255

Ser Leu Thr Phe Leu Asp Val Ser Glu Asn Ile Phe Ser Gly Leu Ser
             260                 265                 270

Glu Leu Pro Pro Asn Leu Tyr Tyr Leu Asn Ala Ser Ser Asn Glu Ile
         275                 280                 285

Arg Ser Leu Cys Asp Leu Pro Pro Ser Leu Glu Leu Asn Val Ser
290                 295                 300

Asn Asn Lys Leu Ile Glu Leu Pro Ala Leu Pro Pro Arg Leu Glu Arg
305                 310                 315                 320

Leu Ile Ala Ser Phe Asn His Leu Ala Glu Val Pro Glu Leu Pro Gln
                325                 330                 335

Asn Leu Lys Gln Leu His Val Glu Tyr Asn Pro Leu Arg Glu Phe Pro
             340                 345                 350

Asp Ile Pro Glu Ser Val Glu Asp Leu Arg Met Asn Ser Glu Arg Val
         355                 360                 365

Val Asp Pro Tyr Glu Phe Ala His Glu Thr Thr Asp Lys Leu Glu Asp
370                 375                 380

Asp Val Phe Glu
385

<210> SEQ ID NO 4
<211> LENGTH: 367
<212> TYPE: PRT
<213> ORGANISM: Yersinia enterocolitica
<220> FEATURE:
<221> NAME/KEY: MISC_FEATURE
<223> OTHER INFORMATION: subsp. enterocolitica 8081

<400> SEQUENCE: 4

```
Met Phe Ile Thr Pro Arg Asn Val Ser Asn Thr Phe Leu Gln Glu Pro
1               5                   10                  15

Leu Arg His Ser Ser Asp Leu Thr Glu Met Pro Val Glu Ala Glu Asn
            20                  25                  30

Val Lys Ser Lys Thr Glu Tyr Tyr Asn Ala Trp Ala Val Trp Glu Arg
        35                  40                  45

Asn Ala Pro Pro Gly Asn Gly Glu Gln Arg Glu Met Ala Val Ser Arg
    50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
            100                 105                 110

Leu Lys Ser Leu Gln Val Asp Asn Asn Leu Lys Ala Leu Ser Asp
        115                 120                 125

Leu Pro Pro Ser Leu Glu Phe Leu Ala Ala Gly Asn Asn Gln Leu Glu
    130                 135                 140

Glu Leu Pro Glu Leu Gln Asn Ser Ser Phe Leu Lys Ile Ile Asp Val
145                 150                 155                 160

Asp Asn Asn Ser Leu Lys Lys Leu Pro Asp Leu Pro Pro Ser Leu Glu
                165                 170                 175

Phe Leu Ala Ala Gly Asn Asn Gln Leu Glu Glu Leu Ser Gly Leu Gln
            180                 185                 190

Asn Leu Pro Phe Leu Thr Glu Ile His Ala Asp Asn Asn Ser Leu Lys
        195                 200                 205

Thr Leu Pro Asp Leu Pro Pro Ser Leu Lys Thr Leu Asn Val Arg Glu
    210                 215                 220

Asn Tyr Leu Thr Asp Leu Pro Glu Leu Pro Gln Ser Leu Thr Phe Leu
225                 230                 235                 240

Asp Val Ser Asp Asn Ile Phe Ser Gly Leu Ser Glu Leu Pro Pro Asn
                245                 250                 255

Leu Tyr Tyr Leu Asp Ala Ser Ser Asn Gly Ile Arg Ser Leu Cys Asp
            260                 265                 270

Leu Pro Pro Ser Leu Val Glu Leu Asp Val Arg Asp Asn Gln Leu Ile
        275                 280                 285

Glu Leu Pro Ala Leu Pro Pro His Leu Glu Arg Leu Ile Ala Ser Leu
    290                 295                 300

Asn His Leu Ala Glu Val Pro Glu Leu Pro Gln Asn Leu Lys Gln Leu
305                 310                 315                 320

His Val Glu His Asn Ala Leu Arg Glu Phe Pro Asp Ile Pro Glu Ser
                325                 330                 335

Val Glu Asp Leu Arg Met Asp Ser Glu Arg Val Thr Asp Thr Tyr Glu
            340                 345                 350

Phe Ala His Glu Thr Thr Asp Lys Leu Glu Asp Asp Val Phe Glu
        355                 360                 365
```

<210> SEQ ID NO 5
<211> LENGTH: 526
<212> TYPE: PRT
<213> ORGANISM: Yersinia enterocolitica

<400

-continued

```
Met Tyr Gly Phe Val Cys Asn Glu Lys Pro Asp Asn Lys Asn Ile Phe
1               5                   10                  15

Arg Arg Ala Phe Asn Met Phe Ile Asn Pro Arg Asn Val Ser Asn Thr
            20                  25                  30

Phe Leu Gln Glu Pro Leu Arg His Ser Ser Asp Leu Thr Glu Ile Pro
        35                  40                  45

Val Glu Ala Glu Asn Val Lys Ser Lys Thr Glu Tyr Tyr Asn Ala Trp
    50                  55                  60

Ser Glu Trp Glu Arg Asn Ala Pro Gly Asn Gly Glu Gln Arg Glu
65                  70                  75                  80

Met Ala Val Ser Arg Leu Arg Asp Cys Leu Asp Arg Gln Ala His Glu
                85                  90                  95

Leu Glu Leu Asn Asn Leu Gly Leu Ser Ser Leu Pro Glu Leu Pro Pro
            100                 105                 110

His Leu Glu Arg Leu Val Ala Ser Cys Asn Ser Leu Thr Glu Leu Pro
        115                 120                 125

Glu Leu Pro Gln Ser Leu Lys Ser Leu Glu Val Tyr Glu Asn Asn Leu
    130                 135                 140

Lys Ala Leu Pro Asp Leu Pro Pro Leu Leu Val Asp Leu Arg Val Phe
145                 150                 155                 160

Asn Asn Gln Leu Glu Glu Leu Pro Glu Leu Gln Asn Leu Pro Phe Leu
                165                 170                 175

Thr Glu Ile Tyr Ala Asn Asn Ser Leu Lys Thr Leu Pro Asp Leu
            180                 185                 190

Pro Pro Ser Leu Val Asp Leu Asn Val Arg Glu Asn Tyr Leu Thr Ala
        195                 200                 205

Leu Pro Glu Leu Pro Gln Ser Leu Ile Phe Leu Asp Ile Ser Asp Asn
    210                 215                 220

Ile Leu Ser Gly Leu Ser Glu Leu Pro Pro Asn Leu Ser Cys Leu Asp
225                 230                 235                 240

Ala Ser Arg Asn Gly Ile Arg Ser Leu Cys Asp Leu Pro Pro Ser Leu
                245                 250                 255

Val Tyr Leu Asp Val Arg Asp Asn Gln Leu Ile Glu Leu Pro Ala Leu
            260                 265                 270

Pro Ser Gly Leu Glu Arg Leu Ile Ala Ser Phe Asn His Leu Ala Glu
        275                 280                 285

Leu Pro Glu Leu Pro Pro Asn Leu Tyr Tyr Leu Asp Ala Ser Arg Asn
    290                 295                 300

Glu Ile Ser Ser Leu Cys Asp Leu Pro Pro Ser Leu Val Asp Leu Asn
305                 310                 315                 320

Val Arg Lys Asn Gln Leu Ile Glu Leu Pro Ala Leu Pro Pro Asp Leu
                325                 330                 335

Glu Arg Leu Ile Ala Ser Phe Asn His Leu Ala Glu Leu Pro Glu Leu
            340                 345                 350

Pro Pro Asn Leu Ser Tyr Leu Asp Ala Ser Arg Asn Glu Ile Ser Ser
        355                 360                 365

Leu Cys Asp Leu Pro Pro Ser Leu Val Asp Leu Asn Val Arg Lys Asn
370                 375                 380

Gln Leu Ile Glu Leu Pro Ala Leu Pro Pro Asp Leu Glu Arg Leu Ile
385                 390                 395                 400

Ala Ser Phe Asn His Leu Ala Glu Leu Pro Glu Leu Pro Pro Asn Leu
                405                 410                 415

Ser Tyr Leu Asp Ala Ser Arg Asn Glu Ile Ser Ser Leu Cys Asp Leu
```

```
                      420             425             430
Pro Pro Ser Leu Val Glu Leu Asp Val Arg Asp Asn Gln Leu Ile Glu
        435                 440                 445

Leu Pro Ala Leu Pro Pro His Leu Glu Arg Leu Ile Ala Ser Leu Asn
    450                 455                 460

His Leu Ala Glu Val Pro Glu Leu Pro Gln Asn Leu Lys Gln Leu His
465                 470                 475                 480

Val Glu His Asn Ala Leu Arg Glu Phe Pro Asp Ile Pro Glu Ser Val
                485                 490                 495

Glu Asp Leu Arg Met Asp Ser Glu Arg Val Ile Asp Pro Tyr Glu Phe
            500                 505                 510

Ala His Glu Thr Ile Asp Lys Leu Glu Asp Asp Val Phe Glu
        515                 520                 525

<210> SEQ ID NO 6
<211> LENGTH: 367
<212> TYPE: PRT
<213> ORGANISM: Yersinia enterocolitica

<400> SEQUENCE: 6

Met Phe Ile Asn Pro Arg Asn Val Ser Asn Thr Phe Leu Gln Glu Pro
1               5                   10                  15

Leu Arg His Ser Ser As

```
Leu Pro Pro Ser Leu Val Glu Leu Asp Val Arg Asp Asn Gln Leu Ile
            275                 280                 285
Glu Leu Pro Ala Leu Pro Pro Arg Leu Glu Arg Leu Ile Ala Ser Phe
290                 295                 300
Asn His Leu Ala Glu Val Pro Glu Leu Pro Gln Asn Leu Lys Leu Leu
305                 310                 315                 320
His Val Glu Tyr Asn Ala Leu Arg Glu Phe Pro Asp Ile Pro Glu Ser
                325                 330                 335
Val Glu Asp Leu Arg Met Asp Ser Glu Arg Val Ile Asp Pro Tyr Glu
                340                 345                 350
Phe Ala His Glu Thr Ile Asp Lys Leu Glu Asp Asp Val Phe Glu
                355                 360                 365

<210> SEQ ID NO 7
<211> LENGTH: 409
<212> TYPE: PRT
<213> ORGANISM: Yersinia pestis
<220> FEATURE:
<221> NAME/KEY: MISC_FEATURE
<223> OTHER INFORMATION: KIM or CO92

<400> SEQUENCE: 7

Met Phe Ile Asn Pro Arg Asn Val Ser Asn Thr Phe Leu Gln Glu Pro
1               5                   10                  15
Leu Arg His Ser Ser Asn Leu Thr Glu Met Pro Val Glu Ala Glu Asn
                20                  25                  30
Val Lys Ser Lys Thr Glu Tyr Tyr Asn Ala Trp Ser Glu Trp Glu Arg
            35                  40                  45
Asn Ala Pro Pro Gly Asn Gly Glu Gln Arg Glu Met Ala Val Ser Arg
50                  55                  60
Leu Arg Asp Cys Leu Asp Arg Gln Ala His Glu Leu Glu Leu Asn Asn
65                  70                  75                  80
Leu Gly Leu Ser Ser Leu Pro Glu Leu Pro Pro His Leu Glu Ser Leu
                85                  90                  95
Val Ala Ser Cys Asn Ser Leu Thr Glu Leu Pro Glu Leu Pro Gln Ser
                100                 105                 110
Leu Lys Ser Leu Leu Val Asp Asn Asn Leu Lys Ala Leu Ser Asp
            115                 120                 125
Leu Pro Pro Leu Glu Tyr Leu Gly Val Ser Asn Asn Gln Leu Glu
            130                 135                 140
Lys Leu Pro Glu Leu Gln Asn Ser Ser Phe Leu Lys Ile Ile Asp Val
145                 150                 155                 160
Asp Asn Asn Ser Leu Lys Lys Leu Pro Asp Leu Pro Pro Ser Leu Glu
                165                 170                 175
Phe Ile Ala Ala Gly Asn Asn Gln Leu Glu Glu Leu Pro Glu Leu Gln
                180                 185                 190
Asn Leu Pro Phe Leu Thr Ala Ile Tyr Ala Asp Asn Asn Ser Leu Lys
                195                 200                 205
Lys Leu Pro Asp Leu Pro Leu Ser Leu Glu Ser Ile Val Ala Gly Asn
            210                 215                 220
Asn Ile Leu Glu Glu Leu Pro Glu Leu Gln Asn Leu Pro Phe Leu Thr
225                 230                 235                 240
Thr Ile Tyr Ala Asp Asn Asn Leu Leu Lys Thr Leu Pro Asp Leu Pro
                245                 250                 255
Pro Ser Leu Glu Ala Leu Asn Val Arg Asp Asn Tyr Leu Thr Asp Leu
                260                 265                 270
```

```
Pro Glu Leu Pro Gln Ser Leu Thr Phe Leu Asp Val Ser Glu Asn Ile
            275                 280                 285

Phe Ser Gly Leu Ser Glu Leu Pro Pro Asn Leu Tyr Tyr Leu Asn Ala
        290                 295                 300

Ser Ser Asn Glu Ile Arg Ser Leu Cys Asp Leu Pro Pro Ser Leu Glu
305                 310                 315                 320

Glu Leu Asn Val Ser Asn Asn Lys Leu Ile Glu Leu Pro Ala Leu Pro
                325                 330                 335

Pro Arg Leu Glu Arg Leu Ile Ala Ser Phe Asn His Leu Ala Glu Val
            340                 345                 350

Pro Glu Leu Pro Gln Asn Leu Lys Gln Leu His Val Glu Tyr Asn Pro
            355                 360                 365

Leu Arg Glu Phe Pro Asp Ile Pro Glu Ser Val Glu Asp Leu Arg Met
        370                 375                 380

Asn Ser Glu Arg Val Val Asp Pro Tyr Glu Phe Ala His Glu Thr Thr
385                 390                 395                 400

Asp Lys Leu Glu Asp Asp Val Phe Glu
                405
```

<210> SEQ ID NO 8
<211> LENGTH: 454
<212> TYPE: PRT
<213> ORGANISM: Yersinia pestis

<400> SEQUENCE: 8

```
Met Phe Ile Asn Pro Arg Asn Val Ser Asn Thr Phe Leu Gln Glu Pro
1               5                   10                  15

Leu Arg His Ser Ser Asn Leu Thr Glu Met Pro Val Glu Ala Glu Asn
            20                  25                  30

Val Lys Ser Lys Thr Glu Tyr Tyr Asn Ala Trp Ser Glu Trp Glu Arg
        35                  40                  45

Asn Ala Pro Pro Gly Asn Gly Glu Gln Arg Glu Met Ala Val Ser Arg
    50                  55                  60

Leu Arg Asp Cys Leu Asp Arg Gln Ala His Glu Leu Glu Leu Asn Asn
65                  70                  75                  80

Leu Gly Leu Ser Ser Leu Pro Glu Leu Pro Pro His Leu Glu Ser Leu
                85                  90                  95

Val Ala Ser Cys Asn Ser Leu Thr Glu Leu Pro Glu Leu Pro Gln Ser
            100                 105                 110

Leu Lys Ser Leu Leu Val Asp Asn Asn Leu Lys Ala Leu Ser Asp
            115                 120                 125

Leu Pro Pro Leu Leu Glu Tyr Leu Gly Val Ser Asn Asn Gln Leu Glu
        130                 135                 140

Lys Leu Pro Glu Leu Gln Asn Ser Ser Phe Leu Lys Ile Ile Asp Val
145                 150                 155                 160

Asp Asn Asn Ser Leu Lys Lys Leu Pro Asp Leu Pro Ser Leu Glu
                165                 170                 175

Phe Ile Ala Ala Gly Asn Asn Gln Leu Glu Glu Leu Pro Glu Leu Gln
            180                 185                 190

Asn Leu Pro Phe Leu Thr Ala Ile Tyr Ala Asp Asn Ser Leu Lys
            195                 200                 205

Lys Leu Pro Asp Leu Pro Leu Ser Leu Glu Ser Ile Val Ala Gly Asn
        210                 215                 220

Asn Ile Leu Glu Glu Leu Pro Glu Leu Gln Asn Leu Pro Phe Leu Thr
```

```
225                 230                 235                 240
Thr Ile Tyr Ala Asp Asn Asn Leu Leu Lys Thr Leu Pro Asp Leu Pro
                245                 250                 255

Pro Ser Leu Glu Ala Leu Asn Val Arg Asp Asn Tyr Leu Thr Asp Leu
                260                 265                 270

Pro Glu Leu Pro Gln Ser Leu Thr Phe Leu Asp Val Ser Glu Asn Ile
            275                 280                 285

Phe Ser Gly Leu Ser Glu Leu Pro Pro Asn Leu Tyr Tyr Leu Asn Ala
            290                 295                 300

Ser Ser Asn Glu Ile Arg Ser Leu Cys Asp Leu Pro Pro Ser Leu Glu
305                 310                 315                 320

Glu Leu Asn Val Ser Asn Asn Lys Leu Ile Glu Leu Pro Ala Leu Pro
                325                 330                 335

Pro Arg Leu Glu Arg Leu Ile Ala Ser Phe Asn His Leu Ala Glu Val
                340                 345                 350

Pro Glu Leu Pro Gln Asn Leu Lys Gln Leu His Val Glu Tyr Asn Pro
            355                 360                 365

Leu Arg Glu Phe Pro Asp Ile Pro Glu Ser Val Glu Asp Leu Arg Met
        370                 375                 380

Asn Ser His Leu Ala Glu Val Pro Glu Leu Pro Gln Asn Leu Lys Gln
385                 390                 395                 400

Leu His Val Glu Thr Asn Pro Leu Arg Glu Phe Pro Asp Ile Pro Glu
                405                 410                 415

Ser Val Glu Asp Leu Arg Met Asn Ser Glu Arg Val Val Asp Pro Tyr
            420                 425                 430

Glu Phe Ala His Glu Thr Thr Asp Lys Leu Glu Asp Asp Val Phe Glu
        435                 440                 445

His His His His His His
        450
```

YOPM AS DELIVERY VEHICLE FOR CARGO MOLECULES AND AS BIOLOGICAL THERAPEUTIC FOR IMMUNOMODULATION OF INFLAMMATORY REACTIONS

This application claims benefit from International Application No. PCT/EP2009/053159, which was filed on Mar. 17, 2009, which in turn claims priority to European Patent Application No. 08004967.9, filed on Mar. 17, 2008, wherein the entireties of said patent applications are incorporated herein by reference. Also, the entire contents of the ASCII text file entitled "DFM0007US-SequenceListing.txt," created on Nov. 11, 2011, having a size of 30 kilobytes is incorporated herein by reference.

The present invention relates to the use of *Yersinia* outer protein M (YopM), a YopM fragment or a YopM variant, which is capable of autopenetrating the cell membrane and of integrating into the cell cytosol without the requirement of additional factors for delivering a cargo molecule across the membrane to the cytosol of a cell. The present invention also relates to a pharmaceutical composition comprising YopM, a YopM fragment or a YopM variant being capable of autopenetrating the cell membrane and of integrating into the cell cytosol without the requirement of additional factors for the regulation of inflammatory reactions of the immune system and the treatment of diseases of the host. The present invention further relates to a YopM fragment or variant, which is capable of autopenetrating the cell membrane and of integrating into the cell cytosol without the requirements of additional factors as well as such proteins or YopM linked to a cargo molecule.

Immunosuppressive reactions, i.e. reactions, which lead to the inhibition or prevention of the activity of the immune system, are derivable either from a natural background and are, thus, largely pathogenic for the body or they are due to intentional medical actions.

In the first case pathogenic microorganisms, in order to successfully infect a host organism, have to protect their respective niches by undermining, circumventing, destroying, or even exploiting the human defense system. For this they have developed various ingenious strategies involving a plethora of secreted and cell-associated factors. Pathogenic species of the genus *Yersinia* are able to suppress the host's innate immune response. For this purpose, Yersiniae employ a type III secretion system (T3SS) consisting of a Ysc injectisome spanning the bacterial membranes, *Yersinia* outer protein (Yop) effectors and Yop translocators needed to deliver the effectors across the membrane (Cornelis G R., Int J Med Microbiol. 2002 February; 291(6-7):455-62). The type III secretion system is encoded on a virulence plasmid that is common to all three pathogenic *Yersinia* species: *Y. enterocolitica*, *Y. pseudotuberculosis*, and *Y. pestis*. Pathogenic Yersiniae require this T3SS to survive and replicate extracellularly within lymphoid tissues of their animal or human hosts. The *Yersinia* outer proteins (Yops), a set of pathogenicity factors, are translocated by this T3SS into host cells (Cornelis G R., Int J Med Microbiol. 2002 February; 291(6-7):455-62). Two Yops (YopB and YopD) are inserted into the host plasma membrane, where they function as a translocation pore for six additional effector Yops (YopO, YopH, YopM, YopT, YopJ/YopP and YopE) into the cytosol of the host cell. The hallmark of the Yop's function is the counteraction of innate immune responses by preventing phagocytosis of *Yersinia* and downregulating secretion of proinflammatory cytokines. The signalling pathways targeted by Yops are initiated by phagocytic receptors, toll like receptors (TLRs), and antigen receptors. Yops function to interfere with multiple signalling responses of the infected cell, for example by regulation of Rho-GTP-binding proteins, focal adhesion proteins, inflammatory pathways, and cell survival/apoptosis (Aepfelbacher, M., Trasak, C., and Ruckdeschel, K. (2007) *Thromb Haemost* 98: 521-529; Viboud, G. I. and Bliska J. B. (2005) *Annu. Rev. Microbiol.* 59: 69-89). In vivo studies show that YopH, YopM, and YopE, are the most important Yops for virulence and counteraction of innate immune responses.

Although Yops are bacterial proteins, they often have enzymatic activities related to functions of eukaryotic cells. For example, YopH is a highly active protein tyrosine phosphatase that targets β1integrin-mediated phagocytotic pathways, and YopE is a GTPase-activating protein that targets Rho-GTPases. YopM is the only effector of *Yersinia* that does not have a known enzymatic activity. After translocation into the host cytosol, YopM traffics to the nucleus via a vesicle-associated pathway. However, until now, it remains elusive how nuclear localization is related to YopM's function (Skrzypek, E., Cowan, C. and Straley, S. C. (1998). *Mol. Microbiol.* 30: 1051-1065). The YopM protein consists of two amino-terminal helices followed by variable numbers of an approximately 20 amino acid leucine-rich repeat (LRR) motif (12-20 LRR among different *Yersinia* strains), forming a horseshoe-shaped protein. The LRR, which have been implicated in protein-protein interactions, make up most of YopM (see FIG. 1). Besides protein-protein interactions with serum proteins such as α-thrombin and α1-antitrypsin (Hines, L., Skrzypek, E., Kajava, A. V., and Straley, S. C. (2000) *Microbial Pathogenesis* 30: 193-209; Heusipp, G., Spekker, K., Brast, S., Falker, S. and Schmidt, M. A. (2006) *Microbiology* 152: 1327-1335) and an apparent scaffolding function of YopM with two cytoplasmic kinases, RSK1 and PRK2 (McDonald, C., Vacratis, P. O., Bliska, J. B. and Dixon, J. E. (2003). *J. Biol. Chem* 278: 18514-18523) the molecular function of YopM during infection is only poorly understood.

According to the current model of *Y. enterocolitica* infection, YopM is translocated through the T3SS into the host cell cytoplasm. However, other studies suggest an extracellular role of YopM, like binding to the acute-phase protein α1-antitrypsin, and binding of YopM to serum protein α-thrombin as well as a strong humoral immune response to YopM after infection of mice (Benner, G. E., Andrews, G. P., Byrne, W. R., Strachan, S. D., Sample, A. K., Heath, D. G. and Friedlander, A. M. (1999) *Infect Immun.* 67: 1922-1928; Heusipp, G., Spekker, K., Brast, S., Fälker, S. and Schmidt, M. A. (2006)*Microbiology,* 152: 1327-1335; Hueck, C. J. (1998) *Microbiol. Mol. Biol. Rev.* 62: 379-433). Furthermore, an apolar secretion (7%) of YopM during in vitro infection has been described by Cheng and Schneewind (Cheng, L. W. and Schneewind, O. (2000) *J. Bacteriol.* 182: 3183-3190). The fact that yopM mutants of *Y. enterocolitica* and *Y. pestis* cannot establish a systemic infection in infected mice (Trulzsch, K., Sporleder, T., Igwe, E. I., Russmann, H., and Heesemann, J. (2004) *Infect. Immun.* 72:5227-34; Kerschen, E. J., Cohen, D. A., Kaplan, A. M. and Stranley, S. C. (2004) *Infect. Immun.* 72: 4589-4602) indicates that YopM is important for full virulence and resistance to innate immunity during infection (Leung, K. Y., Reisner, B. S. and Straley, S. C. (1990) *Infect. Immun.* 58: 3262-3271).

In the second case of intentional medical actions, immunosuppressive activity of compounds is used for the regulation, in particular the controlled and purposeful inhibition or prevention of the activity of the immune system. The corresponding compounds are generally summarized as immunosuppressants or immuno-suppressive drugs. Immunosuppressive drugs are a heterogenic collection generally classified into the following groups: (1) glucocorticoids, (2) cytostatics, (3) antibodies, (4) drugs acting on immunophilins, and (5) TNF-binding proteins.

In pharmacologic doses, glucocorticoids are used to suppress various allergic, inflammatory, and autoimmune disorders. They are also administered as posttransplantory immunosuppressants to prevent the acute transplant rejection and graft-versus-host disease. However, they do not prevent an infection and also inhibit later reparative processes. Glucocorticoids suppress the cell-mediated immunity. They act by inhibiting genes that code for the cytokines IL-1, IL-2, IL-3, IL-4, IL-5, IL-6, IL-8, IFN-γ, and TNF-α, the most important of which is IL-2. Reduced cytokine production in turn reduces the T cell proliferation. Glucocorticoids also suppress the humoral immunity, causing B cells to express smaller amounts of IL-2 and IL-2 receptors. This diminishes both B cell clone expansion and antibody synthesis. Glucocorticoids influence all types of inflammatory events. They induce the synthesis of lipocortin-1 (annexin-1), which subsequently binds to cell membranes preventing the phospholipase A2 from interacting with its substrate arachidonic acid, leading to diminished eicosanoid production. The expression of cyclooxygenases COX-1 and COX-2 is also suppressed, which potentiates the effect. Furthermore, glucocorticoids stimulate lipocortin-1 escaping to the extracellular space, where it binds to the leukocyte membrane receptors and inhibits various inflammatory events like epithelial adhesion, emigration, chemotaxis, phagocytosis, respiratory burst, and the release of various inflammatory mediators (lysosomal enzymes, cytokines, tissue plasminogen activator, chemokines, etc.) from neutrophils, macrophages, and mastocytes.

Cytostatics inhibit cell division. In immunotherapy, they are used in smaller doses than in the treatment of malignant diseases. They affect the proliferation of both T cells and B cells. Due to their highest effectiveness, purine analogs are most frequently administered as cystostatics. Typically, alkylating agents like nitrogen mustards (cyclophosphamide), nitrosoureas or platinum compounds are used as cytostatics in immunotherapy. Cyclophosphamide is probably the most potent immunosuppressive compound known so far. In small doses, it is very efficient in the therapy of systemic lupus erythematosus, autoimmune hemolytic anemias, Wegener's granulomatosis, and other immune diseases. However, high doses may cause pancytopenia or hemorrhagic cystitis. Further cytostatics are antimetabolites, which interfere with the synthesis of nucleic acids. These include folic acid analogues, such as methotrexate, purine analogues such as azathioprine and mercaptopurine, pyrimidine analogues and protein synthesis inhibitors. Methotrexate is a folic acid analogue. It binds dihydrofolate reductase and prevents synthesis of tetrahydrofolate and is generally used in the treatment of autoimmune diseases like rheumatoid arthritis, as well as in transplantations. Azathioprine is one of the most important immunosuppressive cytotoxic substances. It is extensively used to control transplant rejection reactions. It is nonenzymatically cleaved to mercaptopurine, which acts as a purine analogue and an inhibitor of DNA synthesis. Mercaptopurine itself is also frequently administered directly. By preventing the clonal expansion of lymphocytes in the induction phase of the immune response, it affects both cellular and humoral immunity. It is also efficient in the treatment of autoimmune diseases. A further group of cytostatics are cytotoxic antibiotics. Among these, dactinomycin is currently the most important. It is used in kidney transplantations. Other cytotoxic antibiotics are anthracyclines, mitomycin C, bleomycin, mithramycin.

Immunosuppressive antibodies can be used as a quick and potent immunosuppression method to prevent the acute rejection reaction. This group includes heterologous polyclonal antibodies, which are obtained from the serum of animals previously injected with the patient's thymocytes or lymphocytes. Antilymphocyte (ALG) and antithymocyte antigens (ATG) are typically used for such an approach. They are part of the steroid-resistant acute rejection reaction and grave aplastic anemia treatment. Polyclonal antibodies inhibit T lymphocytes and cause their lysis, which is both complement-mediated cytolysis and cell-mediated opsonization followed by removal of reticuloendothelial cells from the circulation in the spleen and liver. Thus, polyclonal antibodies may inhibit cell-mediated immune reactions, including graft rejection, delayed hypersensitivity and the graft-versus-host disease. However, polyclonal antibodies may affect all lymphocytes and cause general immunosuppression, possibly leading to post-transplant lymphoproliferative disorders (PTLD) or serious infections, especially by cytomegalovirus and previously dormant mycobacteria. Because of the high immunogenicity of polyclonal antibodies, almost all patients exhibit an acute reaction to the treatment. It is characterized by fever, rigor episodes, and even anaphylaxis. Later during the treatment, some patients may develop serum sickness or immune complex glomerulonephritis.

Monoclonal antibodies are directed towards exactly defined antigens (epitopes). Therefore, they cause fewer side-effects. Especially significant are the IL-2 receptor-(CD25−) and CD3-directed antibodies. They are used to prevent the rejection of transplanted organs, but also to track changes in the lymphocyte subpopulations. OKT3 (R) is one of the most important anti-CD3 antibodies. It is known that OKT3 binds TCR/CD3, the T-cell receptor complex. It prevents T-cell activation and proliferation by binding the T-cell receptor complex present on all differentiated T cells. However, during the first few administrations, this binding non-specifically activates T cells, leading to a serious syndrome 30 to 60 minutes later. This is characterized by fever, myalgia, headache, and artralgia. In some cases, it progresses to a life-threatening reaction of the cardiovascular system and the central nervous system, requiring a lengthy therapy. Past this period, CD3 (R) blocks the TCR-antigen binding and causes conformational changes or the removal of the entire TCR3/CD3 from the T-cell surface. This lowers the number of T cells, perhaps by sensitising them for the uptake by the reticular epithelial cells. The cross-binding of CD3 molecules also activates an intracellular signal, causing the T cells' anergy or apoptosis, unless they receive another signal through a costimulatory molecule. CD3 antibodies also shift the balance from Th1 to Th2 cells. In deciding whether to use OKT3 (R) in a patient's treatment, a healthcare practitioner must consider not only its great effectiveness but also its toxic side-effects: The risk of excessive immunosuppression and the risk that the patient develops neutralizing antibodies against the drug could render it inefficacious. Although CD3 (R) antibodies act more specifically than polyclonal antibodies, they may lower the cell-mediated immunity significantly, predisposing the patient to opportunistic infections and malignancies.

Interleukin-2 is an important immune system regulator necessary for the clone expansion and survival of activated T lymphocytes. Its effects are mediated by the trimeric cell surface receptor IL-2R, consisting of the α, β, and γ chains. The IL-2R (CD25, T-cell activation antigen, TAC) is expressed only by the already-activated T lymphocytes. Therefore, it is of special significance to the selective immunosuppressive treatment, and the research has been focused on the development of effective and safe anti-IL-2R antibodies like the chimeric mouse/human anti-Tac antibodies basiliximab (Simulect®) and daclizumab (Zenapax®). These antibodies act by binding the IL-2R receptor's α chain, preventing the IL-2 induced clonal expansion of activated lymphocytes and shortening their survival. They are used, for example, in the prophylaxis of acute organ rejection after bilateral kidney transplantation, both being similarly effective and with only few side effects.

Among the drugs acting on immunophilins is cyclosporin, which is a calcineurin inhibitor. It is a fungal peptide, composed of 11 amino acids and is one of the most-widely-used immunosuppressive drugs. Cyclosporin is thought to bind to the cytosolic protein cyclophilin (an immunophilin) of immunocompetent lymphocytes, especially T-lymphocytes. This complex of cyclosporin and cyclophilin inhibits calcineurin, which under normal circumstances induces the transcription of interleukin-2. The drug also inhibits lymphokine production and interleukin release, leading to a reduced function of effector T-cells. Although cyclosporin is used in the treatment of acute rejection reactions, it may show severe side-effects like nephrotoxicity.

Finally, the group of TNF-binding proteins comprises TNF-α binding monoclonal antibodies or circulating receptors such as infliximab (Remicade®), etanercept (Enbrel®), or adalimumab (Humira®) which prevents TNF-α from inducing the synthesis of IL-1 and IL-6 and the adhesion of lymphocyte-activating molecules. They are used in the treatment of rheumatoid arthritis, ankylosing spondylitis, Crohn's disease, and psoriasis. However, these drugs may raise the risk of contracting tuberculosis or inducing a latent infection to become active. Thus, for example infliximab and adalimumab carry label warnings stating that patients should be evaluated for latent TB infection and treatment should be initiated prior to starting therapy with them.

Thus, although these immunosuppressive drugs are valuable medical tools, they are not without side effects and risks. Because the majority of them act non-selectively, the immune system is less able to resist infections and the spread of malignant cells. Furthermore, the production of the majority of the immunosuppressive drugs is time-consuming and expensive.

Therefore, there is a need for the provision of new, effective and inexpensive immunosuppressants.

Crossing the plasma membrane is a prerequisite for intracellular targeted drug and/or compound delivery (for example in gene therapy where the gene/nucleic acid has to be delivered to an intracellular compartment). Cell penetrating peptides (CPPs) are known to transport cargo molecules attached to it into cells most probably by endocytosis. Nevertheless, there is an ongoing need in the art to provide for compounds, which are able to cross the plasma membrane of higher cells.

The solution to the above-indicated technical problem is achieved by providing the embodiments as characterized herein.

The inventors have found that YopM, which has until now solely been described in the context of the *Yersinia* type III secretion system (T3SS), is surprisingly capable of independently passing, i.e. autopenetrating the cell membrane of a host cell and of integrating into the cell cytosol.

The present inventors have found as well that YopM, which so far has not been characterized as a potential immunosuppressive therapeutic, is, once it has integrated into the cell cytosol, capable of effectively downregulating cytokines, in particular pro-inflammatory cytokines, i.e. it is capable of regulating inflammatory reactions and can, thus, efficiently be used as an immunomodulatory or immunosuppressive agent.

Accordingly, in a first aspect, the present invention centers on the capability of YopM to autopenetrate the cell membrane and to integrate into the cell cytosol, and relates to the use of YopM, a YopM fragment or a YopM variant as defined herein for delivering at least one cargo molecule across the membrane to the cytosol of a cell. Said YopM fragment or YopM variant is capable of autopenetrating the cell membrane and of integrating into the cell cytosol per se i.e. without the requirement of additional factors.

In a second aspect, the present invention provides an immunosuppressive drug, preferably as a pharmaceutical composition, comprising YopM, a YopM fragment or a YopM variant (said fragment or variant preferably being still capable of autopenetrating the cell membrane and of integrating into the cell cytosol without the requirement of additional factors) and/or the immunmodulatory domain of YopM for downregulating pro-inflammatory cytokines. Said immunsuppressive drug/pharmaceutical composition, may thus be used for the treatment of a disease that is associated with an excess and/or an unwanted expression of pro-inflammatory cytokines. YopM and its derivatives can accordingly be used for the regulation of inflammatory reactions of the immune system, for example for the treatment of diseases caused by autoimmunity of the host.

The term "capable of autopenetrating the cell membrane and integrating into the cell cytosol without the requirement of additional factors" means that a compound of the invention, i.e. a YopM, a YopM fragment and/or a YopM variant of the fragment and/or of YopM as defined herein, is capable of passing the cell membrane and of entering the cytosol of a cell without the assistance of exogenous factors, for example those that are not normally present in or on a host cell. Preferably, the term means that a molecule is capable of passing the cell membrane and of entering the cytosol of a cell without the assistance of a type III secretion system (T3SS), preferably that of *Yersinia*, and even more preferred without Yop translocators, for example those of *Yersinia*, which were up to now believed to be mandatory to deliver the effectors across the membrane. Said translocators are known to the skilled person (see for example (Cornelis G R., Int. J. Med. Microbiol., 291(6-7):455-462 (2002) and FIG. 19).

In view of the experimental results disclosed herein in the appended examples, it is clear that the isolated compounds of the invention are capable per se of autopenetrating the cell membrane and integrating into the cell cytosol. "Isolated" means that the YopM, a YopM fragment, and/or a YopM variant of the fragment and/or of YopM is/are separated out of its/their natural environment.

In the context of the present application, the term "YopM, a YopM fragment, a YopM variant of the fragment and/or of YopM and/or the immunomodulatory domain of YopM" are sometimes also denoted as "compound(s) of the invention".

It is envisaged that the present invention relates in general to the use of a isolated *Yersinia* outer protein M (YopM), an isolated YopM fragment or an isolated YopM variant, for delivering at least one cargo molecule across the membrane to the cytosol of a cell. Said isolated YopM, isolated YopM fragment or isolated YopM variant is thereby capable of autopenetrating the cell membrane and, preferably, also of integrating into the cell cytosol.

The term "delivering a cargo molecule" means that said isolated YopM, isolated YopM fragment or isolated YopM variant is thereby capable of transporting and delivering a cargo molecule as defined herein, e.g. peptides or proteins, DNA, RNA, carbohydrates, lipids or chemically devised molecules of natural or non-natural origin without accessory factors into higher cells.

The term "autopenetrating the cell membrane" means that the compounds of the invention are able to cross/pass a membrane which seperates two different compartments. It is preferred that the mentioned two compartments refer to the exterior and interior of a cell. The "cell membrane" is therefore preferably a plasma membrane that separates the interior of a cell from the exterior. It will be understood that the compounds of the invention preferably cross the plasma membrane from the exterior of the cell towards the interior of the cell.

Figure 18:
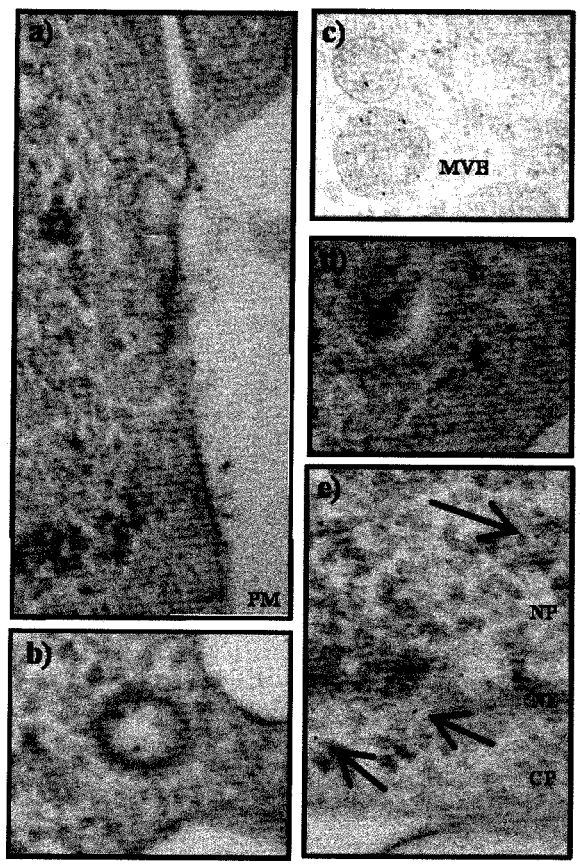

In order to determine YopM's intracellular localization, electron microscopy (EM) with gold-labelled YopM was done (FIG. 18). Early after incubation of HeLa cells (5-15 min at 37° C.), YopM-Au was detected bound to the cell surface (FIG. 18; a) and also appeared to be associated with vesicles in the cytosol (FIG. 18; b). Later after incubation (15-60 min), YopM-Au can be found in multi-vesicular bodies (MVB; FIG. 18; c), which are a typical form of late endosomes (LE). Interestingly, we often observed YopM-associated structures without any distinct membrane (FIG. 18; d).

Moreover, the vesicle membranes seemed to be dissolved, allowing YopM to escape from the endosomal compartment. Finally, YopM-Au was detected (3 h) free in the cytosol, as well as inside the nucleoplasma (FIG. 18; f, indicated by black arrows). This indicates, that YopM initially enters host cells via a vesicle-associated mechanism before entering the cytoplasm at later time points, a process we termed autopenetration and integration into the cell cytosol. Thereafter, YopM appears free in the cytosol, accumulates in perinuclear regions and can enter the nucleus.

It is thus envisaged that the compounds of the invention which "integrate into the cell cytosol", preferably cross the plasma membrane in the above identified manner, i.e. they are first associated with vesicles and subsequently released into the cytosol.

The compounds of the invention may enter eukaryotic cells, preferably those indicated below, without the need to interact with a receptor, i.e. the compounds of the invention may enter eukaryotic cells irrespective of a receptor. The term "cell" means any type of isolated eukaryotic cell, cells in the context of a living organism or in tissue as well as isolated cells/tissues in cell cultures (for example HeLa cells, T84 cells, HL60 cells or XS52 cells etc.). Preferably, the term relates to higher eukaryotic cells, more preferably to animal cells, even more preferably to mammalian cells and most preferred to human cells. Epithelial cells, fibroblasts (for example synovial fibroblasts—see Example 9), primary cells, endothelial cells (for example human intestinal microvascular endothelial cells HIMEC—see Example 8), cells of the immune system like monocytes, dendritic cells, macrophages and/or NK cells are also envisaged.

The capability to pass the cell membrane and to enter the cytosol of a cell without the assistance of exogenous factors can be tested and determined by methods known to a person skilled in the art. The autopenetration of YopM, a YopM fragment or a YopM variant into the cell membrane and its integration into the cell cytosol can be tested by a method of cell fractionation as described e.g. by Kenny B, Finlay B B. Infect Immun. 1997 July; 65(7):2528-36 and/or by the methods described in the appended examples. Briefly, such a method comprises the incubation of cells to be tested, e.g. HeLa cells, with YopM, e.g. a recombinant YopM, a YopM fragment or a YopM variant, e.g. a recombinant YopM fragment or YopM fragment (i.e with a compound of the invention) for a time period of 10 to 60 min, preferably of 20 to 40 min, more preferably of 25 to 35 min and most preferably of 30 min. The YopM, YopM fragment or YopM variant may be present in any suitable medium known to the skilled person. For example, the protein is provided in an infection medium comprising, e.g. DMEM, FCS, L-glutamine, HEPES and methyl-α-D-mannose. Preferably, the infection medium comprises 500 ml DMEM, 10% (v/v) FCS, 1 mM L-glutamine, 10 mM HEPES and 1% (w/v) methyl-α-D-mannose. For the assay cell culture dishes comprising the cells to be tested, e.g. as a confluently grown surface layer may be incubated with the compound(s) of the invention present in an infection medium as described herein above in any suitable concentration, e.g. a concentration of 1 to 100 µg per ml, preferably of 5 to 50 µg per ml, more preferably of 10 to 30 µg per ml and most preferably of 15 to 25 µg per ml. Subsequently, the cells may be washed with any suitable buffer known to the skilled person, e.g. with D-PBS/Mg$^{2+}$. Preferably, the washing is carried out in ice-cold buffer and repeated twice. This is optionally followed by an acid-wash with 0.2 M glycine, pH 2.0. Subsequently, the cells are permeabilised by any suitable means known to the skilled person. Preferably, the cells are suspended in a suitable sonication buffer and the suspension may then be permeabilised by sonication. Subsequently, the resulting suspension may be separated into cell fractions, for example by centrifugation, e.g. at 108.000×g for 15 min at 4° C. After the fractionation step, the supernatant comprising suspended cytoplasmic proteins may be recovered. A resulting pellet may optionally be washed with any suitable buffer known to the person skilled in the art, e.g. with a sonication buffer. The sonication buffer comprises exemplarily TrisHCl, NaCl, EDTA, EGTA, glycerol, NaVO$_4$ and NaF. Preferably, the sonication buffer comprises 50 mM TrisHCl pH 7.6, 150 mM NaCl, 1 mM EDTA, 1 mM EGTA, 30% glycerol, 0.4 mM NaVO$_4$ and 1 mM NaF Subsequently, the pellet may be resuspended in any suitable buffer known to the person skilled in the art, e.g. in a Triton buffer, preferably in 1 ml of a Triton buffer comprising 1% (v/v) Triton in a sonication buffer as described herein above. The suspension may then be incubated in a shaker for a suitable period of time known to the skilled person, e.g. for 30 min at 4° C. at 15 U/min. Subsequently, the suspension may again be centrifuged, e.g. at 108.000×g for 15 min at 4° C. A resulting supernatant may be recovered as 'membrane fraction'. Subsequently, the resulting fractions may be precipitated by suitable means known to the skilled person, e.g. with trichloro acetic acid (TCA). For the detection of autopenetration and integration of YopM, a YopM fragment or a YopM variant, a cytoplasmic and membrane fraction obtained by the method as described herein above may be analysed with any method known to the person skilled in the art, for example by way of immunostaining. Exemplarily, the fractions may be analysed by Western-blotting as known to the person skilled in the art and derivable, e.g., from Lottspeich and Zorbas, (Bioanalytik, 1998). The detection may be performed e.g. with a polyclonal murine YopM antiserum, for example with a polyclonal murine antiserum against full-length *Y. enterolitica* YopM.

A compound of the invention, in particular a YopM, YopM fragment or a YopM variant of the invention, is regarded to be capable of autopenetrating the cell membrane and integrating into the cell cytosol without the requirement of additional factors if a tested molecule can be detected in the cytoplasmic fraction, either associated with vesicles as outlined above or already released in the cytosol, the latter being preferred. More preferably, a compound of the invention is regarded to be capable of autopenetrating the cell membrane and integrating into the cell cytosol without the requirement of additional factors if at least 10%, 20%, 30%, 40%, 50%, 60%, or 70%, 80%, 90%, 91%, 92%, 93%, 94%, 95%, 96%, 97%, 98%, 99% or 100% of the tested compound is detected in the cytoplasmic fraction, in comparison to the total amount of YopM, YopM fragment or YopM variant added. Methods for quantification of the amount of protein uptake are known to the skilled artisan. It is envisaged that the compound of the invention, which is detected in the cytoplasmic fraction, is associated with vesicles as indicated above, and/or already released into the cytosol, the latter being preferred.

Alternatively, the autopenetration of YopM, a YopM fragment or a YopM variant into the cell membrane and its integration into the cell cytosol can be tested by a translocation coefficient assay as known to the person skilled in the art, for example as described in Langel, Ü. (ed) (*Cell-penetrating peptides: Processes and Applications*, CRC Press, Boca Raton, Fla. 2002,) and references therein. Briefly, YopM, a YopM fragment or a YopM variant is linked to a suitable label, for example a dye like for example Cy3 or Cy5 or to gold particles, GFP, RFP etc. Subsequently, a defined amount of the labelled protein is incubated with target cells, for example such as described herein. Afterwards, the cells are lysed and fractionated, for example such as described herein in the context of the method of cell fractionation. A translocation coefficient $K_T=[YopM_{intracellular}]/[YonpM_{extracellular}]$ may be determined by measuring the amount of the label in the intracellular cell fractions $[YopM_{intracellular}]$ and comparing it with the originally used amount for the incubation $[YopM_{extracellular}]$ e.g. by determining the fluorescence of Cy3. Alternatively, ELISA methods may be used or further corresponding methods including e.g. radioactivity counting, biotinylation/cell-ELISA, fluorescence-labeling/spectrophotometer/FACS, resonance energy transfer, HPLC detection, immunodetection, fluorescence correlation microscopy (FCM), cell activity by capillary electrophoresis (CACE), or MALDI-TOF MS, as known to the skilled person, for example such as described in Langel, Ü. (ed) (*Handbook of cell-penetrating peptides*, CRC Press, Boca Raton, Fla., 2007), and Langel, Ü. (ed) (*Cell-penetrating peptides: Processes and Applications*, CRC Press, Boca Raton, Fla. 2002).

The test for determining whether a molecule, in particular a YopM polypeptide, and/or a fragment or variant of the invention is capable of autopenetrating the cell membrane and integrating into the cell cytosol without the requirement of additional factors is preferably a test as described herein e.g. in the Examples.

In another preferred embodiment, the YopM polypeptide, fragment or variant as described herein, which is capable of autopenetrating the cell membrane and of integrating into the cell cytosol without the requirement of additional factors, is also capable of entering the cell nucleus. The term "entering the cell nucleus" means that the YopM polypeptide, fragment or variant passes across the nuclear membrane of a cell. The capability of a YopM polypeptide, YopM fragment or YopM variant to enter the cell nucleus has been demonstrated in the appended Examples and can be tested by any suitable methods and assays known to the person skilled in the art, preferably by nuclear localization assays as described in Hällbrink M., et al., (2004) (Biochem. Biophys. Acta 1667:222) and Nare B., et al., (1999) (Anal. Biol. 267:390). In a preferred embodiment, the capability of a YopM polypeptide, fragment or variant to enter the cell nucleus is linked to the presence of a nuclear localization sequence (NLS). More preferably, a YopM polypeptide, fragment or variant comprises a YopM NLS as known to the person skilled in the art, e.g. a NLS present in leucine-rich repeats 1 to 3 of YopM, preferably in leucine-rich repeats 1 to 3 of SEQ ID NO:4. In a preferred embodiment YopM polypeptides, fragments or variants used in the context of pharmaceutical compositions comprise this NLS sequence, i.e. leucine-rich repeats 1 to 3 of YopM, more preferably they comprise amino acids 74 to 133 of SEQ ID NO: 4.

The term "YopM" according to the invention relates to a *Yersinia* outer protein M. The term includes a *Yersinia* outer protein M as described in Boland A, et al. *EMBO J.* 1996 Oct. 1; 15(19):5191-201; Cornelis G R. *J. Bacteriol.* 1998 November; 180(21):5495-504; Skrzypek, E., Cowan, C. and Straley, S. C. (1998) *Mol. Microbiol.* 30: 1051-1065; McDonald, C., Vacratis, P. O., Bliska, J. B. and Dixon, J. E. (2003) *J. Biol. Chem* 278: 18514-18523; Skrzypek E, Myers-Morales T, Whiteheart S W, Straley S C. *Infect. Immun.* 2003 February; 71(2):937-47; Kerschen, E. J., Cohen, D. A., Kaplan, A. M. and Stranley, S. C. (2004) *Infect. Immun.* 72: 4589-4602 and Heusipp, G., Spekker, K., Brast, S., Fälker, S. and Schmidt, M. A. (2006) *Microbiol.* 152: 1327-1335; or derivable from any biological database known to the person skilled in the art, e.g. from the Genbank database.

In a preferred embodiment, the term "YopM" relates to a *Yersinia* outer protein M of a Yersina strain naturally comprising a YopM encoding virulence plasmid. The term "YopM encoding virulence plasmid" relates to plasmid pYV or pCD1 as described to be present, for instance, in *Yersinia enterocolitica, Yersina pseudotuberculosis* and *Yersinia pestis* (Cornelis et al., *Microbiol. Mol. Biol. Rev.* 62:1315-1352 (1998)).

In a further preferred embodiment the term "YopM" relates to a *Yersinia* outer protein M selected from the species *Yersinia enterolitica, Yersinia pseudotuberculosis* and *Yersinia pestis*. More preferably, the term "YopM" relates to a *Yersinia* outer protein M selected from *Yersinia enterolitica* 8081v, serotype O:8.

The term "YopM", fragment or variant thereof also relates to an polypeptide/amino acid sequence comprising any amino acid sequence selected from the group consisting of SEQ ID NO: 1, SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8.

Polynucleotides encoding these *Yersinia* outer protein M amino acid sequences are also envisaged.

The term "YopM fragment" relates to a sub-portion of the "YopM" polypeptide according to the present invention as described herein above. In particular, the term "YopM fragment" refers to a short amino acid sequence contained in the *Yersinia* outer protein M according to the invention as described herein, wherein said short amino acid sequence contained in the *Yersinia* outer protein M retains the capability of autopenetrating the cell membrane and integrating into the cell cytosol without the requirement of additional factors, as defined above. Protein fragments may be "free-standing", i.e. separated out of their natural environment (which is YopM), or they may be attached to a polypeptide or comprised within a polypeptide of which the fragment forms a part or region, for example as a single continuous region. "Attached to" includes that the YopM fragment and the polypeptide are expressed/expressable on/from a single nucleic acid as a single continuous region or that both entities are linked/coupled otherwise (for example by way of chemical linkage like biotin/streptavidin etc.). Methods to "attach" two entities, in particular two proteins, are well-known to the skilled person.

It is preferred that the polypeptide, to which the YopM fragment is "attached to" or "comprised within", is heterologous to YopM, i.e. it is preferably but not exclusively not derived from *Yersinia*.

The term "short amino acid sequence contained in the *Yersinia* outer protein M" includes but is not limited to fragments from about amino acid number 1-30, 31-60, 61-90, 91-120, 121-150, 151-180, 181-210, 211-230, 231-260, 261-290, 291-320, 321-350, 351-380, 381-410, 411-440, 441-470, 471-500, 501-530, or 531 to the end of the coding region. Moreover, polypeptide fragments can be about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540 or 545 amino acids in length. In this context the term "about" includes the particularly recited ranges, larger or smaller by several amino acids, preferably by 5, 4, 3, 2, or 1 amino acids at either extreme, or at both extremes.

Preferred polypeptide fragments have a continuous series of deleted residues from the amino or the carboxy terminus, or both. For example, any number of amino acids, ranging from 1-30, 1-60, 1-90, 1-120, 1-150, 1-180, 1-210, 1-230, 1-250, 1-280, 1-310, 1-340, 1-370, 1-400, 1-430, 1-460, 1-490, 1-520, 1-545 can be deleted from the amino terminus of the YopM protein according to the invention as described herein above. Similarly, any number of amino acids ranging from 1-30, 1-60, 1-90, 1-120, 1-150, 1-180, 1-210, 1-230, 1-250, 1-280, 1-310, 1-340, 1-370, 1-400, 1-430, 1-460, 1-490, 1-520, 1-545 can be deleted from the carboxy terminus of the secreted protein or mature form. Furthermore, any combination of the above amino and carboxy terminus deletions is contemplated.

Further contemplated are YopM-polypeptide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, Leucine-rich regions, Leucine-rich repeats, Leucine-rich repeat regions, and high antigenic index regions. Furthermore, polypeptide fragments of YopM according to the present invention as described herein above falling within conserved domains are specifically contemplated by the present invention.

Polynucleotides encoding these fragments/domains are also contemplated.

In the context of the present invention the term "YopM fragment" includes that the fragment is a biologically active fragment. The term "biologically active" means that the fragment has the above mentioned biological activities of YopM, i.e, a fragment of the invention has the capability of autopenetrating the cell membrane and integrating into the cell cytosol without the requirement of additional factors. Further capabilities of "biologically active" fragments of the invention are discussed herein below.

*Yersinia* outer protein M or a fragment thereof, which differs from the *Yersinia* outer protein M or its fragment, but retains essential properties thereof, for example retains the capability of autopenetrating the cell membrane and integrating into the cell cytosol without the requirement of additional factors are also contemplated. Generally, such compounds can be overall closely similar, and it is envisaged that they are, in some or many regions, identical to the YopM of the present invention.

In the context of the present invention a "YopM variant" encompasses YopM polypeptide sequences as described herein, which comprise, or alternatively consist of, an amino acid sequence which is at least 40%, 50%, 60%, 70%, 80%, 90%, 91%, 92%, 93%, 94%, 95%, 96%, 97%, 98%, or 99% identical to the YopM polypeptide sequence as described herein, preferably to the YopM polypeptide identified as SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8 and/or polypeptide fragments of any of the polypeptides provided herein (e.g., those fragments described herein). Moreover, polynucleotides encoding these variants are also contemplated.

Preferably, a YopM polypeptide sequence being at least 40%, 50%, 60%, 70%, 80%, 90%, 91%, 92%, 93%, 94%, 95%, 96%, 97%, 98%, or 99% identical to the YopM polypeptide sequence as described herein, for example to the YopM polypeptide identified as SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8 and/or polypeptide fragments of any of the polypeptides provided herein, essentially retains the capability of autopenetrating the cell membrane and integrating into the cell cytosol without the requirement of additional factors.

Whether any particular polypeptide is at least 40%, 50%, 60%, 70%, 80%, 90%, 91%, 92%, 93%, 94%, 95%, 96%, 97%, 98%, or 99% identical to the YopM polypeptide sequence as described herein above can be determined by any means known to the person skilled in the art, e.g. by using conventionally known computer programs. A preferred method for determining the best overall match between a query sequence (a sequence of the present invention) and a subject sequence, also referred to as a global sequence alignment, can be determined using the CLUSTALW computer program (Thompson, J. D., et al., *Nucleic Acids Research*, 2 (22): 4673-4680, (1994)), which is based on the algorithm of Higgins, D. G., et al., *Computer Applications in the Biosciences* (CABIOS), 8 (2): 189-191, (1992). The result of said global sequence alignment is in percent identity. Preferred parameters used in a CLUSTALW alignment of protein sequences to calculate percent identity via pairwise alignments are: Matrix=Gonnet, k-tuple=1, Number of Top Diagonals=5, Gap Penalty=3, Gap Open Penalty 10, Gap Extension Penalty=0.1, Scoring Method=Percentage, Window Size=5 or the length of the subject polypeptide sequence, whichever is shorter. The pairwise and multiple alignment parameters provided for CLUSTALW above represent the default parameters as provided with the AlignX software program (Vector NTI suite of programs).

The present invention encompasses the application of a manual correction to the percent identity results, in the instance where the subject sequence is shorter than the query sequence because of N-terminal or C-terminal deletions, not because of internal deletions. If only the local pairwise percent identity is required, no manual correction is needed.

However, a manual correction may be applied to determine the global percent identity from a global polypeptide alignment. Percent identity calculations based upon global polypeptide alignments are often preferred since they reflect the percent identity between the polypeptide molecules as a whole (i.e., including any overhangs, not just overlapping regions), as opposed to, only local matching polypeptides. Manual corrections for global percent identity determinations are required since the CLUSTALW program does not account for N-terminal or C-terminal truncations of the subject sequence when calculating percent identity. For subject sequences truncated at the N-terminal or C-terminal ends, relative to the query sequence, the percent identity is corrected by calculating the number of amino acids of the query sequence that are N-terminal or C-terminal of the subject sequence, which are not matched/aligned, as a percent of the total amino acids of the query sequence. Whether an amino acid is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention.

In addition to the above method of aligning two or more polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modified CLUSTALW algorithm may provide a more accurate value of the percent identity for two polypeptide sequences. Support for such a modified version of CLUSTALW is provided within the CLUSTALW algorithm and would be readily appreciated to a person skilled in the art.

Polynucleotides encoding YopM variants according to the present invention may contain alterations in the coding regions, non-coding regions, or both. For example, the polynucleotides encoding YopM or YopM variants may contain alterations, which produce silent substitutions, additions, or deletions, but do not alter the properties or activities of the encoded polypeptide. Nucleotide variants produced by silent substitutions due to the degeneracy of the genetic code are preferred.

In the context of the present invention the term "YopM variant" also includes that the variant is a biologically active YopM molecule or a fragment thereof, preferably the term means that the fragment has biological activities of YopM. It is envisaged that a variant of the invention has the capability of autopenetrating the cell membrane and integrating into the cell cytosol without the requirement of additional factors as defined herein. It is also envisaged that a fragment/variant has the capability of autopenetrating the cell membrane and integrating into the cell cytosol without the requirement of additional factors, as can be tested in accordance with an assay as described herein above. Such variants may include deletions, insertions, inversions, repeats, and substitutions selected according to general rules known in the art so as to have little effect on activity. For example, guidance concerning how to make phenotypically silent amino acid substitutions is provided in Bowie et al., (*Science* 247: 1306-1310 (1990)), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) could be used (Cunningham and Wells, *Science* 244: 1081-1085 (1989)). The resulting mutant molecules can then be tested for biological activity. As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require non-polar side chains, whereas few features of surface side chains are generally conserved.

The invention encompasses YopM polypeptides having a lower degree of identity but having sufficient similarity so as to perform one or more of the same functions performed by the YopM as described herein above, preferably to retain the capability of autopenetrating the cell membrane and integrating into the cell cytosol without the requirement of additional factors. Similarity is determined by conserved amino acid substitution. Such substitutions are those that substitute a given amino acid in a polypeptide by another amino acid of like characteristics (e.g., chemical properties). According to Cunningham et al. above, such conservative substitutions are likely to be phenotypically silent. Additional guidance concerning which amino acid changes are likely to be phenotypically silent are found in Bowie et al., (*Science* 247: 1306-1310 (1990)). Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Aside from the canonical chemically conservative substitutions referenced above, the invention also encompasses substitutions which are typically not classified as conservative, but that may be chemically conservative under certain circumstances.

Besides conservative amino acid substitution, "YopM" "YopM fragments" and/or "YopM variants" of the present invention include, but are not limited to, the following: (i) substitutions with one or more of the non-conserved amino acid residues, where the substituted amino acid residues may or may not be one encoded by the genetic code, or (ii) substitutions with one or more of amino acid residues having a substituent group, or (iii) fusions of the polypeptide with another compound to increase the stability and/or solubility of the polypeptide (for example, polyethylene glycol), or (iv) fusions of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., *Clin. Exp. Immunol.* 2: 331-340 (1967); Robbins et al., *Diabetes* 36: 838-845 (1987); Cleland et al., *Crit. Rev. Therapeutic Drug Carrier Systems* 10: 307-377 (1993)). Moreover, the invention further includes polypeptide variants created through the application of molecular evolution ("DNA Shuffling") methodology to the YopM as described herein above. Such DNA Shuffling technology is known to the person skilled in the art and can derived, for example, from Stemmer, (*PNAS*, 91: 10747, (1994) or Leong et al. (*PNAS* 100: 1163-1168 (2003)).

In a specific embodiment the term "YopM variant" also refers to YopM polypeptides which are different from SEQ ID NO: 4, e.g. YopM polypeptides which are not derived from *Yersinia enterolitica* 8081v, serotype O:8.

The term "YopM", "YopM fragment", and/or "YopM variant" also includes YopM polypeptides which comprise non-classical amino acids including D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoroamino acids, designer amino acids such as β-methyl amino acids, Ca-methyl amino acids, Na-methyl amino acids, and amino acid analogs in general. Furthermore, the amino acid can be D (dextrorotary) or L (levorotary).

The term "YopM", "YopM fragment", and/or "YopM variant" also includes YopM polypeptides which are differentially modified during or after translation, e.g. by glycosylation, acetylation, phosphorylation, amidation, derivatization by known protecting/blocking groups, or proteolytic cleavage etc. Any of numerous chemical modifications may be carried out by known techniques, including but not limited to, specific chemical cleavage by cyanogen bromide, trypsin, chymotrypsin, papain, V8 protease, acetylation, formylation, oxidation, reduction; or metabolic synthesis in the presence of tunicamycin; etc.

Additional post-translational modifications encompassed by the invention include, for example N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression.

The "YopM", "YopM fragment", and/or "YopM variant" may also be modified with a detectable label, such as an enzymatic, fluorescent, isotopic or affinity label to allow for detection and isolation of the protein, the addition of epitope tagged peptide fragments (e.g., His, FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

The term "YopM", "YopM fragment", and/or "YopM variant" also encompasses chemically modified derivatives that may provide additional advantages such as increased solubility, stability, and circulating time of the polypeptide altogether increasing its half-life, or decreased immunogenicity (see U.S. Pat. No. 4,179,337). The chemical moieties for derivatization may be selected from water soluble polymers such as polyethylene glycol, ethylene glycol/propylene glycol copolymers, carboxymethyl cellulose, dextran, polyvinyl alcohol and the like. The polypeptides may be modified at random positions within the molecule, or at predetermined positions within the molecule and may include one, two, three or more attached chemical moieties. Preferably, a chemical derivatization is contemplated wherein the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethyl cellulose, alginic acid and salts thereof, such as sodium and calcium alginate, glycosaminoglycans and salts thereof, including salts of hyaluronic acid, phosphorylated and sulfonate derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). Additional preferred polymers, which may be used to derivatize the compounds of the invention, include, for example, poly (ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, are known to the person skilled in the art. Generally, the polymers used may include polymers that can be attached to the polypeptides of the invention via alkylation or acylation reactions.

The polyethylene glycol molecules (or other chemical moieties) should be attached to the compounds of the invention with consideration of effects on functional or antigenic domains of the protein. There are a number of attachment methods available to those skilled in the art, e.g derivable from EP 0 401 384. For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group. One may specifically desire proteins chemically modified at the N-terminus.

Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules.

Selective proteins chemically modified at the N-terminus modification may be accomplished by reductive alkylation that exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the compound of the invention in accordance with the present invention. Such functionalities include, for example, carboxyl, amine, hydroxy and thiol groups.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides that may be used for derivatization include saccharides that can be attached to the polypeptides of the invention via alkylation or acylation reactions.

Moreover, the invention also encompasses derivatization of the compounds of the invention, for example, with lipids (including cationic, anionic, polymerized, charged, synthetic, saturated, unsaturated, and any combination of the above, etc.) or stabilizing agents. Preferably, the present invention encompasses derivatization of YopM with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, polyalginates, and polylactide-coglycolide polymers. Exemplary semi-synthetic polymers include carboxymethylcellulose, hydroxymethyl-cellulose, hydroxypropylmethylcellulose, methylcellulose, and methoxycellulose. Exemplary synthetic polymers include polyphosphazenes, hydroxyapatites, fluoro-apatite polymers, polyethylenes (such as, for example, polyethylene glycol, polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethyl-methacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in U.S. Pat. No. 5,205,290. Moreover, the term "YopM variant" also relates to additional modifications of the YopM polypeptides of the present invention. Such additional modifications are known in the art, and are specifically provided, in addition to methods of derivatization, etc., in U.S. Pat. No. 6,028,066.

In a preferred embodiment of the invention the YopM fragment and/or YopM variant as described herein comprises at least one, i.e. one, two, three, four, five, six, seven, eight, nine, ten, or more of the alpha helices of YopM. The term "at least one of the alpha helices of YopM" relates to an alpha helical structure within the YopM polypeptide as described herein above, preferably of any one of SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, as can be determined according to methods known in the art. An alpha helical structure has been described for example in Evdokimov et al. (*J. Mol. Biol.* 312: 807-821 (2001)). The alpha helical structure may be in any orientation or order with respect to other structural elements in the polypeptide. The alpha helical structure may be N-terminally located or C-terminally located or may be localized at any other suitable position within the polypeptide or molecule. A sub-portion of YopM comprising amino acid positions 1 to 51 or 52 to 73 of SEQ ID NO: 4 is also contemplated. Preferably, such a YopM fragment or YopM variant has the capability of autopenetrating the cell membrane and integrating into the cell cytosol without the requirement of additional factors. As mentioned before, this capability can be tested in accordance with an assay as described herein above or otherwise.

Figure 4:
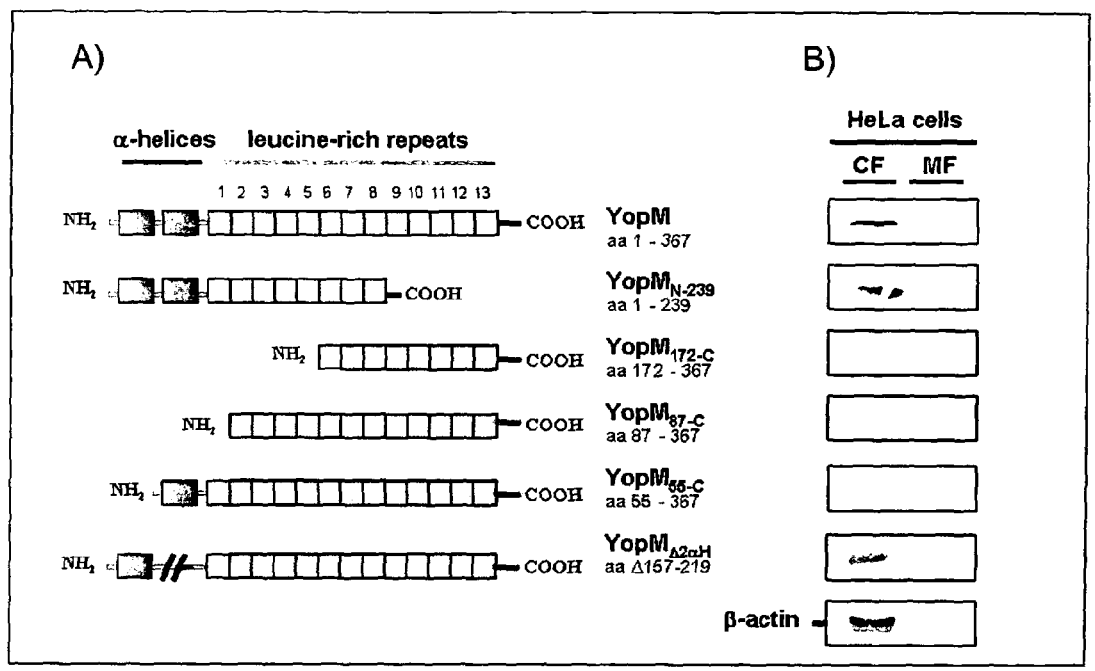

The appended examples clearly prove in this regard that at least one alpha helix of YopM is sufficient to mediate autopenetration of the cell membrane and integration into the cell cytosol without the requirement of additional factors (see for example FIG. 4).

In a further embodiment, a YopM fragment or YopM variant as described herein, comprises at least two of the alpha helices of YopM. The term "at least two of the alpha helices of YopM" relates to a combination of at least two, i.e. two, three, four, five, six, seven, eight, nine, ten, or more independent alpha helical structures within the YopM polypeptide as described herein above, preferably of any one of SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, as can be determined according to methods known in the art. Alpha helical structures are described for example in Evdokimov et al. (*J. Mol. Biol.* 312: 807-821 (2001)). The alpha helical structures may be in any orientation or order with respect to other structural elements in the polypeptide, including the duplication of one alpha helical structure and the presence of two different alpha helical structures in one polypeptide. The alpha helical structure may be N-terminally located or C-terminally located or may be localized at any other suitable position within the polypeptide or molecule.

A sub-portion of YopM comprising amino acid positions 1 to 51 and 52 to 73 of SEQ ID NO: 4 is also contemplated. In a further embodiment the sub-portion of YopM comprising amino acid positions 1 to 51 of SEQ ID NO: 4 may be duplicated or the sub-portion of YopM comprising amino acid positions 52 to 73 of SEQ ID NO: 4 may be duplicated. Furthermore, the sub-portions of YopM comprising amino acid positions 1 to 51 of SEQ ID NO: 4 and amino acid positions 52 to 73 of SEQ ID NO: 4 may be in any orientation or order. This means that amino acid positions 1 to 51 of SEQ ID NO: 4 may be N-terminally located or C-terminally located or may be localized at any other suitable position within a larger polypeptide or molecule structure. Furthermore, amino acid positions 52 to 73 of SEQ ID NO: 4 may be N-terminally located or C-terminally located or may be localized at any other suitable position within a larger polypeptide or molecule structure.

Preferably, such a YopM fragment or YopM variant has the capability of autopenetrating the cell membrane and integrating into the cell cytosol without the requirement of additional factors. This can be tested in accordance with an assay as described herein. The appended examples clearly prove in this regard that at least two alpha helices of YopM are sufficient to autopenetrate the cell membrane and integrate into the cell cytosol without the requirement of additional factors (see for example FIG. 11).

In a further embodiment, a YopM fragment or YopM variant comprising one or two of the alpha helices as described herein above may additionally comprise at least one YopM leucine-rich repeat. The term "at least one YopM leucine-rich repeat" relates to a leucine rich repeat as present in a YopM polypeptide as described herein above, preferably of any one of SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, as can be determined according to methods known in the art. Such leucine-rich repeats are described in Evdokimov et al. (*J. Mol. Biol.* 312: 807-821 (2001)). The leucine-rich repeat may be in any orientation or order with respect to a second or further leucine-rich repeat and/or with respect to one or two alpha helical structures as described herein above and/or with respect to other structural elements in the polypeptide. The leucine-rich repeat may be N-terminally located or C-terminally located or may be localized at any other suitable position within the polypeptide or molecule.

The term also encompasses a sub-portion of YopM comprising amino acid positions 74 to 93, 94 to 113, 114 to 133, 134 to 155, 156 to 175, 176 to 197, 198 to 217, 218 to 237, 238 to 257, 258 to 277, 278 to 297, 298 to 317, or 318 to 337, of SEQ ID NO: 4.

Preferably, such a YopM fragment or YopM variant has the capability of autopenetrating the cell membrane and integrating into the cell cytosol without the requirement of additional factors. This can be tested in accordance with an assay as described herein.

In a further embodiment, a YopM fragment or YopM variant comprising one or two of the alpha helices as described herein above may additionally comprise leucine-rich repeats 1-3 of YopM. The term "leucine-rich repeats 1-3 of YopM" relates to the first three N-terminal leucine rich repeats as present in a YopM polypeptide as described herein above, preferably of any one of SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8, as can be determined according to methods known in the art. Leucine rich repeats 1-3 of YopM are also described in Evdokimov et al. (*J. Mol. Biol.* 312: 807-821 (2001)). The leucine-rich repeats 1-3 may be in any orientation or order with respect to further leucine-rich repeats and/or with respect to one or two alpha helical structures as described herein above and/or with respect to other structural elements in the polypeptide. The leucine-rich repeats 1-3 may be N-terminally located or C-terminally located or may be localized at any other suitable position within the polypeptide or molecule.

A sub-portion of YopM comprising amino acid positions 74 to 133 of SEQ ID NO: 4 is contemplated as well.

Preferably, such a YopM fragment or YopM variant has the capability of autopenetrating the cell membrane and integrating into the cell cytosol without the requirement of additional factors. This can be tested in accordance with an assay as described herein.

In a further preferred embodiment the YopM fragment comprises any amino acid sequence selected from amino acids 1 to 239 of SEQ ID NO: 4, amino acids 55 to 367 of SEQ ID NO: 4, amino acids 1 to 73 of SEQ ID NO: 4, amino acids 52 to 73 of SEQ ID NO: 4, amino acids 1 to 133 of SEQ ID NO: 4 and amino acids 52 to 133 of SEQ ID NO: 4. Furthermore, the YopM fragment may comprise amino acids 1 to 51 and at the same time, i.e. on the same polypeptide, amino acids 74 to 133 of SEQ ID NO: 4. In this case amino acids 1 to 51 and 74 to 133 of SEQ ID NO:4 may be fused directly or a spacer of 1, 2, 3, 4, 5, 7, 8, 9, 10, 11, 12, 13, 14, 15 or 16 to 50 amino acids may be located between the amino acid sequences. The amino acid sequences as described above may be in any orientation or order with respect to other structural elements in the polypeptide. The amino acid sequences may be N-terminally located or C-terminally located or may be localized at any other suitable position within the polypeptide or molecule.

Preferably, such a YopM fragment has the capability of autopenetrating the cell membrane and integrating into the cell cytosol without the requirement of additional factors. This can be tested in accordance with an assay as described herein.

To analyze and localize domains within YopM that mediate immunomodulation, the truncated versions of YopM previously described (see Example 2), were used to treat differentiated HL60 cells. Besides the control protein YopM$_{87-C}$, only those versions of YopM were used, that are all still able to penetrate host cell membranes (see Example 2), because we presumed that the autopenetration ability is required for immunomodulation. While the control protein YopM$_{87-C}$, which does not autopenetrate cells, was not able to reduce transcription of TNFα, the autopenetrating versions, YopM$_{N-239}$, and YopM$_{55-C}$, were still able to reduce transcription of the TNFα (see FIG. 11). These results exclude a role of the C-terminus and the first amino-terminal helix of YopM in immunomodulation. The fact that the fusion protein 2αH-GFP containing both α-helices of YopM, was no longer able to reduce transcription of TNFα (FIG. 11) indicates that the LRRs 1-8 of YopM harbour the potential immunomodulatory domain. Furthermore, this result excludes a role of the amino-terminal α-helices of YopM in immunomodulation.

In a particularly preferred embodiment, the compounds of the invention have the capability of autopenetrating the cell membrane and integrating into the cell cytosol without the requirement of additional factors but at the same time have essentially no immunomodulatory capability, i.e. they do not comprise an immunomodulatory domain (particularly leucine-rich repeats) and/or the immunomodulatory domain is inactivated (for example by way of mutation like deletion, insertion etc. or otherwise). "Essentially no immunomodulatory capability" means that the compounds of the invention downregulate one or more cytokines, like for example TNFα (preferably the mRNA thereof), not more than about 5%, 10%, 15%, 20%, 25%, 30%, 40%, or 50% when compared to a negative control like for example medium per se and/or $YopM_{87-C}$. The term "cytokines" and "downregulate" is further explained herein below. Assays to determine the downregulation of a cytokine mRNA are likewise explained in more detail herein below.

YopM polypeptides, fragments, or variants of the invention can be produced recombinantly by any suitable method known to the person skilled in the art. The present invention, thus, also encompasses methods for the production of YopM polypeptides, or variants, or fragments, or immunmodulatory domains of YopM. Accordingly, the present invention contemplates polynucleotides encoding YopM polypeptides, fragments, or variants, or immunmodulatory domains of YopM of the present invention, and vectors containing said polynucleotides, host cells comprising those polynucleotides and/or vectors, and the production of YopM polypeptides, fragments or variants by recombinant techniques. A suitable vector may be, for example, a phage, plasmid, viral, or retroviral vector. Retroviral vectors may be replication-competent or replication-defective. In the latter case, viral propagation generally will occur only in complementing host cells.

Polynucleotides encoding YopM polypeptides, fragments or variants may be joined to a vector containing a selectable marker for propagation in a host.

As indicated, the expression vectors will preferably include at least one selectable marker. Such markers include, for instance, dihydrofolate reductase, G418, or neomycin resistance for eukaryotic cell culture and tetracycline, kanamycin, or ampicillin resistance genes for culturing in *E. coli* and other bacteria.

Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris*); insect cells such as *Drosophila melanogaster* S2 and *Spodoptera frugiperda* Sf9 cells; animal cells such as CHO, COS, HEK 293, and Bowes melanoma cells; and plant cells. Appropriate culture mediums and conditions for the above described host cells are known in the art.

Vectors preferred for use in bacteria are known to the person skilled in the art.

Introduction of the construct into the host cell can be effected by methods described in many standard laboratory manuals, such as Davis et al., (*Basic Methods In Molecular Biology* (1986)).

A YopM polypeptide, fragment, or variant in accordance with the present invention can be recovered and purified from recombinant cell cultures by any suitable method known to the person skilled in the art.

YopM polypeptides, fragments or variants in accordance with the present invention can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells.

In a specific embodiment, the yeast *Pichia pastoris* is used to express the compounds of the present invention In addition, YopM polypeptides, fragments, variants, or immunomodulatory domains of YopM of the invention can be chemically synthesized using techniques known in the art (Creighton, 1983, *Proteins: Structures and Molecular Principles*, W.H. Freeman & Co., N.Y., and Hunkapiller et al., *Nature*, 310: 105-111 (1984)). For example, a polypeptide corresponding to a fragment of a polypeptide sequence of the invention can be synthesized by use of a peptide synthesizer.

The analysis of the T3SS-independent autopenetration of YopM into the host cell cytoplasm implicates the N-terminal α-helices of the protein as being involved in autopenetration. In analogy to previous studies with CPPs, it was investigated whether a cellular delivery of whole proteins might be possible by using the N-terminal α-helices of the YopM protein as cargo transporters. To this end GFP was used as a model protein to confirm that the N-terminal α-helices of YopM can indeed mediate the transduction of a foreign protein into eukaryotic cells. A corresponding construct was generated comprising both α-helices fused to GFP. To construct a vector for the expression of a 2αH-GFP fusion protein, an inverse PCR with pET-yopM as template was performed, resulting in the vector pET-2αH harbouring only the coding regions for the amino-terminal helices of YopM. The gene for gfp was amplified by PCR and inserted into the pET-2αH vector for protein expression. Proteins were isolated, purified and concentrated via carboxy-terminal 6×His tag by affinity chromatography. To investigate whether the resulting fusion protein 2αH-GFP can autopenetrate the membranes of the host cells, HeLa cells were incubated with recombinant proteins 2αH-GFP and GFP for 30 min at 37° C. and analyzed by fluorescence microscopy (FIG. 5A) and Western blotting (FIG. 5B). In contrast to GFP, which alone is not able to enter the host cell cytoplasm, the fusion protein 2αH-GFP can penetrate the host cell membrane and accumulates inside the host cell cytoplasm, as shown by Western blotting analysis after cell fractionation of GFP- and 2αH-GFP-treated HeLa cells (FIG. 5B). Furthermore, the fluorescence microscopy images show that the fusion protein is localized in the cytoplasm and seems to appear in vesicle-like structures inside the cytosol (FIG. 5A: a, b, c). This cannot be observed in GFP-treated HeLa cells (FIG. 5A: d, e, f). Interestingly, after "pulse-chase" treatment of HeLa cells with 2αH-GFP at 4° C. (leading to an accumulation of the protein at the plasma membrane of target cells caused by inhibition of the energy dependent uptake mechanism), the mentioned vesicle-like structures containing 2αH-GFP shift more towards the cell center and finally concentrate in the perinuclear region, but do not appear inside the nucleus (FIG. 5A: d, e, f). This indicates that the fusion protein 2αH-GFP after autopenetration of the cytoplasmic membrane follows the same intracellular route as recombinant YopM. This observation suggests that the amino-terminal helices of YopM might encode the information for intracellular transport. This conclusion is nicely underlined by co-localization experiments after "pulse-chase" treatment of HeLa cells with 2αH-GFP and YopM (FIG. 6). While recombinant YopM also appears in vesicle-like structures after penetration of host cell membranes (FIG. 6: a, b, c), both proteins co-localize in these vesicle-like structures during combined incubation of HeLa cells with YopM and 2αH-GFP (FIG. 6: d, e, f, g). Together these results demonstrate that the N-terminal α-helices of YopM can deliver cargo proteins into the cytoplasm of target cells and thus represent CPP motifs that might be used as new tools to deliver cargos into eukaryotic cells as had already been described for other CPPs.

It follows that in the context of the present invention, YopM, a YopM fragment, or a YopM variant as described herein may be used for delivering a cargo molecule across the membrane to the cytosol of a cell.

In a preferred embodiment YopM, a YopM fragment, or a YopM variant as described herein is linked to a cargo molecule. The term "linked to a cargo molecule" means that the cargo molecule may be connected by any means known to the person skilled in the art to the compounds of the invention (for example covalently, non-covalently etc.). It is envisaged that structures on the surface of the cargo molecule like functional or reactive chemical groups are used to establish a linkage or binding between YopM, a YopM fragment, a YopM variant, or a immunomodulatory domain of YopM, and a cargo molecule. "Linked to" also includes that the compounds of the invention and the cargo molecules are expressed/expressable on/from a single nucleic acid as a single continuous region. Fusion proteins consisting of a proteinaceous cargo (polypeptides, antibodies etc.) and the compound(s) of the invention are likewise contemplated. Nucleic acids encoding these fusion proteins, vectors comprising these nucleic acids and pharmaceutical compositions comprising these vectors or nucleic acids are likewise contemplated.

The compounds of the present invention may be linked to a cargo by any method known to the person skilled in the art, e.g. by chemical cross-linking, an avidin bridge, a glutation-S-transferase bridge, a linkage comprising at least one, at least two or at least three disulfide bonds or at least one peptide bond or at least two peptide bonds. Various functional groups, such as hydroxyl, amino or halogen groups present on the cargo may be used as a handle to attach a suitable complexing group. For example, a hydroxyl group may be modified to include an acidic phosphate group. It is also envisaged that the linkage includes a disulfide bond. The linkage may also include a streptavidin-biotin complex. It is envisaged that the delivery peptide, i.e. YopM, a YopM fragment, or a YopM variant is biotinylated and the cargo molecule is avidin labeled. Thus, "linked to" also includes a non-covalent linkage/association of cargo molecules with the compounds of the invention.

The linkage between the delivery peptide and the cargo may also be achieved by a peptide bond. Examples including those peptide bonds or linkers are described for example in U.S. Pat. No. 5,073,627.

In a preferred embodiment, the cargo is linked via a peptide bond in the form of a protein-protein fusion. In such a protein-protein fusion, the cargo may be separated from the compounds of the invention by an amino acid linker (spacer). Such a linker is preferably of the size of 1, 2, 3, 4, 5, 6, 7, 8, 9, 10, 11, 12, 13, 14, 15 or 16 to 50 amino acids or of any other suitable size known to the person skilled in the art. The linker may consist of any suitable amino acid known to the person skilled in the art. Preferably, a linker comprising the amino acid glycine is used. The linker is not restricted to amino acids but may also comprise other entities/molecules, for example such as poly('hydroxy'methylene) groups.

In a further preferred embodiment, the protein-protein fusion may be in the form of a transcriptional fusion. Suitable transcriptional fusions, as well as suitable methods to generate corresponding constructs, are known to the person skilled in the art.

Furthermore, the compounds of the invention may be linked to a cargo by a cleavable linker.

It is envisaged that the cargo is modified using a number of methods known in the art, either directly, e.g. with a carbodiimide, or via at least one linking moiety. In particular, carbamate, ester, thioether, disulfide, and hydrazone linkages may be formed. Ester and disulfide linkages are envisaged, if the linkage is to be readily degraded in the cytosol, after transport of the cargo across the cell membrane.

In a further embodiment YopM, a YopM fragment, or a YopM variant as described herein above is linked to a cargo via a linkage at the C-terminus or the N-terminus of the compounds of the invention. Preferably, such a linkage at the C-terminus or the N-terminus is a peptide bond, more preferably said linkage is a protein-protein fusion including, for instance, the presence of a spacer or linker of the size of 1, 2, 3, 4, 5, 6, 7, 8, 9, 10, 11, 12, 13, 14, 15 or 16 to 50 amino acids or of any other suitable size known to the person skilled in the art. The linker may consist of any suitable amino acid known to the person skilled in the art. Preferably, a linker comprising the amino acid glycine is used.

In a further embodiment, the compound of the invention is biotinylated and the cargo molecule is avidin labeled or vice versa.

The term "cargo" or "cargo molecule", as used herein, refers to any entity (e.g. a small molecule, macromolecule or macromolecular complex), which may be delivered/transferred/is transferable across the membrane of a cell or into the cytosol of a target cell. It is envisaged that a "cargo" or "cargo molecule" is transferable/transferred or delivered across the membrane of a cell or into the cytosol of a target cell, if it is detected/detectable in the cytoplasmic fraction—either associated with vesicles and/or already released into the cytosol, the latter being preferred. The cytoplasmic fraction denotes the interior of a cell.

It is preferred but not exclusive that the "cargo" is heterologous to *Yersinia*. By the term "heterologous" as used herein is meant that it does not come from, is not normally/naturally produced by and/or required for viability of *Yersinia*. It is also preferred that the cargo is not a Yop translocator and likewise not a component of a type III secretion system.

It is particularly preferred that the cargo exerts a beneficial effect in a medical context, i.e. the cargo displays therapeutical and/or diagnostic activity/capabilities, following delivery into the cells, ex vivo and/or in vivo. "Therapeutic activitiy" includes treatment, amelioration and/or prophylaxis of a disease. "Diagnostic activity" includes visualizing, detecting, distinguishing and/or identifying a pathological/medical condition and attributing the deviation to a clinical picture.

Preferably, the term "cargo" includes, but is in no way limited to, a nucleic acid, a polypeptide, an antibody or a functional fragment thereof, an organic molecule, a small organic molecule, a metal, a nano-particle, a virus, a modified virus, a viral vector, a plasmid, etc.

This invention is generally applicable for therapeutic, prophylactic, or diagnostic intracellular delivery of small molecules and of macromolecules, such as proteins, nucleic acids, and/or polysaccharides, that are not inherently capable of entering target cells at a useful rate. It should be appreciated, however, that alternate embodiments of this invention are not limited to clinical applications. This invention may be advantageously applied in medical and biological research. In research applications of this invention, the cargo may be e.g. a drug or a reporter molecule.

The term "nucleic acid" in the context of the cargo molecules refers to any nucleic acid known to the person skilled in the art, e.g. a polynucleotide like DNA, RNA, single stranded DNA, cDNA, or derivatives thereof. Preferably the term refers to oligonucleotides and polynucleotides formed of DNA and RNA, and analogs thereof, which have selected sequences designed for hybridisation to complementary targets, such as antisense sequences for single- or double-stranded targets, or for expressing nucleic acid transcripts or proteins encoded by the sequences. Analogs include charged and preferably uncharged backbone analogs, such as phosphonates, methyl phosphonates, phosphoramidates, preferably N-3' or N-5', thiophosphates, uncharged morpholino-based polymers, and protein nucleic acids (PNAs). Such molecules can be used in a variety of therapeutic regimens, including enzyme replacement therapy, gene therapy, and antisense therapy, for example. Furthermore, the term refers to ribosome, or antisense RNA. The protein, RNA or ribosome encoded by the nucleic acid may be under-represented, defunct or non-existent in the cell and the antisense RNA encoded by the nucleic acid may allow for the elimination of an undesired function of a molecule. In a preferred embodiment YopM, a YopM fragment, or a YopM variant as described herein above may be synthesised as a fusion with a peptide nucleic acid (PNA), which is a DNA-mimic capable of forming double and triple helices with DNA. Such peptide-PNA fusion can form a stable DNA or RNA/PNA duplex, which may enter cells via the YopM component of the present invention, thereby delivering the DNA or RNA to a target cell.

By way of example, protein nucleic acids (PNA) are analogs of DNA in which the backbone is structurally homomorphous with a deoxyribose backbone. The backbone consists of N-(2-aminoethyl)glycine units to which the nucleobases are attached. PNAs containing all four natural nucleobases hybridise to complementary oligonucleotides obeying Watson-Crick base-pairing rules, and are a true DNA-mimic in terms of base pair recognition (Egholm et al. *Nature* 365:566-568 (1993)). The backbone of a PNA is formed by peptide bonds rather than phosphate esters, making it well-suited for anti-sense applications. Since the backbone is uncharged, PNA/DNA or PNA/RNA duplexes that form exhibit greater than normal thermal stability. PNAs have the additional advantage that they are not recognized by nucleases or proteases. In addition, PNAs can be synthesized on an automated peptides synthesizer using standard t-Boc chemistry. The PNA is then readily linked to a transport polymer of the invention.

In another preferred embodiment YopM, a YopM fragment, or a YopM variant is combined with decoy oligonucleotides, which preferably contain specific binding sites for transcription factors and may block the function of the transcription factors in vitro and in vivo.

The term "polypeptide" in the context of the cargo molecules refers to any polypeptide known to the person skilled in the art including therapeutically active proteins known to the person skilled in the art, enzymes, marker proteins like EGFP or luciferin. In a preferred embodiment the term relates to *Yersinia* outer protein P (YopP). Accordingly, YopP may be linked to YopM, a YopM fragment or a YopM variant and thereby transported as a cargo molecule across the cell membrane into the cytosol of a host cell. Preferably, the linkage is a peptide linkage as described herein above. In another embodiment the term "polypeptide" in the context of the cargo molecules relates to fusion proteins between YopM, a YopM fragment, or a YopM variant and a second protein that is used as a cargo, preferably a heterologous protein, which may lead, for example, to chimeric proteins having more than one function. In a further preferred embodiment the protein-protein fusion may be in the form of a transcriptional fusion. A suitable transcriptional fusion, as well as a suitable method to generate corresponding constructs, are known to the person skilled in the art.

The term "antibody" in the context of the cargo molecules refers to a monoclonal or a polyclonal antibody (see Harlow and Lane, "*Antibodies, A Laboratory Manual*", CSH Press, Cold Spring Harbor, USA, 1988) or a derivative of said antibody which retains or essentially retains its binding specificity. Preferred derivatives of such antibodies are chimeric antibodies comprising, for example, a mouse or rat variable region and a human constant region. The term "functional fragment" as used herein refers to fragments of the antibodies as specified herein which retain or essentially retain the binding specificity of the antibodies like, separated light and heavy chains, Fab, Fab/c, Fv, Fab', F(ab')2. The term "antibody" also comprises bifunctional (bispecific) antibodies and antibody constructs, like single-chain Fvs (scFv) or antibody-fusion proteins. The term "scFv fragment" (single-chain Fv fragment) is well understood in the art and preferred due to its small size and the possibility to produce such fragments recombinantly. Said antibody or antibody binding portion is a human antibody or a humanized antibody. The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A1 0 239 400 and WO90/07861.

The term "organic molecule" and "small organic molecule" in the context of the cargo molecules relates to organic molecules which are therapeutically useful and preferably include drugs or other biologically or therapeutically active agents, which act to ensure proper functioning of a cell or molecules which may induce, for instance, apoptosis or cell lysis, where death of a cell, such as a cancerous cell, is desired. Preferably, a small organic molecule has poor solubilities in aqueous liquids, such as serum and aqueous saline. Thus, compounds whose therapeutic efficacies are limited by their low solubilities can be administered in greater dosages according to the present invention, and can be more efficacious on a molar basis in combined form, relative to the non-combined form, due to higher uptake levels by cells. Exemplary of such small organic molecules that form preferred compositions according to the present invention are taxanes. Taxanes and taxoids are believed to manifest their anticancer effects by promoting polymerisation of microtubules (and inhibiting depolymerisation) to an extent that is deleterious to cell function, inhibiting cell replication and ultimately leading to cell death. As used herein, the term "taxane" refers to paclitaxel and naturally occurring, synthetic, or bioengineered analogs. Preferably, the delivery peptide is combined with a modified taxane or taxoid, which has been modified to include an acid moiety, e.g. phosphate.

The term "nano-particle" in the context of the cargo molecules refers to a small particle with at least one dimension less than 400 nm, or any other suitable form and size known to the person skilled in the art, e.g. from Langel, Ü. (ed) (*Handbook of cell-penetrating peptides*, CRC Press, Boca Raton, Fla., 2007), and Langel, Ü. (ed) (*Cell-penetrating peptides: Processes and Applications*, CRC Press, Boca Raton, Fla. 2002). More preferably the term relates to such particles with at least one dimension less than 300 nm, even more preferably less than 200 nm, less than 100 nm, less than 50 nm, less than 30 nm, less than 20, less than 10 nm and most preferably less than 5 nm or less than 3 nm. In a preferred embodiment the term "nano-particle" refers to gold particles, e.g. of a minimal size of 2.8 nm, quantum dot loaded polymeric micelles, e.g of a minimal size of 20 nm, or to sterically stabilized liposomes of a minimal size of 65-200 nm.

The term "virus" in the context of the cargo molecules relates to any type of virus known to the person skilled in the art. Preferably, a virus is selected from the group consisting of adenoviruses, adeno-associated viruses, herpes viruses, simplex virus, lentiviruses and retroviruses.

The term "modified virus" in the context of the cargo molecules relates to a virus molecule, which has been altered in comparison to a wildtype virus. Such a modification may lead to increased or decreased vitality or have influence on binding or interaction capabilities of the virus, as the person skilled in the art would know.

The term "viral vector" in the context of the cargo molecules refers to genetic elements derived from viruses, which are modified in such a way as to minimize the risk of handling them. Preferably, the term relates to any such element known to the person skilled in the art. Typically, in viral vectors a part of the viral genome critical for viral replication has been deleted. Preferably, such a virus can efficiently infect cells but, once the infection has taken place, requires a helper virus to provide the missing proteins for production of new virions. Furthermore, viral vectors show a low toxicity and are genetically stable and do not rearrange their genomes. More preferably, the term relates to viral genetic elements in accordance with the above definition derived from adenoviruses, adeno-associated viruses, lentiviruses and retroviruses.

The term "metal" refers to any metal known to the person skilled in the art. Preferably, the term relates gold, platinum, lanthanide metals and actinides metals. In a further preferred embodiment the term relates to radioactive metals.

The term "plasmid" in the context of the cargo molecules refers to any extrachromosomal DNA molecule separate from the chromosomal DNA and capable of autonomous replication. Preferably, the term relates to any such molecule known to the person skilled in the art. More preferably, the term relates to a DNA molecule which is capable of autonomous replication in eukaryotic cells and which encodes a polypeptide of interest, e.g. a therapeutic protein.

In a preferred embodiment of the present invention, the cargo comprises at least one compound selected from the group consisting of therapeutic proteins, suicide proteins, tumor suppressor proteins, transcription factors, kinase inhibitors, kinases, regulatory proteins, apoptotic proteins, anti-apoptotic proteins, microbial antigens, viral antigens, bacterial antigens, parasitic antigens, cellular antigens, differentiation factors, immortalisation factors, toxines, enyzmes, antisense constructs, diagnostic imaging or contrast agents, isotopes, dyes, antibacterial agents, antifungal agents, antiviral agents, antiproliferative agents, cytostatics, immunosuppressive agents, histamine receptor antagonists, vitamins, analgesic agents, anti-neoplastic agents, hormones, antiinflammatory agents, adhesion-molecules, receptor-molecules, therapeutic organic molecules, organic inhibitors, peptide inhibitors and antiaging agents.

Furthermore, the cargo is essentially any biologically active agent or diagnostic molecule. The biologically active agent may be used in an unmodified form or it may be modified to incorporate a charged (typically acidic) residue to enhance the YopM-cargo complex. The term "biologically active agent" as used herein includes agents in their unmodified form as well as agents that have been modified, for example prodrugs, and have reduced or augmented levels of activity and/or reduced or augmented binding kinetics compared with the parent agent.

Given as a further example, highly charged agents, such as levodopa (L-3,4-dihydroxy-phenylalanine; L-DOPA) may be combined as cargo with the delivery protein of the invention, i.e with YopM, a YopM fragment, or a YopM variant. Furthermore, peptoid and peptidomimetic agents are also contemplated as cargo.

The term "therapeutic protein" in the context of the cargo molecules relates to any protein, which has a therapeutic effect on the animal body, in particular on the human body. Preferably, the term relates to any such protein known to the person skilled in the art. More preferably, the term relates to therapeutic enzymes like alglucerase, which may be used in treating lysosomal glucocerebrosidase deficiency (Gaucher's disease), alpha-L-iduronidase, which may be used in treating mucopolysaccharidosis I, alpha-N-acetylglucosamidase, which may be used in treating sanfilippo B syndrome, lipase, which may be used in treating pancreatic insufficiency, adenosine deaminase, which may be used in treating severe combined immunodeficiency syndrome, or triose phosphate isomerase, which may be used in treating neuromuscular dysfunction associated with triose phosphate isomerase deficiency.

The term "suicide proteins" in the context of the cargo molecules relates to any protein, which leads to the destruction of a cell due to the action of the protein, typically due to an enzymatic reaction in the presence of a corresponding substrate. Preferably, the term relates to any such protein known to the person skilled in the art. More preferably, the term relates to nucleoside kinases, such as the HSV-1 TK or multisubstrate deoxyribonucleoside kinase of Dm-dNK.

The term "tumor suppressor proteins" in the context of the cargo molecules relates to any protein, which protects a cell from one step on the path to cancer. Preferably, the term relates to any such protein known to the person skilled in the art. More preferably, the term relates to Rb protein, the p53 tumor suppressor, APC and CD95.

The term "transcription factors" in the context of the cargo molecules relates to any protein, which binds to specific parts of DNA using DNA binding domains and is part of the system that controls the transcription of genetic information from DNA to RNA. Preferably, the term relates to any such factor known to the person skilled in the art. More preferably, the term relates to TFIIA, TFIIB, TFIID, TFIIE, TFIIF, TFIIH and TATA binding protein (TBP).

The term "kinase inhibitors" in the context of the cargo molecules relates to any protein, which is a type of enzyme inhibitor that specifically blocks the action of protein kinase. Preferably, the term relates to any such factor known to the person skilled in the art. More preferably, the term relates to desatinib, Erbitux (cetuximab), Tarceva (Erlotinib), Iressa (gefitinib), and herceptin.

The term "kinase" in the context of the cargo molecules relates to any protein, which transfers phosphate groups from high-energy donor molecules, such as ATP, to specific target molecules. Preferably, the term relates to any such protein known to the person skilled in the art. More preferably, the term relates to tyrosine kinase or MAP kinase, MEK1, or MEK2.

The term "apoptotic protein" in the context of the cargo molecules relates to any protein, which leads to programmed cell death in multicellular organisms. Preferably, the term relates to any such protein known to the person skilled in the art. More preferably, the term relates to the pro-apoptotic protein BAX, BID, BAK, or BAD.

The term "anti-apoptotic protein" in the context of the cargo molecules relates to any protein, which impedes programmed cell death in multicellular organisms. Preferably, the term relates to any such protein known to the person skilled in the art. More preferably, the term relates to the anti-apoptotic protein like Bcl-XI, Bcl-2, and further members of the Bcl-2 family.

The terms "microbial antigens", "viral antigens", "bacterial antigens", parasitic antigens", and "cellular antigens" in the context of the cargo molecules relate to immunogens, which are able to stimulate an immune response derived from microbes, viruses, bacteria, parasites, or cells, respectively. Preferably, the term relates to any such immunogens known to the person skilled in the art. More preferably, the term relates to tumor-associated antigens (TAAs) or bacterial, viral, and parasitic surface proteins or glycoproteins.

The term "differentiation factor" in the context of the cargo molecules relates to any factor, which functions predominantly in development and leads to the differentiation of tissues, cell groups of specific cells. Preferably, the term relates to any such factor known to the person skilled in the art. More preferably, the term relates to growth differentiation factors (GDFs) like GDF1, GDF2, GDF3, GDF5, GDF6, GDF8, GDF9, GDF10, GDF11, and GDF15.

The term "immortalisation factors" in the context of the cargo molecules relates to any factor, which provoces an absence of a sustained increase in the rate of mortality of a cell as a function of chronological age. Preferably, the term relates to any such factor known to the person skilled in the art. More preferably, the term relates to telomerase or large T-antigen.

The term "toxin" in the context of the cargo molecules relates to any molecule, which is capable of causing disease or cell death on contact or absorption with body tissues by interacting with biological macromolecules such as enzymes or cellular receptors. Preferably, the term relates to any such factor known to the person skilled in the art. More preferably, the term relates to botulinum toxins, tetanus toxin, pertussis toxin, heat stable and heat labile *E. coli* entertoxin, Cholera toxin, Shiga toxin, cytolethal distending toxin, tracheal cytotoxin, diphtheria toxin, clostridial toxins, tetrodotoxin, batrachotoxin, maurotoxin, agitoxin, charybdotoxin, margatoxin, slotoxin, scyllatoxin, calciseptine, taicatoxin, and calcicludine. Most preferably, the term relates to bacterial toxins included in, but not limited to, the table on page 225 in Schmitt et al., (*Emerg. Infect. Dis.* 5: 224-234 (1999)).

The term "diagnostic imaging or contrast agent" in the context of the cargo molecules relates to any compound, which allows a visualization of molecular and cellular processes on either a macro- or microscopic level. Preferably, the term relates to any such compound known to the person skilled in the art. More preferably, the term relates to radioactive substances such as mTc glucoheptonate, or substances used in magnetic resonance imaging (MRI) procedures such as gadolinium doped chelation agents, e.g. Gd-DTPA, marker genes that encode proteins that are readily detectable when expressed in a cell including, but not limited to, beta-galactosidase, green fluorescent protein, luciferase as well as heavy metals, halogens, radionuclides, fluors, enzymes, enzyme substrates, enzyme cofactors, enzyme inhibitors, ligands, and haptens.

The term "isotope" in the context of the cargo molecules relates to elements having different atomic masses. Preferably, the term relates to any such factor known to the person skilled in the art. More preferably, the term relates to radioactive isotopes like N-15, C-13, P-31, F-19, or I-131.

The term "dye" in the context of the cargo molecules relates to colored substances that have an affinity to the substrate to which they are being applied. Preferably, the term relates to any such factor known to the person skilled in the art. More preferably, the term relates to colored substances used for molecular use like rhodamine, Cy2, Cy3, Cy5, Cy7, Texas Red, R-Phycoerythrin, PerCP, Pacific Blue, APC, Alexa 405, 430, 488, 546, 559, 594, 633, 660, 674, 680, 700, Cascade Blue, or fluorescein.

The term "antibacterial agent" in the context of the cargo molecules relates to any compound, which has a growth inhibition or growth restriction activity on bacteria. Preferably, the term relates to any such compound known to the person skilled in the art, e.g. [beta]-lactam antibiotics or quinolone antibiotics. More preferably, the term relates an agent selected from the group consisting of nafcillin, oxacillin, penicillin, amoxacillin, ampicillin, cephalosporine, cefotaxime, ceftriaxone, rifampin, minocycline, ciprofloxacin, norfloxacin, erythromycin, tetracycline, gentamicin, a macrolide, a quinolone, a [beta]-lactone, a P-lactamase inhibitor, salicylamide, and vancomycin, sulfanilamide, sulfamethoxazole, sulfacetamide, sulfisoxazole, sulfadiazine, penicillins such as penicillins G and V, methicillin, oxacillin, naficillin, ampicillin, amoxacillin, carbenicillin, ticarcillin, mezlocillin and piperacillin, cephalosporins such as cephalothin, cefaxolin, cephalexin, cefadroxil, cefamandole, cefoxitin, cefaclor, cefuroxine, loracarbef, cefonicid, cefotetan, ceforanide, cefotaxime, cefpodoxime, proxetil, ceftizoxime, cefoperazone, ceftazidime and cefepime, aminoglycosides such as gentamycin, tobramycin, amikacin, netilmicin, neomycin, kanamycin, streptomycin, and the like, tetracyclines such as chlortetracycline, oxytetracycline, demeclocycline, methacycline, doxycycline and minocycline, and macrolides such as erythromycin, clarithromycin, and azithromycin or analogs thereof.

The term "antifungal agent" in the context of the cargo molecules relates to any compound, which has a growth inhibition or growth restriction activity on fungal species. Preferably, the term relates to any such compound known to the person skilled in the art. More preferably, the term relates to amphotericin, itraconazole, ketoconazole, miconazole, nystatin, clotrimazole, fluconazole, ciclopirox, econazole, naftifine, terbinafine, and griseofulvin.

The term "antiviral agent" in the context of the cargo molecules relates to any compound that has a growth inhibition or growth restriction activity on viral species. Preferably, the term relates to any such compound known to the person skilled in the art. More preferably, the term relates to aciclovir, famciclovir, ganciclovir, foscarnet, idoxuridine, sorivudine, trifluridine (trifluoropyridine), valacyclovir, cidofovir, didanosine, stavudine, zalcitabine, zidovudine, ribavirin, and rimantatine.

The term "antiproliferative agent" in the context of the cargo molecules relates to any compound, which inhibits or restricts the cell proliferation. Preferably, the term relates to any such compound known to the person skilled in the art. More preferably, the term relates to methotrexate, azathioprine, fluorouracil, hydroxyurea, 6-thioguanine, cyclophosphamide, mechloroethamine hydrochloride, carmustine, cyclosporine, taxol, tacrolimus, vinblastine, dapsone, nedocromil, cromolyn (cromoglycic acid), and sulfasalazine.

The term "immunosuppressive agent" in the context of the cargo molecules relates to any compound, which leads to the inhibition or prevention of the activity of the immune system. Preferably, the term relates to any such compound known to the person skilled in the art. More preferably, the term relates to glucocorticoids, cytostatics, drugs acting on immunophilins or TNF-binding proteins. Most preferably, the term relates to cyclophosphamide, anthracycline, mitomycin C, bleomycin, mithramycin, azathioprine, mercaptopurine, methotrexate, cyclosporin, an anti IL-2 receptor antibody, an anti-OKT3 antibody and an anti-CD3 antibody, and TNF-α binding monoclonal antibodies such as infliximab (Remicade®), etanercept (Enbrel®), or adalimumab (Humira®).

The term "histamine receptor antagonist" in the context of the cargo molecules relates to any compound, which serves to inhibit the release or action of histamine. Preferably, the term relates to any such compound known to the person skilled in the art. More preferably, the term relates to 2-methylhistamine, 2-pyridylethylamine, 2-thiazolylethylamine, (R)-a-methylhistamine, impromidine, dimaprit, 4(5)-methylhistamine, diphenhydramine, pyrilamine, promethazine, chlorpheniramine, chlorcyclizine, terfenadine, and the like.

The term "vitamin" in the context of the cargo molecules relates to any compound, which is required as a nutrient in tiny amounts by an organism. Preferably, the term relates to any such compound known to the person skilled in the art. More preferably, the term relates to vitamin A, B1, B2, B3, B5, B6, B7, B9, B12, C, D, E, or K.

The term "analgesic agent" in the context of the cargo molecules relates to any compound used to relieve pain. Preferably, the term relates to any such compound known to the person skilled in the art. More preferably, the term relates to lidocaine, bupivacaine, novocaine, procaine, tetracaine, benzocaine, cocaine, mepivacaine, etidocaine, proparacaine, ropivacaine, and prilocalne.

The term "antineoplastic agent" in the context of the cargo molecules relates to any compound, which inhibits and combats the development of tumors. Preferably, the term relates to any such compound known to the person skilled in the art. More preferably, the term relates to pentostatin, 6-mercaptopurine, 6-thioguanine, methotrexate, bleomycins, etoposide, teniposide, dactinomycin, daunorubicin, doxorubicin, mitoxantrone, hydroxyurea, 5-fluorouracil, cytarabine, fludarabine, mitomycin, cisplatin, procarbazine, dacarbazine, paclitaxel, colchicine, and vinca alkaloids.

The term "hormone" in the context of the cargo molecules relates to any compound, which carriers as a messenger a signal from one cell (or group of cells) to another via the blood. Preferably, the term relates to any such compound known to the person skilled in the art. More preferably, the term relates to prostaglandine, serotonine, histamine, bradykinin, kallikrein, and gastrointestinal hormones, releasing hormones, pituitary hormones, insulin, vasopressin (ADH), glucagon, enkephalin, calcitonin, and corticosteroids.

The term "adhesion-molecule" in the context of the cargo molecules relates to molecules on the cell surface involved with the binding with other cells or with the extracellular matrix (ECM) in a cell adhesion process. Preferably, the term relates to any such molecule known to the person skilled in the art. More preferably, the term relates to IgSF CAMs like NCAM, ICAM-1, VCAM-1, PECAM-1, L1, CHL1, MAG, integrins, or selectins.

The term "receptor-molecules" in the context of the cargo molecules relates to protein on the cell membrane or within the cytoplasm or cell nucleus that binds to a ligand and typically transduces a signal. Preferably, the term relates to any such molecule known to the person skilled in the art. More preferably, the term relates to metabotropic receptors, G protein-coupled receptors, muscarinic acetylcholine receptors, adenosine receptors, adrenoceptors, GABA receptors, angiotensin receptors, cannabinoid receptors, cholecystokinin receptors, dopamine receptors, glucagon receptors, metabotropic glutamate receptors, histamine receptors, olfactory receptors, opioid receptors, chemokine receptors, calcium-sensing receptor, somatostatin receptors, serotonin receptors or secretin receptors.

The term "therapeutic organic molecules" in the context of the cargo molecules relates to organic molecules, which have a therapeutic effect on the animal, preferably on the human body. Preferably, the term relates to any such molecule known to the person skilled in the art. More preferably, the term relates to an organic drug having therapeutic potential.

The terms "organic inhibitors" and "peptide inhibitors" in the context of the cargo molecules relates to organic molecules or polypeptides which have an inhibitory effect on physiological functions, preferably on protein function like enzymatic functions. Preferably, the term relates to any such molecule known to the person skilled in the art. More preferably, the term relates to the protease inhibitor based ritonavir, the HIV protease inhibitor tipranavir, or sildenafil.

The term "anti-aging agent" in the context of the cargo molecules relates to any compound that prevents, slows, or reverses the effects of aging. Preferably, the term relates to any such compound known to the person skilled in the art. More preferably, the term relates to Premarin or Human Growth Hormone (HGH).

The compounds of the invention may enter eukaryotic cells without the need to interact with a receptor. Thus, in a further embodiment, the compound(s) of the invention is/are either linked or not linked to a cargo molecule as described herein above, is/are additionally linked to a specific, for example a cell-specific, targeting agent. Such a linkage may be any linkage as described herein above, preferably a peptide linkage.

In a specific embodiment of the present invention, it is preferred that one of the following cargos: β-lactamase, EGFP and adenylate cyclase domain of the *Bordetella pertussis* cyclolysin (Cya) is not linked via a peptide bond with the compounds of the invention.

The term "specific targeting agent" or "cell-specific targeting agent" means a molecule, which allows a (cell) specific interaction with structures on the surface of a cell and thereby facilitates the recognition of different cell types or tissue types in the animal body, preferably in the human body. Molecules which allow such (cell-) specific interaction may, for example, be ligands which specifically interact with receptors or receptor fragments which are located on the surface of a cell (e.g. tumor cells) and which are differentially expressed in specific cell types or tissue types. The term includes any suitable CD antigen as known to the person skilled in the art, for example from (http://www.pathology-outlines.com/cdmarkers.html) more preferably to CD1d, which may be used for the targeting of, e.g., dendritic cells, intestinal epithelial cells, B cell subset, NK T cell subset; CD 11a,b,c,d; CD14 and CD16/18, which may be used for the targeting of, e.g., macrophages; CD23, which may be used for the targeting of e.g., activated mature B cells expressing IgM or IgD (particularly mantle cells), activated monocytes/macrophages, T cell subsets, platelets, eosinophils, Langerhans cells, follicular dendritic cells, or intestinal epithelium; CD54 (also known as ICAM-1), which may be used for the targeting of, e.g., B and T cells and B cell precursors, monocytes, osteoclasts, endothelial cells, and various epithelial cells; CD57, which may be used for the targeting of, e.g., cells of the NK subset, T cell subset, neuroectodermal tissue, retina, brain, prostate, renal proximal tubules; CD64 (also called Fc gamma RI), which may be used for the targeting of antigen presenting cells including macrophages/monocytes, activated granulocytes, dendritic cells or early myeloid cells; CD91 (also known as Low density lipoprotein receptor-related protein 1 (LRP1); also called alpha-2-macroglobulin receptor), which may be used for the targeting of fibroblasts, dendritic cells, macrophages, liver, brain or lung tissue as well as CD-20, CD-45. Furthermore, the term relates to anti-CD antibodies, to molecular danger signals, TLRs, bacterial toxins, e.g. 'trapo' for nerve cells as described in WO 2006/114308 or DEC-205, which is typically present on dendritic cells. In addition, the term relates to a vascular-homing peptide, which may be specific for certain organs or tissues, like e.g. brain, kidney, lung, skin, or heart. More preferably, the term relates to such peptides as mentioned in Arap, W. et al. *Proc. Natl. Acad Sci. U.S.A.*, 99:1527-1531 (2002); Rajotte, D. et al., *J. Clin Invest.*, 102:430-437 (1998); Pasqualini, R., and Ruoslahti, E. (2002) *Nat. Rev. Cancer* 2:83; Rajotte, D. and Ruoshlati, E., *J. Biol. Chem.* 274:11593-11598 (1999); Essler, M., and Ruoshlati, E., *Proc. Natl. Acad. Sci. U.S.A.*, 99:2252-2257 (2002). Tumor homing peptide are also envisaged. The term "tumor homing peptide" means a protein, which comprises an RGD- and/or a NGR motif. Typically, proteins with a RGD motif bind to $\alpha v\beta 3$ and $\alpha v\beta 5$ integrins, which in turn are considered to be specific markers for angiogenic blood vessels (Eliceiri, B. P. and Cheresh, D. A., *Cancer J.* 6:S245-S249 (2000)). Furthermore, proteins with an NGR-Motif may bind to an aminopeptidase N, which in turn is specific for angiogenic, endothelia cells (Pasqualini, R. et al., *Cancer Res.* 60:722-727 (2000)). In a preferred embodiment, a tumor homing peptide comprising an RGD- and/or a NGR motif may be used for the general targeting of angiogenic cells indepently of the tumor type involved, as the person skilled in the art would know, e.g. from Arap, W. et al., *Science*, 279:377-380 (1998); Pasqualini, R. et al., *Nat. Biotech.* 15:542-546 (1997)).

In a further preferred embodiment YopM, a YopM fragment, or YopM variant may be fused in frame with the carboxyl terminus of the heavy chain of the $\alpha$DEC-205 as described in Boscardin et al. (*J. Exp. Med.*, 203: 599-606 (2006)).

In a further preferred embodiment the term "cell-specific targeting agent" includes agents which bind to (a) cell-marker which allow(s) the, preferably specific, targeting of osteoclasts. A particularily preferred cell-marker for osteoclasts is the calcitonin-receptor, alpha-V-beta3-integrine and/or vitronectine (Marta Monjo, Sébastien F. Lamolle, S. Petter Lyngstadaas, H. Jacob Remønd and Jan Eirik Ellingsen 2008 *Biomaterials* 29(28): 3771-3780; Susanne Granholm, Pernilla Lundberg, and Ulf H. J. Cell. Biochem. 104(3): 920-933; Davies J, Warwick J, Totty N, Philp R, Helfrich M, and Horton M 1989 J. Cell Biol. 109: 1817-1826; Clove J, Dodds R A, and Gowen M 1992. J. Cell Sci. 103: 267-271). Agents which may bind to this cell-marker are described herein and include for example antibodies etc.

In yet a further preferred embodiment the term "cell-specific targeting agent" relates to a virus, preferably an attenuated virus, which is linked to a compound of the invention. Such a combination may convey a cell or tissue tropism depending on the host cell spectrum of the virus used. The term "cell-specific targeting agent" also includes retroviridae, adenoviridae etc.

The term "cell-specific targeting agent" also includes an "antibody and functional fragments thereof" and refers to a monoclonal or a polyclonal antibody (see Harlow and Lane, "*Antibodies, A Laboratory Manual*", CSH Press, Cold Spring Harbor, USA, 1988) or a derivative of said antibody which retains or essentially retains its binding specificity. Preferred derivatives of such antibodies are chimeric antibodies comprising, for example, a mouse or rat variable region and a human constant region. The term "functional fragment" as used herein refers to fragments of the antibodies as specified herein which retain or essentially retain the binding specificity of the antibodies like, separated light and heavy chains, Fab, Fab/c, Fv, Fab', F(ab')2. The term "antibody" also comprises bifunctional (bispecific) antibodies and antibody constructs, like single-chain Fvs (scFv) or antibody-fusion proteins. The term "scFv fragment" (single-chain Fv fragment) is well understood in the art and preferred due to its small size and the possibility to produce such fragments recombinantly. Said antibody or antibody binding portion is a human antibody or a humanized antibody. The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A1 0 239 400 and WO90/07861.

In another aspect the present invention relates to a pharmaceutical composition comprising the YopM, a YopM fragment, or a YopM variant as defined herein, wherein said YopM, YopM fragment, or YopM variant is capable of autopenetrating the cell membrane and of integrating into the cell cytosol without the requirement of additional factors. It is also envisaged that the pharmaceutical composition comprises the compounds of the invention which are further modified as explained herein above, for example which are linked to a cargo molecule and/or linked to a cell-specific targeting agent etc. It is likewise envisaged that the pharmaceutical compositions of the present invention comprise the nucleic acids and/or vectors of the present invention. The pharmaceutical composition may optionally comprise a pharmaceutically acceptable carrier.

As already mentioned above, the present inventors surprisingly found that YopM or a YopM fragment or variant, which so far has not been characterized as a potential immunosuppressive therapeutic, is, once it has integrated into the cell cytosol, capable of effectively downregulating cytokines. Cytokines are an essential class of mediators in physiology and pathology. In the context of inflammation and disease cytokines and particularly pro-inflammatory cytokines play a key role in the accelleration and regulation of inflammatory reactions either by direct interactions or by their ability to induce the synthesis of cellular adhesion molecules or of other cytokines in various cell types involved in the immunological defense network. Many cytokines have benefical as well as deleterious effects for the organism. Thus, a delicate balance between different cytokine groups, in particular between pro-inflammatory, anti-inflammatory and regulatory cytokines has to be maintained and is vital for health. If this balance is disturbed, diseases like inflammatory bowel disease, rheumatoid arthritis, vascular disease or autoimmunity may develop. The unexpected dowregulation of cytokines, in particular of pro-inflammatory cytokines, by YopM and YopM fragments that have autopenetrated the cell membrane and entered the cytosol, as shown by the present inventors and illustrated in the Examples, converts YopM and its derivatives into efficient medical tools for the regulation of inflammatory reactions, for immunomodulation or for immunosuppresion.

To analyze and localize domains within YopM that mediate immunomodulation, the truncated versions of YopM previously described (see Example 2), were used to treat differentiated HL60 cells. Besides the control protein YopM$_{87-C}$, only those versions of YopM were used, that are all still able to penetrate host cell membranes (see Example 2), because we presumed that, the autopenetration ability is required for immunomodulation. While the control protein YopM$_{87-C}$, which does not autopenetrate cells, was not able to reduce transcription of TNFα, the autopenetrating versions, YopM$_{N-239}$, and YopM$_{55-C}$, were still able to reduce transcription of the TNFα (see FIG. 11). These results exclude a role of the C-terminus and the first amino-terminal helix of YopM in immunomodulation. The fact that the fusion protein 2αH-GFP containing both α-helices of YopM, was no longer able to reduce transcription of TNFα (FIG. 11) indicates that the LRRs 1-8 of YopM harbour the potential immunomodulatory domain. Furthermore, this result excludes a role of the amino-terminal α-helices of YopM in immunomodulation.

Thus, in a further embodiment the YopM, YopM fragment, or YopM variant as described herein, is capable of autopenetrating the cell membrane and of integrating into the cell cytosol without the requirement of additional factors and is capable of downregulating cytokines i.e. the compounds of the invention comprise in this embodiment the immunomodulatory domain(s) of YopM, particularity at least one leucine-rich repeat (LRR), i.e. one, two, three, four, five, six, seven or eight LRRs. The addition of further LRRs is also envisaged. It is likewise envisaged that these compounds of the invention are linked to/attached to a cargo molecule.

The term "cytokines" relates to soluble proteins and peptides that act as humoral regulators, which, either under normal or pathological conditions, modulate the functional activities of individual cells and tissues and also mediate interactions between cells directly and regulate processes taking place in the extracellular environment. The term encompasses type 1 cytokines produced by Th1 T-helper, type 2 cytokines produced by Th2 T-helper cells, interleukins, chemokines or interferons, e.g. IL-1ra (antagonist), CNTF, LIF, OSM, Epo, G-CSF, GH, PRL, IP10, I309, IFN-alpha, IFN-beta, IFN-gamma, IL2, IL3, IL4, IL5, IL6, IL7, IL8, IL9, IL10, IL11, IL12 (p35+p40), IL13, IL14, IL15, IL16, IL17 A-F, IL18, IL19, IL20, IL21, IL22, IL23 (p19+p40), IL24, IL25, IL26, IL27 (p28-EBI3), IL28A, IL28B, IL29, IL30, IL31, IL32, IL33, IL35 (p35-EBI3), LT-alpha, LT-beta, LIGHT, TWEAK, APRIL, BAFF, TL1A, GITRL, OX40L, CD40L, FASL, CD27L, CD30L, 4-1BBL, TRAIL, RANK, GM-CSF, M-CSF, SCF, IL1-alpha, IL1-beta, aFGF, bFGF, int-2, KGF, EGF, TGF-alpha, TGF-beta, TNF-alpha, TNF-beta, betacellulin, SCDGF, amphiregulin or HB-EGF, as is known to the person skilled in the art and can be derived, for example, from Tato, C. M. & Cua, D. J. (*Cell* 132: 900; Cell 132: 500, *Cell* 132: 324, (2008)) or from Cytokines & Cells Online Pathfinder Encyclopaedia (http://www.copewith-cytokines.de). "Pro-inflammatory cytokines" are also contemplated. The term "pro-inflammatory cytokine" means an immunoregulatory cytokines that favours inflammation. Typically, pro-inflammatory cytokines comprise IL-1-alpha, IL-1-beta, IL-6, and TNF-alpha. These pro-inflammatory cytokines are largely responsible for early responses. Other pro-inflammatory mediators include LIF, IFN-gamma, IFN-alpha, OSM, CNTF, TGF-beta, GM-CSF, TWEAK, IL-11, IL-12, IL-15, IL-17, IL-18, IL-19, IL-20, IL-8, IL-16, IL-22, IL-23, IL-31, and IL-32 (Tato, C. M. & Cua, D. J. *Cell* 132:900; *Cell* 132:500, *Cell* 132, 324 (2008)). These pro-inflammatory cytokines may act as endogenous pyrogens (IL-1, IL-6, TNF-alpha), up-regulate the synthesis of secondary mediators and pro-inflammatory cytokines by both macrophages and mesenchymal cells (including fibroblasts, epithelial and endothelial cells), stimulate the production of acute phase proteins, or attract inflammatory cells. Preferably, the term "pro-inflammatory cytokine" relates to TNF-alpha, IL-15, IFN-gamma, IFN-alpha, IL-1-beta, IL-8, IL-16 and IL-22.

The term "downregulates" means that the mRNA levels of an expressed gene, e.g. of a cytokine gene, and/or the protein levels expressed by such mRNAs is reduced in the presence of YopM, a YopM fragment, a YopM variant, and/or an immunmodulatory domain as described herein. The downregulation of mRNA and/or protein expressed by that mRNA in the context of the compounds of the invention can be tested and determined by methods known to a person skilled in the art or by methods exemplified in the appended examples (see e.g. Example 9). "Downregulating" encompasses that the expression (either on mRNA or protein level) is reduced by at least 5%, 10%, 15%, 20%, 25%, 30%, 35%, 40%, 45%, 50%, 55%, 60%, 65%, 70%, 75%, 80%, 85%, 90%, 95% or 99% in comparison to a control, in which the incubation has been carried out without YopM, e.g. solely in the presence of medium. It can be tested by a method of quantitive RNA analysis, as described in Myers, T. W. and Gelfand, D. H., *Biochem.* 30:7661-7667 (1991); Krug, M. S. and Berger, S. L., *Methods Enzymol.* 152:316-325 (1987); Bustin, S. A., *J. Mol. Endocrinol.* 29:169-193 (2000); Bustin, S. A., *J. Mol. Endocrinol.* 25:23-39 (2002); Ståhlberg, A. et al., Clin. Chem. 50:509-515 (2004)). Briefly, such a method comprises the incubation of cells to be tested, e.g. HL60 cells or HeLa cells, with YopM, a YopM fragment or a YopM variant, for a time period of 1 h to 24 h, preferably of 2 h to 20 h, more preferably of 3 h to 18 h. Most preferably, the cells are incubated for 3 h, 6 h and 18 h to allow a comparison of the expression pattern. The YopM, a YopM fragment, or a YopM variant may be present in any suitable medium known to the skilled person. Preferably, the protein is provided in an infection medium comprising, e.g. DMEM, FCS, L-glutamine, HEPES and methyl-α-D-mannose. More preferably, the infection medium comprises 500 ml DMEM (for HeLa cells) or RPMI (for HL60 cells), 10% (v/v) FCS, 1 mM L-glutamine, 10 mM HEPES and 1% (w/v) methyl-α-D-mannose. For the assay cell culture dishes comprising the cells to be tested, e.g. after seeding $5 \times 10^6$ cells and growing to a confluent surface layer may be incubated with the YopM protein, YopM fragment, or YopM variant present in an infection medium as described herein above in a concentration of 1 to 100 μg per ml, preferably of 5 to 50 μg per ml, more preferably of 10 to 30 μg per ml and even more preferably of 15 to 25 μg per ml and most preferably at 5 μg per ml. HL60 cells can be differentiated to macrophages, e.g. by the addition of any suitable compound known to the person skilled in the art, e.g by the addition of PMA (phorbol 12-myristate 13 acetate) as derivable from Fontana et al. (*Proc. Natl Acad Sci. U.S.A* 78:3863-3866 (1981)). Subsequently, the cells may be washed with any suitable buffer known to the skilled person, e.g. with D-PBS/Mg$^{2+}$. Preferably, the washing is carried out in ice-cold buffer and repeated twice. Subsequently, the cells are permeabilised by any suitable means known to the skilled artisan. Preferably, the cells are suspended in a suitable lysis buffer and the suspension may then be lysed, e.g. with an RNA isolation kit, preferably with the Roche High Pure RNA isolation kit. Subsequently, RNA is extracted by any suitable means know to the person skilled in the art. In a further step RNA is measured, reverse transcribed using T7 Oligo (dT) Primer from Ambion, and analysed by any suitable means known to the person skilled in the art, preferably by quantitative RT-PCR as known to the person skilled in the art, e.g. derivable from Myers, T. W. and Gelfand, D. H., *Biochem.* 30:7661-7667 (1991); Krug, M. S. and Berger, S. L., *Methods Enzymol.* 152:316-325 (1987); Bustin, S. A., *J. Mol. Endo-* crinol. 29:169-193 (2000); Bustin, S. A., *J. Mol. Endocrinol.* 25:23-39 (2002); Ståhlberg, A. et al., Clin. Chem. 50:509-515 (2004)). More preferably, a Transcriptor kit from Roche, a Sybr Green kit from Roche, and/or a LightCycler from Roche are used for quantitative Real-Time RT-PCR. The RNA analysis is carried out for any protein or factor of interest, e.g. for any suitable cytokine known to the person skilled in the art, preferably for a cytokine as described herein above. More preferably, the analysis is carried out for TNF-alpha, IL-15 and IFN-gamma. Most preferably, Real Time RT-PCR primers may be derived from the universal probe set library obtainable from Roche.

A molecule, in particular YopM, a YopM fragment, or a YopM variant is regarded to be capable of downregulating cytokines on the mRNA level of a cytokine, preferably of TNF-alpha, IL-15 or IFN-gamma, in a cell, which has been incubated with YopM, a YopM fragment or a YopM variant according to the above described assay, is reduced by at least 5%, 10%, 15%, 20%, 25%, 30%, 35%, 40%, 45%, 50%, 55%, 60%, 65%, 70%, 75%, 80%, 85%, 90%, 95% or 99% in comparison to a control, in which the incubation has been carried out without YopM, e.g. solely in the presence of medium.

Accordingly, a YopM, YopM fragment, or YopM variant as described herein above, is capable of autopenetrating the cell membrane and of integrating into the cell cytosol without the requirement of additional factors and is preferably capable of downregulating pro-inflammatory cytokines. More preferably, it is capable of downregulating any one of pro-inflammatory cytokines TNF-alpha, IL-15, IFN-alpha, IL-1-beta, IL-8, IL-16 and IL-22, even more preferably, it is capable of downregulating at least any of TNF-alpha, IL-15 or IFN-gamma. Most preferably, it is capable of downregulating IFN-gamma. The term "downregulating" has been described herein above. The downregulation may be tested in a RNA quantification assay or a test known to the person skilled in the art, for example a test as described in the Examples.

In another preferred embodiment the YopM fragment or YopM variant as described herein above is capable of autopenetrating the cell membrane and of integrating into the cell cytosol without the requirement of additional factors, and is capable of downregulating cytokines and/or cytokine receptors i.e. the compounds of the invention comprise in this embodiment the immunomodulatory domain(s) of YopM, particularily at least one leucine-rich repeat (LRR), i.e. one, two, three, four, five, six, seven or eight LRRs. The addition of further LRRs is also envisaged. It is likewise envisaged that these compounds of the invention are linked to/attached to a cargo molecule.

The term "cytokine receptor" refers to any receptor molecule, which is able to bind a cytokine as a ligand. In the context of the present invention, the term preferably relates to any receptor of the cytokines mentioned herein above, more preferably of the pro-inflammatory cytokines mentioned herein above. Most preferably, the term relates to receptors for TNF, IL-6, IL-12-beta, IL-15 and IL-20. The term "downregulates" has been described herein above. The downregulation may be tested in a RNA quantification assay or test known to the person skilled in the art and/or by a method as described in the Examples.

In a further preferred embodiment the YopM, YopM fragment, or YopM variant as described herein above is capable of autopenetrating the cell membrane and of integrating into the cell cytosol without the requirement of additional factors and is capable of downregulating cytokines, cytokine receptors and/or genes which respond to cytokines i.e. the compounds of the invention comprise in this embodiment the immunomodulatory domain(s) of YopM, particularily at least one leucine-rich repeat (LRR), i.e. one, two, three, four, five, six, seven or eight LRRs. The addition of further LRRs is also envisaged. It is likewise envisaged that these compounds of the invention are linked to/attached to a cargo molecule.

The term "genes which respond to cytokines" refers to any gene, which is regulated, i.e. can be activated or inactivated, or whose transcription can be initiated or stopped by any of the cytokines mentioned herein above. More preferably, it relates to genes that are regulated by TNF-alpha or IFN. Most preferably, the term relates to genes that are induced by TNF-alpha or induced by IFN. The term "downregulates" has been described herein above. The downregulation may be tested in a RNA quantification assay or test known to the person skilled in the art.

Figure 14:
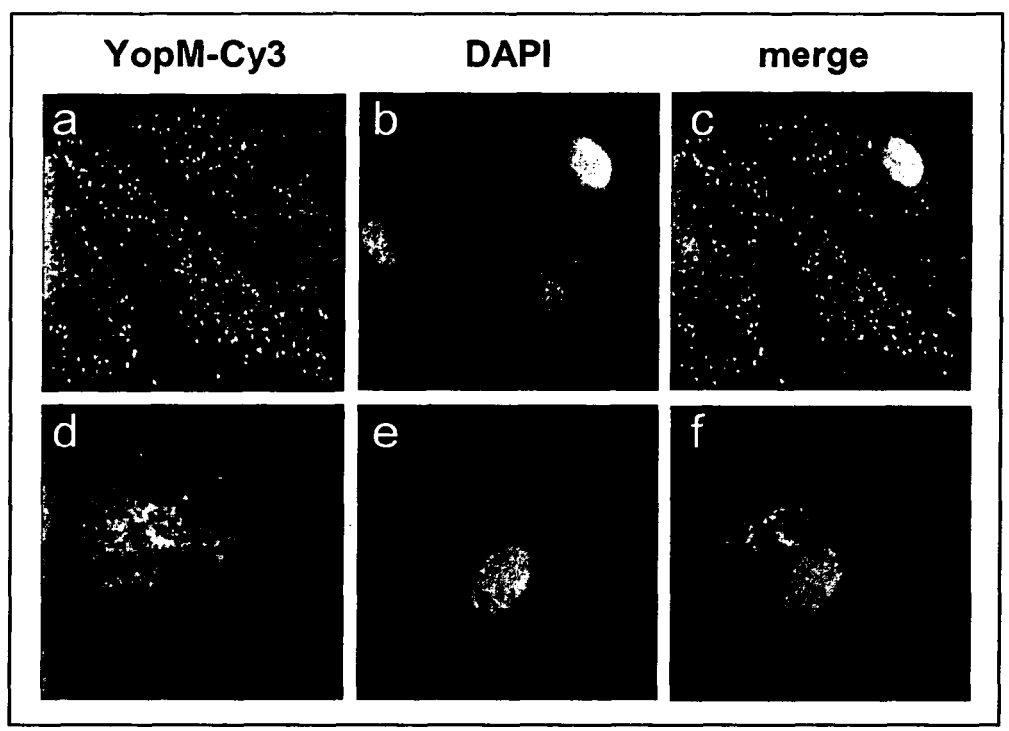
Figure 15:
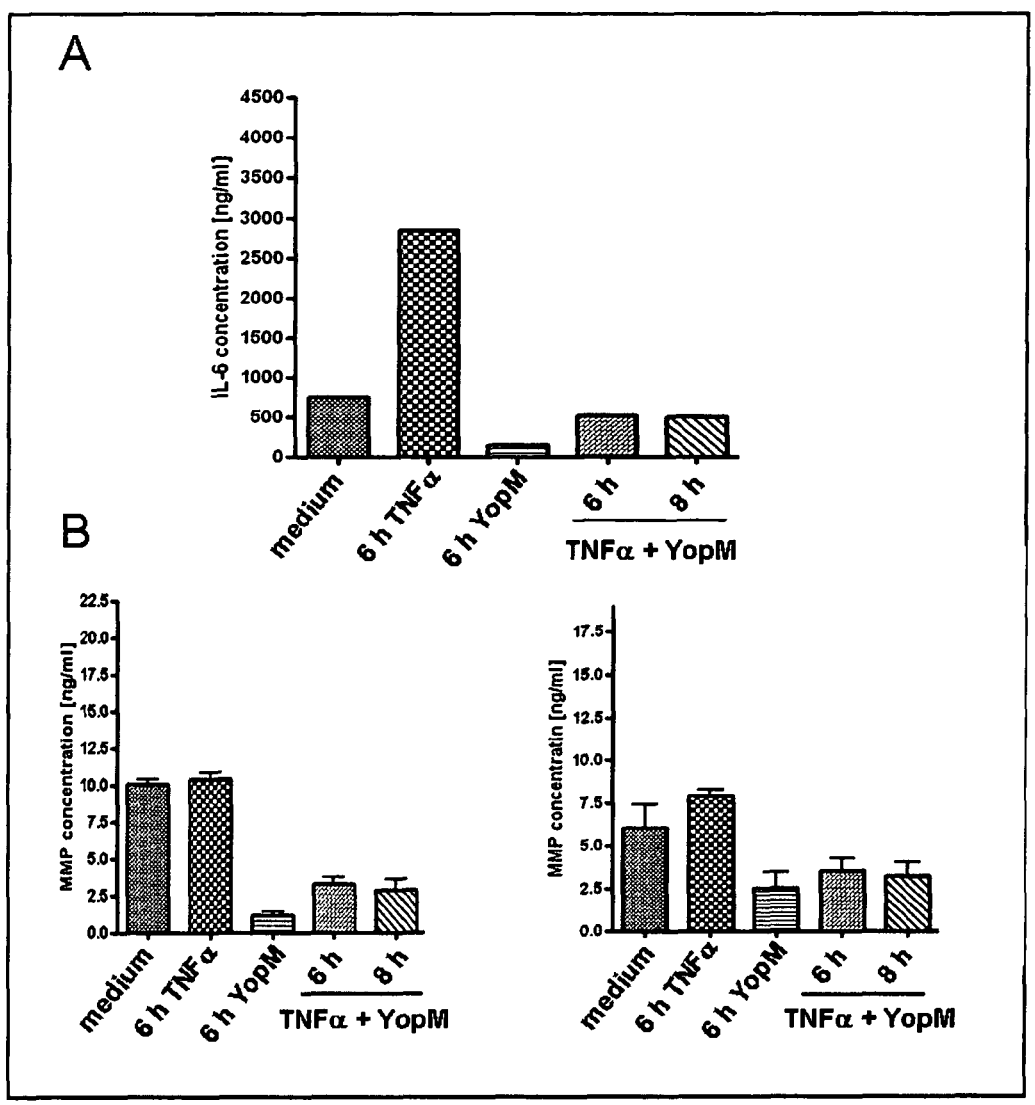

Rheumatoid arthritis (RA) is a chronic, systemic autoimmune disorder that most commonly causes inflammation and tissue damage in joints (arthritis). The arthritis of RA is due to synovitis, which is an inflammation of the synovial membrane that lines joints and tendon sheaths. RA synovial fibroblasts (RASFs) together with synovial macrophages are active drivers of joint destruction in RA. In this destructive process, RASFs actively cause inflammation and degradation of the joint by producing inflammatory cytokines and matrix-degrading molecules (Müller-Ladner, U., Ospelt, C., Gay, S., Distler, O., Pap, T. *Arthritis Res. Ther.* 9:223-233 (2007)). Due to the active involvement of RASFs in RA development, we investigated the interaction of recombinant YopM with this cell type. For this purpose, YopM was isolated and purified via Ni-NTA affinity chromatography, dialyzed against PBS and conjugated to the reactive fluorescent Cy3-dye as described in the manufacturer's instructions (Cy3-DyeLight Ab labeling Kit; GE Healthcare). RASFs were incubated with YopM-Cy3 for 30 min and 1 h, respectively. After incubation, the cells were prepared for fluorescence microscopy. DNA was stained with Draq5, and cells were analyzed by confocal laser scanning microscopy. After 30 min of incubation with YopM-Cy3, the protein appeared in vesicle-like structures inside the cytoplasm of RASFs (FIG. 14; a-c), indicating that YopM also autopenetrates this cell type. After prolonged incubation for 1 h, the amount of YopM inside the cytoplasm of incubated RASFs increased, and the characteristic accumulation of YopM in perinuclear regions of the cells was observed (FIG. 14; d-f). After we confirmed the ability of YopM to penetrate RASFs, we were interested whether YopM might have an effect on inflammation and cartilage destruction. In this context, the secretion of IL-6 by RASFs induces acute phase reactions and inflammation in the synovium. The cartilage destruction observed in RA is caused by secretion and activation of matrix metalloproteinases (MMPs). MMP-1 and MMP-3 are the major enzymes produced by RASFs. MMP-1 degrades fibrillar collagens (collagens I, II, VII and X), whereas MMP-3 degrades a broad array of extracellular matrix substrates (Noh, E. M., Kim, J. S., Hur, H., Park, B. H., Song, E. K., Han, M. K., Kwon, K. B., Yoo, W. H., Shim, I. K., Lee, S. J., Youn, H. J., Lee, Y. R. *Rheumatology* 48: 5-48 (2009)). In order to analyze YopM's influence on secretion of IL-6, MMP-1 and MMP-3, RASFs were co-incubated with TNFα (10 ng/ml) and recombinant YopM for different time points. Subsequently, the production of IL-6, MMP-1 and MMP-3 in the culture supernatants of RASFs was determined by ELISA (FIG. 15 A-C; medium, TNFα and YopM). After incubation of RASFs with TNFα, the production of IL-6 is induced (at least 3-fold), while incubation with YopM resulted in a reduced IL-6 production compared to control cells (x-fold; medium, FIG. 15 A). Co-incubation of RASFs with TNFα and YopM revealed a drastic inhibition of TNFα- induced IL-6 production. This effect persisted after 8 h of incubation with recombinant YopM (FIGS. 15 A; 6 h and 8 h). The production of MMP-1 and MMP-3 is also drastically reduced. Incubation of RASFs with YopM alone, as well as co-incubation with TNFα and YopM for 6 h and 8 h resulted in strongly reduced amounts of these cartilage-destroying molecules. Taken together, these results demonstrate that recombinant YopM can penetrate cells involved in the development of RA and has an inhibitory effect on the production of inflammatory and cartilage-destroying molecules. This underlines our claim that recombinant YopM can be beneficially applied in the treatment of autoimmune diseases such as RA.

Thus, in further preferred embodiment the YopM, YopM fragment, and/or YopM variant is/are capable of autopenetrating the cell membrane and of integrating into the cell cytosol without the requirement of additional factors and is/are capable of downregulating cytokines and/or cytokine receptors and/or genes which respond to cytokines and/or "cartilage-destroying molecules" i.e. the compounds of the invention comprise in this embodiment the immunomodulatory domain(s) of YopM, particularily at least one leucine-rich repeat (LRR), i.e. one, two, three, four, five, six, seven or eight LRRs. The addition of further LRRs is also envisaged. It is likewise envisaged that these compounds of the invention are linked to/attached to a cargo molecule.

The term "cartilage-destroying molecules", includes matrix-metalloproteinases like, for example collagenases and gelatinases but is not limited thereto. "Matrix-metalloproteinases" includes all known forms like for example MMP 1, 2, 3, 4, 5, 6, 7, 8, 9, 10, 11, 12, 13 etc. Preferred are MMP 1, 2, 3, 9, 10, 12 and/or 13 (the participitation of MMP 2, 9, 10, 12 and 13 in the development of rheumathoid arthritis is described in. K. Andreas, C. Lübke, T. Häupl, T. Dehne, L. Morawietz, J. Ringe, C. Kaps, and M. Sittinger. Arthritis Res Ther. 2008; 10(1): R9, M. Xue, L. March, P. N. Sambrook, C. J. Jackson Arthritis & Rheumatism, 2007 58(9); 2864-2874; C. Rossa, M. Liu, P. Bronson, K. L. Kirchwood. J. Endotoxin Res. 2007 13(2): 85-93). MMP-1 and MMP-3 are particularily preferred. Further "cartilage-destroying molecules" are likewise envisaged. These further cartilage-destroying molecules can be evaluated by employing the methods of the appended Examples (e.g. Example 9) or other methods, which are known to the skilled person.

Figure 16:
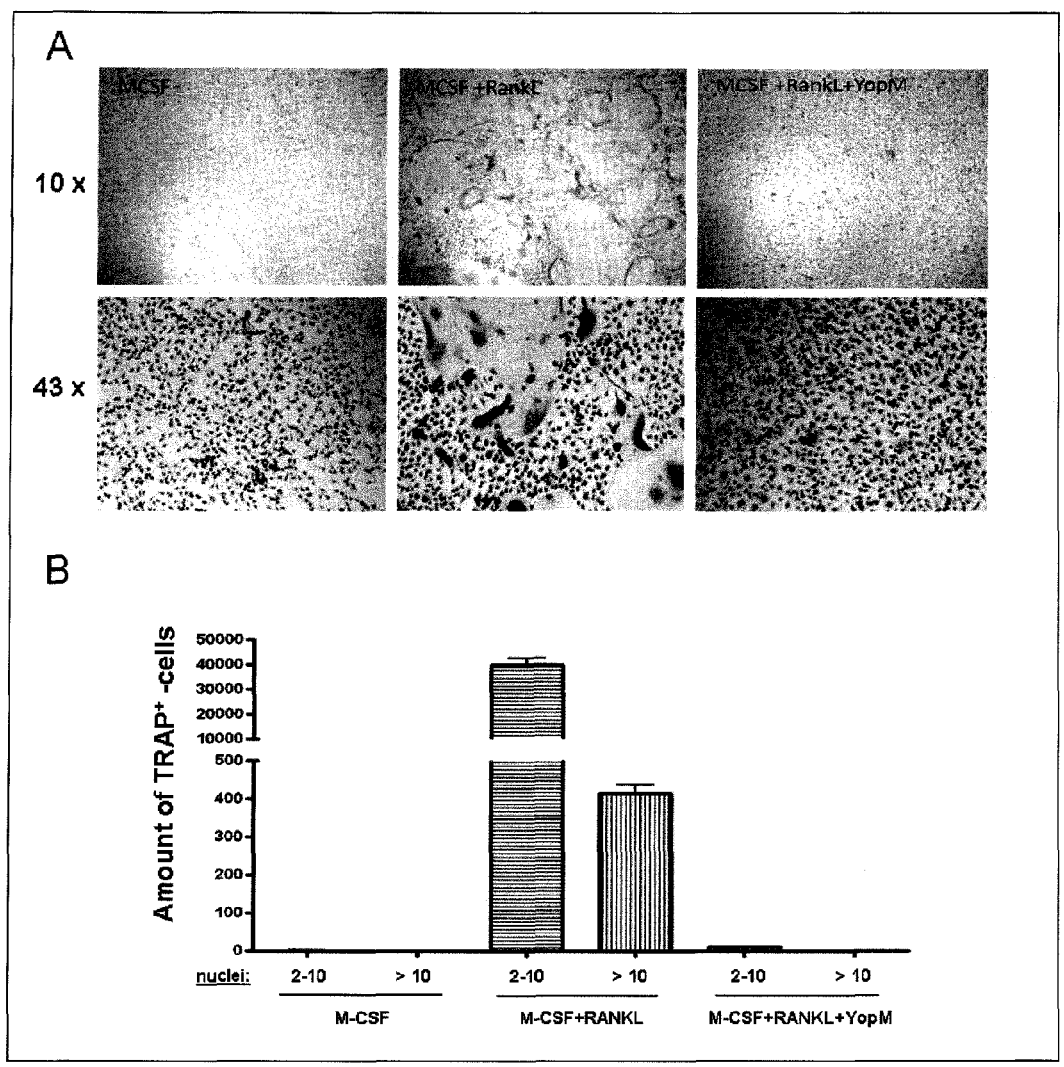

In addition to controlling inflammation, prevention of structural damage is a key objective of antirheumatic therapy. One hallmark of RA is local bone erosion, which involves destruction of juxta-articular bone. This structural damage is based on formation of osteoclasts in and around the joint, which resorb mineralized cartilage and subchondral bone. The osteoclast are an integral part of the mixed cellular infiltrate of inflammatory arthritis and accumulation of these cells at sites of structural damage suggest that molecules involved in osteoclast formation are important players in the destructive processes of the disease (Schett, G. Arthritis Res. Ther. 9 Suppl 1:S2 (2007)). In this context, the Receptor Activator for Nuclear Factor κB Ligand (RANKL) and Macrophage Colony Stimulating Factor (M-CSF) are essential for the differentiation of osteoclasts from their precursor cells, and a lack of either molecule is sufficient to block osteoclast formation completely (Yoshida H, Hayashi S, Kunisada T, Ogawa M, Nishikawa S, Okamura H, Sudo T, Shultz L D, Nishikawa S. Nature 345: 442-444 (1990)). In order to test a possible influence of YopM on osteoclastogenesis, bone marrow cells of adult mice of 8-12 weeks of age were isolated from the cut shafts of mouse femurs and tibias by fluid pressure applied by a syringe. Cultures were maintained in 200 µl α-MEM (supplemented with antibiotics and 10% FCS) for 5 days, with a change of medium every 2-3 days. Incubation of the cultures with soluble recombinant RANKL (50 ng/ml) and M-CSF (30 ng/ml) induces the development and fusion of tartrate-resistant acid phosphatase positive (TRAP$^+$) osteoclasts at 3-5 days (Gardner, C. R. Cell Tissue Res. 330:111-121 (2007)). Mouse bone marrow cells induced by RANKL and M-CSF were incubated with YopM (10 ng/ml) for 5 days, while control cells were incubated with RANKL/M-CSF only. Subsequently, cells were prepared for microscopy. TRAP$^+$-cells were stained with 200 µl of solution containing Fast Garnett (leukocyte acid phosphatase kit, Sigma Diagnostics) in the presence of tartrate, for 30 min at 37° C. Examination of cells by light microscopy (10× and 43× magnification) revealed that control cells stimulated with M-CSF for 5 days did not show any formation of multinuclear (pre-)-osteoclasts, while co-stimulation with M-CSF and RANKL induced the development and fusion of TRAP$^+$ osteoclasts (FIG. 16A). In comparison, co-incubation with YopM in addition to stimulation with the two mediators of osteoclastogenesis lead to strong inhibition of osteoclastogenesis of bone marrow cells (FIG. 16, A). Of the YopM co-incubated cells, only few developed to small intermediate cells (2-10 nuclei), as also observed in control cells stimulated with M-CSF (FIG. 16, A). Furthermore, the quantification of TRAP$^+$-multinuclear osteoclasts by light microscopy revealed that M-CSF and RANKL stimulation induces development of TRAP$^+$ (pre-) osteoclast (2-10 nuclei) and also fusion of these cells to larger multinuclear osteoclasts (>10 nuclei; FIG. 16 B). As already shown by light microscopy, this effect was completely inhibited by co-incubation of YopM (FIG. 16B). Taken together, our results indicate that YopM is able to reduce the production of inflammatory mediators relevant in RA (see e.g. Example 9), and is capable of preventing structural damage by inhibition of osteoclastogenesis. Both of these YopM effects might be beneficial in an antirheumatic therapy against inflammation and structural damage.

The underlying mechanism in all cases of osteoporosis is an imbalance between bone resorption and bone formation. In normal bone, there is constant matrix remodeling of bone; up to 10% of all bone mass may be undergoing remodeling at any point in time. The process takes place in bone multicellular units (BMUs) as first described by Frost in 1963.[Frost H. M., Thomas C. C. Bone Remodeling Dynamics. Springfield, Ill.: 1963.] Bone is resorbed by osteoclast cells (which derive from the bone marrow), after which new bone is deposited by osteoblast cells (Raisz, L. G., J. Clin. Invest. 115 (12): 3318-3325 (2005)). The three main mechanisms by which osteoporosis develops are an inadequate peak bone mass (the skeleton develops insufficient mass and strength during growth), excessive bone resorption and inadequate formation of new bone during remodeling. An interplay of these three mechanisms underlies the development of fragile bone tissue (Raisz, L. G. J. Clin. Invest. 115 (12): 3318-3325] (2005)). The activation of osteoclasts is regulated by various molecular signals, of which RANKL (receptor activator for nuclear factor κB ligand) is one of best studied. This molecule is produced by osteoblasts and other cells (e.g. lymphocytes), and stimulates RANK (receptor activator of nuclear factor κB). Osteoprotegerin (OPG) binds RANKL before it has an opportunity to bind to RANK, and hence suppresses its ability to increase bone resorption. RANKL, RANK and OPG are closely related to tumor necrosis factor and its receptors.

It is envisaged that the compounds of the invention can be used for the treatment, prevention and/or amelioration of the diseases described herein.

The present invention also relates to a pharmaceutical composition comprising a YopM, YopM fragment, or YopM variant as described herein above which is capable of autopenetrating the cell membrane and of integrating into the cell cytosol without the requirement of additional factors and is capable of downregulating cytokines and/or cytokine receptors and/or genes which respond to cytokines and/or cartilage-destroying molecules and/or is capable of inhibiting osteoclastogenesis i.e. the compounds of the invention comprise in this embodiment the immunomodulatory domain(s) of YopM, particularily at least one leucine-rich repeat (LRR), i.e. one, two, three, four, five, six, seven or eight LRRs. The addition of further LRRs is also envisaged. It is likewise envisaged that these compounds of the invention are linked to/attached to a cargo molecule. Said pharmaceutical composition may optionally comprise a pharmaceutically acceptable carrier.

"Osteoclastogenesis" is a term which is well-known in the art. "Inhibiting osteoclastogenesis" means that the M-CSF and RANKL stimulation of bone marrow cells, for example of adult mice, is reduced by at least 5%, 10%, 15%, 20%, 25%, 30%, 35%, 40%, 45%, 50%, 55%, 60%, 65%, 70%, 75%, 80%, 85%, 90%, 95% or 99% in comparison to a control, in which the incubation has been carried out without YopM, fragments, variants and/or immunmodulatory domains thereof. The M-CSF and RANKL stimulation of bone marrow cells induces development of TRAP+(pre-) osteoclast (2-10 nuclei) and also fusion of these cells to larger multinuclear osteoclasts. Methods to evaluate this reduction are exemplified herein.

Inhibiting osteoclastogenesis has an impact on many bone diseases as the osteoclast differentiation and the level of osteoclast activity in turn modulates bone resorption. The compounds of the invention may thus be used to treat bone diseases characterized by changes in bone resorption, such as osteoporosis, osteomyelitis, osteopenia, hypercalcemia, bone loss due to arthritis metastasis, immobilization or periodontal disease, Paget's disease, osteopetrosis, prosthetic loosening and the like.

The present invention further relates to the immunomodulatory domain of YopM as well as to a pharmaceutical composition comprising these immunomodulatory domain of YopM, wherein said domain is capable of downregulating cytokines, and/or cytokine receptors and/or genes which respond to cytokine and/or cartilage-destroying molecules and/or is capable of inhibiting osteoclastogenesis, but has essentially no capability of autopenetrating the cell membrane and of integrating into the cell cytosol, i.e. they do not comprise one or both amino-terminal α-helices of YopM, and/or the amino-terminal α-helices are inactivated (for example by way of mutation like deletion, insertion etc. or otherwise). "Essentially no capability of autopenetrating the cell membrane and of integrating into the cell cytosol" means that these compounds of the invention are per se able to autopenetrate the cell membrane and to integrate into the cell cytosol not more than about 5%, 10%, 15%, 20%, 25%, 30%, of the autopenetration and integration capability of YopM, for example YopM selected from YopM of the species Yersinia enterocolitica, Yersinia pseudotuberculosis or Yersinia pestis, preferably that of Yersinia enterolitica 8081v, Serotype O:8. This can be tested in a suitable method, for example a method as exemplified herein or detailed in the appended examples.

Said pharmaceutical composition may optionally comprise a pharmaceutically acceptable carrier. An "immunomodulatory domain of YopM" comprises at least one leucine-rich repeat (LRR) of YopM, i.e. one, two, three, four, five, six, seven or eight LRRs. The addition of further LRRs is also envisaged. Variants and fragments of said immunmodulatory domain are likewise envisaged. It is also envisaged that these compounds of the invention are modified as exemplified for YopM, YopM fragments, and YopM variants herein above (etc. pegylated, labeled, etc.). Said variants and fragments are capable of downregulating cytokines, and/or cytokine receptors and/or genes which respond to cytokine and/or cartilage-destroying molecules and/or are capable of inhibiting osteoclastogenesis but have lost their capability of auto-penetrating the cell membrane and of integrating into the cell cytosol. The use of said immunomodulatory domain of YopM for immunomodulation, for example for immunomodulation of inflammatory reactions, for the inhibition of osteoclastogenesis or for the treatment of arthritis, osteoarthritis, (juvenile) chronic arthritis, rheumatoid arthritis, psoriatic arthritis, A. mutilans, septic arthritis, infectious arthritis and/or reactive arthritis is also envisaged. It is also envisaged that the immunomodulatory domain of YopM are linked/attached to other cell penetrating entities, for example CPPs that are heterologous to Yersinia. Nucleic acids expressing the immunomodulatory domains of YopM, vectors comprising said nucleic acids and cells comprising said nucleic acids and/or vectors are also contemplated.

In a further aspect the present invention relates to a pharmaceutical composition as defined herein above for immunomodulation, preferably for immunomodulation of inflammatory reactions. The term "immunomodulation" means regulation of reactions of the immune system. The term "immunomodulation of inflammatory reactions" refers to the regulation of inflammatory reactions of the immune system. Such inflammatory reactions are known to the skilled person and can be derived, for example, from Schmidt-Schönbein (Annu. Rev. Biomed. Eng. 8: 93-151 (2006)).

In a preferred embodiment the pharmaceutical composition as defined herein above is for the treatment of diseases caused by autoimmunity of the host. The term "diseases caused by autoimmunity of the host" means a disease, which is caused by an immune reaction of the host's immune system. Such diseases are known to the person skilled in the art and can be derived, for example, from http://www.sbi.uni-rostock.de/aidb/home.php. Preferably, the term relates to acute disseminated encephalomyelitis (ADEM), Addison's disease, ankylosing spondylitis, antiphospholipid antibody syndrome (APS), aplastic anemia, autoimmune hepatitis, autoimmune Oophoritis, celiac disease, Crohn's disease (Morbus Crohn), diabetes mellitus type 1, gestational pemphigoid, goodpasture's syndrome, Graves' disease, Guillain-Barré syndrome (GBS), Hashimoto's disease, idiopathic thrombocytopenic purpura, Kawasaki's disease, lupus erythematosus, Mixed Connective Tissue Disease, multiple sclerosis, myasthenia gravis, opsoclonus myoclonus syndrome (OMS), optic neuritis, Ord's thyroiditis, pemphigus, pernicious anaemia, primary biliary cirrhosis, rheumatoid arthritis, Reiter's syndrome, Sjögren's syndrome, Takayasu's arteritis, temporal arteritis, Warm autoimmune hemolytic anemia and Wegener's granulomatosis.

In a further preferred embodiment the pharmaceutical composition as defined herein above is for the treatment of "inflammation". The term "inflammation" means a biological response of tissues, e.g. vascular tissues, to harmful stimuli, such as pathogens, damaged cells, or irritants. Such a pathological condition is known to the person skilled in the art and can be derived, for example, from Schmidt-Schonbein (Annu. Rev. Biomed. Eng. 8: 93-151 (2006)). Preferably, the term relates to acute inflammation or chronic inflammation. Furthermore, it encompasses inflammatory disorders like asthma, chronic prostatitis, glomerulonephritis, hypersensitivities, inflammatory bowel diseases, pelvic inflammatory disease, reperfusion injury, arthritis, osteoarthritis, (juvenile) chronic arthritis, rheumatoid arthritis, psoriatic arthritis, A. mutilans, septic arthritis, infectious arthritis and/or reactive arthritis, transplant rejection or vasculitis. It also encompasses allergic reactions, inflammatory myopathies, atherosclerosis, ischaemic heart disease, gastroenteritis, chronic gastritis, colitis ulcerose and psoriasis or proriasis arthritis.

More preferably, the pharmaceutical composition is for the regulation of inflammatory reactions of the immune system, the treatment of diseases caused by autoimmunity of the host, the treatment of inflammation, chronic inflammation, gastroenteritis, chronic gastritis, inflammatory bowel diseases (IBD), colitis ulcerosa, psoriasis, allergic reactions, Morbus Crohn, arthritis, osteoarthritis, (juvenile) chronic arthritis, rheumatoid arthritis, psoriatic arthritis, A. mutilans, septic arthritis, infectious arthritis and/or reactive arthritis or for suppressing the immune system.

In another aspect, the present invention relates to the use of YopM, a YopM fragment, or a YopM variant, and/or the immunomodulatory domain of YopM of the invention for the preparation of a pharmaceutical composition for immunomodulation of inflammatory reactions, the regulation of inflammatory reactions of the immune system, the treatment of diseases caused by autoimmunity of the host, and/or the treatment of inflammation, chronic inflammation, gastroenteritis, chronic gastritis, inflammatory bowel diseases (IBD), colitis ulcerosa, psoriasis, allergic reactions, Morbus Crohn, arthritis, osteoarthritis, (juvenile) chronic arthritis, rheumatoid arthritis, psoriatic arthritis, A. mutilans, septic arthritis, infectious arthritis, and/or reactive arthritis, or for suppressing the immune system.

A pharmaceutical composition according to the present invention may be administered with the help of various delivery systems known to the person skilled in the art, e.g., encapsulation in liposomes, microparticles, microcapsules, recombinant cells capable of expressing the compound, receptor-mediated endocytosis (see, e.g., Wu and Wu, *J. Biol. Chem.* 262: 4429-4432 (1987)), construction of a nucleic acid as part of a retroviral or other vector, etc. Methods of introduction include intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein of the invention, care must be taken to use materials to which the protein does not absorb.

A preferred method of local administration is by direct injection. Preferably, the compounds of the present invention as well as the nucleic acids/vectors of the present invention is/are complexed with a delivery vehicle to be administered by direct injection into or locally within the area of arteries.

For systemic administration, YopM or its fragments or variants according to the present invention can be complexed to a targeted delivery vehicle.

In another embodiment the pharmaceutical composition may be delivered directly to disease sites in internal organs, body cavities and the like by use of imaging devices used to guide an injecting needle directly to the disease site. The pharmaceutical composition may also be administered to disease sites at the time of surgical intervention.

In another embodiment, the pharmaceutical composition can be delivered in a vesicle, in particular a liposome (Langer, R., *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327).

In yet another embodiment, the composition can be delivered in a controlled release system. In one embodiment, a pump may be used (Sefton, CRC Crit. Ref. Biomed. Eng. 14: 201 (1987); Buchwald et al., Surgery 88: 507 (1980); Saudek et al., N. Engl. J. Med. 321: 574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23: 61 (1983); see also Levy et al., Science 228: 190 (1985); During et al., Ann. Neurol. 25: 351 (1989); Howard et al., J. Neurosurg. 71: 105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Preferably the pharmaceutical composition is in a form, which is suitable for oral, local or systemic administration. In a preferred embodiment the pharmaceutical composition is administered locally, orally or systemically.

It is envisaged that the pharmaceutical compositions of the invention comprise the compounds of the invention in a therapeutically effective amount The term "pharmaceutically acceptable" means approved by a regulatory agency or other generally recognized pharmacopeia for use in animals, and more particularly in humans. The term "carrier" refers to a diluent, adjuvant, excipient, or vehicle with which the therapeutic is administered. Such a carrier is pharmaceutically acceptable, i.e. is non-toxic to a recipient at the dosage and concentration employed. It is preferably isotonic, hypotonic or weakly hypertonic and has a relatively low ionic strength, such as provided by a sucrose solution. Examples of suitable pharmaceutical carriers are described in "Remington's Pharmaceutical Sciences" by E. W. Martin.

Generally, the ingredients are supplied either separately or mixed together in unit dosage form, for example, as a dry lyophilised powder or water free concentrate in a hermetically sealed container such as an ampoule or sachette indicating the quantity of active agent.

Assays, e.g. those described in the Examples, may optionally be employed to help identify optimal dosage ranges. The precise dose to be employed in the formulation will also depend on the route of administration, and the seriousness of the disease or disorder, and should be decided according to the judgment of the practitioner and each patient's circumstances.

The term "administered" means administration of a therapeutically effective dose of the aforementioned composition. By "therapeutically effective amount" is meant a dose that produces the effects for which it is administered, preferably this effect is the downregulation of cytokines, and/or cytokine receptors and/or genes which respond to cytokines and/or cartilage-destroying molecules and/or inhibition of osteoclastogenesis. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The pharmaceutical composition may be used in both human therapy and veterinary therapy. The compounds described herein having the desired therapeutic activity may be administered in a physiologically acceptable carrier to a patient, as described herein. The concentration of the therapeutically active compound in the formulation may vary from about 0.01-100 wt %. The agent may be administered alone or in combination with other treatments.

A typical dose can be, for example, in the range of 0.001 to 1000 µg; however, doses below or above this exemplary range are envisioned, especially considering the aforementioned factors.

It is also envisaged that the pharmaceutical compositions are employed in co-therapy approaches, i.e. in co-administration with other medicaments or drugs, for example other immunosuppressive drugs.

Topical administration of the pharmaceutical composition of the present invention is useful when the desired treatment involves areas or organs readily accessible by topical administration. For a topically application, e.g. to the skin, the pharmaceutical composition is preferably formulated with a suitable paste, ointment, lotion, cream, gel or transdermal patches.

The present invention also provides kits or pharmaceutical packages that can be used in the context of the present invention, for example in the context of administration of the pharmaceutical composition. In one embodiment, a kit/package comprises YopM, a YopM fragment, a YopM variant, or an immunmodulatory domain as defined herein above, in one or more containers. Optionally, the kit/package further comprises a documentation indicating the treatment regimen, use and/or employment of the kits/package components or the pharmaceutical composition.

In a further embodiment of the present invention, YopM, a YopM fragment, a YopM variant and/or an immunmodulatory domain is provided in the form of a living therapeutic. The term "living therapeutic" means that said YopM, a YopM fragment, a YopM variant, and/or an immunmodulatory domain, for example as defined in the context of the pharmaceutical composition, is expressed in a live carrier. Accordingly, the present invention relates to polynucleotides encoding YopM, a YopM fragment, a YopM variant, and/or an immunmodulatory domain as defined herein above which are suitable for expression in a living cell or carrier. The term "live carrier" relates to any appropriate living host cell or virus known to the person skilled in the art. Representative examples of appropriate hosts include, but are not limited to, bacterial cells such as *Escherichia coli* or *Lactobacillus*, fungal cells, such as yeast cells, protozoa, insect cells, or animal cells. Preferably, the term relates to attenuated bacteria, attenuated fungal cells or attenuated protozoa.

In another embodiment the present invention relates to a method of treatment of any of the diseases and medical conditions mentioned herein above, in particular in the context of the pharmaceutical composition as defined herein above, comprising administering YopM, a YopM fragment, a YopM variant, and/or an immunmodulatory domain of YopM, including all modifications as indicated above (cargo; cell specific targeting etc.) to a subject. Preferably, the present invention relates to a method of preventing, ameliorating and/or treating diseases which were exemplified herein elsewhere. Preferably, the subject to be treated is an animal and more preferably, the subject to be treated is a human being.

The present invention also relates to a method for the manufacture of a pharmaceutical composition comprising:
(a) attaching a compound of the invention to a cargo molecule which cargo molecule displays therapeutical activity following delivery into the cells ex vivo and/or in vivo; and optionally
(b) contacting said compound with a pharmaceutically acceptable carrier.

The present invention also relates to the use of a compound of the invention for the manufacture of a pharmaceutical composition. It is envisaged that the compound of the invention is linked/attached to cargo molecules and/or cell-specific targeting entities as described herein. The mentioned pharmaceutical composition is for use in any of the diseases described herein.

In another aspect the present invention relates to a YopM fragment or a YopM variant which essentially comprises one of the alpha helices of YopM, two of the alpha helices of YopM, one of the alpha helices of YopM and 1 to 3 YopM leucine-rich repeats or two of the alpha helices of YopM and 1 to 3 YopM leucine-rich repeats, wherein said YopM fragment or said YopM variant is capable of autopenetrating the cell membrane and of integrating into the cell cytosol without the requirement of additional factors.

The term "essentially comprising" means that the YopM fragment as defined above consists of one of the alpha helices of YopM, two of the alpha helices of YopM, one of the alpha helices of YopM and 1 to 3 YopM leucine-rich repeats or two of the alpha helices of YopM and 1 to 3 YopM leucine-rich repeats and additionally possesses 1, 2, 3, 4, 5, 6, 7, 8, 9 or 10 amino acids at the N- or C-terminus of the fragment. Preferably, these amino acids are amino acids derivable from a YopM sequence as defined herein above, more preferably these amino acids are amino acids derivable from any one of SEQ ID NO: 1 to 8. Even more preferably, these amino acids are derivable from SEQ ID NO: 4.

The terms "YopM", "YopM fragment", "YopM variant", "one of the alpha helices of YopM", "two of the alpha helices of YopM" and "YopM leucine-rich repeat" have been defined herein above. Preferably, YopM has the sequence of SEQ ID NO: 4.

More preferably, the term "one of the alpha helices of YopM" relates to amino acid positions 1 to 51 of SEQ ID NO: 4 or to amino acid positions 52 to 73 of SEQ ID NO: 4; the term "two of the alpha helices of YopM" relates to amino acid positions 1 to 51 of SEQ ID NO: 4 (Helix 1) and to amino acid positions 52 to 73 of SEQ ID NO: 4 (Helix 2), more preferably to amino acid postions 1 to 73 of SEQ ID NO: 4; the term "one of the alpha helices of YopM and 1 to 3 YopM leucine-rich repeats" relates to amino acid positions 1 to 51 of SEQ ID NO: 4 (Helix 1) or to amino acid positions 52 to 73 of SEQ ID NO: 4 (Helix 2) and to amino acid positions 74 to 133 of SEQ ID NO: 4 (leucine-rich repeats 1 to 3 of YopM); and the term "two of the alpha helices of YopM and 1 to 3 YopM leucine-rich repeats" relates to amino acid positions 1 to 51 of SEQ ID NO: 4 (Helix 1) and to amino acid positions 52 to 73 of SEQ ID NO: 4 (Helix 2) in combination with amino acid positions 74 to 133 of SEQ ID NO: 4 (leucine-rich repeats 1 to 3 of YopM), more preferably to amino acid postions 1 to 133 of SEQ ID NO: 4.

In a further embodiment the YopM fragment or a YopM variant which essentially comprises one of the alpha helices of YopM, two of the alpha helices of YopM, one of the alpha helices of YopM and 1 to 3 YopM leucine-rich repeats or two of the alpha helices of YopM and 1 to 3 YopM leucine-rich repeats, as defined herein above, is capable of autopenetrating the cell membrane and of integrating into the cell cytosol and without the requirement of additional factors and is capable of entering the cell nucleus. The term "capable of entering the cell nucleus" means that the protein has the capability to pass across the nuclear membrane of a cell. Preferably, the protein has a nuclear localization sequence, as known to the person skilled in the art. The capability of a YopM fragment or variant to integrate into the nucleus of a cell can be tested by suitable methods and assays known to the person skilled in the art, preferably by nuclear localization assays as described in Hällbrink M., et al., (*Biochem. Biophys. Acta* 1667:222-228 (2004)) and Nare B., et al., (*Anal. Biochem.* 267:390-396 (1999)).

In a preferred embodiment, the capability of a YopM fragment or a YopM variant which essentially comprises one of the alpha helices of YopM, two of the alpha helices of YopM, one of the alpha helices of YopM and 1 to 3 YopM leucine-rich repeats or two of the alpha helices of YopM and 1 to 3 YopM leucine-rich repeats, as defined herein above to enter the cell nucleus is linked to the presence of a nuclear localization sequence (NLS). More preferably, a YopM fragment or a YopM variant in the context of the present invention comprises a YopM NLS as known to the person skilled in the art, e.g. a NLS present in leucine-rich repeats 1 to 3 of YopM, preferably in leucine-rich repeats 1 to 3 of SEQ ID NO: 4. In a preferred embodiment the YopM fragement or variant comprises leucine-rich repeats 1 to 3 of YopM, more preferably it comprises amino acids 74 to 133 of SEQ ID NO: 4.

In another aspect the present invention relates to YopM, a YopM fragment, or a YopM variant, wherein said YopM fragment or YopM variant is capable of autopenetrating the cell membrane and of integrating into the cell cytosol without the requirement of additional factors, wherein said YopM, said YopM fragment, or said YopM variant is linked to at least one cargo molecule, with the proviso that said linkage is not a linkage by a peptide bond with one of the following cargos: β-lactamase, EGFP and adenylate cyclase domain of the *Bordetella pertussis* cyclolysin (CyaA). The terms "YopM", "YopM fragment", "YopM variant", "linked to" and "at least one cargo" have been defined herein above.

In a preferred embodiment, such a linkage is formed by a cleavable linker, or includes a disulfide bond, a peptide bond or a streptavidin-biotin complex, as has been described herein above.

In a further embodiment, such a linkage is a linkage at the C-terminus or the N-terminus of said YopM, said YopM fragment or said YopM variant, as has been described herein above.

In a further preferred embodiment, a cargo molecule to be linked to YopM, a YopM fragment or a YopM variant as defined herein above, comprises at least one compound selected from the nucleic acids, polypeptides, organic molecules, small organic molecules, metals, nano-particles, viruses, modified viruses, viral vectors and plasmids. Terms "nucleic acids", "polypeptides", "organic molecules", "small organic molecules", "metals", "nano-particles", "viruses", "modified viruses", "viral vectors" and "plasmids" have been defined herein above.

Further Items:

The present invention also relates to the use of a *Yersinia* outer protein M (YopM), a YopM fragment, or a YopM variant capable of autopenetrating the cell membrane and of integrating into the cell cytosol of a eucaryoitic cell without the requirement of additional factors, for delivering at least one cargo molecule across said membrane to the cytosol of said cell. It is also envisaged that said YopM fragment or YopM variant comprises at least one of the alpha helices of YopM. It is also contemplated that said YopM fragment or YopM variant comprises additionally at least one YopM leucine-rich repeat. In a preferred embodiment, said YopM fragment or YopM variant comprises leucine-rich repeats 1-3 (LRR1-3) of YopM. It is also contemplated that in the uses above YopM is selected from YopM of a *Yersinia* strain naturally comprising a YopM encoding virulence plasmid, preferably of the species *Yersinia enterocolitica, Yersinia pseudotuberculosis* or *Yersinia pestis*, and more preferably of *Yersinia enterolitica* 8081v, Serotype O:8. It is contemplated that YopM comprises the amino acid sequence of any sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8. It is also contemplated that said fragment or variant comprises an amino acid sequence selected from the group consisting of:

amino acids 1 to 239 of SEQ ID NO: 4;
amino acids 55 to 367 of SEQ ID NO: 4;
amino acids 1 to 73 of SEQ ID NO: 4;
amino acids 52 to 73 of SEQ ID NO: 4;
amino acids 1 to 133 of SEQ ID NO: 4;
amino acids 52 to 133 of SEQ ID NO: 4; and
amino acids 1 to 51 and amino acids 74 to 133 of SEQ ID NO: 4.

The use of any one of the preceding embodiments, wherein said YopM, said YopM fragment or said YopM variant is linked to said at least one cargo molecule is also contemplated. Said linkage may be formed by a cleavable linker, or includes a disulfide bond, a peptide bond or a streptavidin-biotin complex. It is also envisaged that said linkage is a linkage at the C-terminus or the N-terminus of said YopM, said YopM fragment or said YopM variant. In further embodiments said YopM, said YopM fragment or said YopM variant is biotinylated and the cargo molecule is avidin labeled. The use of any one of the preceding embodiments wherein said cargo molecule comprises at least one compound selected from the group consisting of nucleic acids, polypeptides, organic molecules, small organic molecules, metals, nano-particles, viruses, modified viruses, viral vectors, and plasmids is also contemplated. The invention also relates to the use of any one of the preceding embodiments, wherein said cargo molecule comprises at least one compound selected from the group consisting of therapeutic proteins, suicide proteins, tumor suppressor proteins, transcription factors, kinase inhibitors, kinases, regulatory proteins, apoptotic proteins, anti-apoptotic proteins, microbial antigens, viral antigens, bacterial antigens, parasitic antigens, cellular antigens, differentiation factors, immortalisation factors, toxines, enyzmes, antisense constructs, diagnostic imaging or contrast agents, isotopes, dyes, antibacterial agents, antifungal agents, antiviral agents, antiproliferative agents, cytostatics, immunosuppressive agents, histamine receptor antagonists, vitamins, analgesic agents, anti-neoplastic agents, hormones, antiinflammatory agents, adhesion-molecules, receptor-molecules, therapeutic organic molecules, organic inhibitors, peptide inhibitors, and antiaging agents. It is also envisaged that said YopM, said YopM fragment or said YopM variant is additionally linked to a cell-specific targeting agent. Said cell-specific targeting agent may be selected form the group consisting of CD antigens, anti-CD antibodies, molecular danger signals, TLRs, bacterial toxins, vascular homing peptides, tumor homing peptides, and DEC-205. The present invention also relates to a pharmaceutical composition comprising YopM, a YopM fragment or a YopM variant, wherein said YopM fragment or YopM variant is capable of autopenetrating the cell membrane and of integrating into the cell cytosol without the requirement of additional factors. A pharmaceutical composition comprising YopM, a YopM fragment, or a YopM variant, wherein said YopM fragment or YopM variant is capable of autopenetrating the cell membrane and of integrating into the cell cytosol without the requirement of additional factors, for the regulation of inflammatory reactions of the immune system, the treatment of diseases caused by autoimmunity of the host, the treatment of inflammation, chronic inflammation, gastroenteritis, chronic gastritis, inflammatory bowel diseases (IBD), Colitis ulcerosa, psoriasis, allergic reactions, Morbus Crohn, rheumatoid arthritis or for suppressing the immune system, is also envisaged. The use of YopM, a YopM fragment, or a YopM variant, wherein said YopM fragment or YopM variant is capable of autopenetrating the cell membrane and of integrating into the cell cytosol without the requirement of additional factors, for the regulation of inflammatory reactions of the immune system, the treatment of diseases caused by autoimmunity of the host, the treatment of inflammation, chronic inflammation, gastroenteritis, chronic gastritis, inflammatory bowel diseases (IBD), Colitis ulcerosa, psoriasis, allergic reactions, Morbus Crohn, rheumatoid arthritis, or for suppressing the immune system is likewise envisaged. The pharmaceutical composition of any one of the preceding embodiments or the use of any one of the preceding embodiments wherein said YopM, said YopM fragment or said YopM variant is provided in the form of a living therapeutic, is also envisaged. Preferably, said YopM, said YopM fragment or said YopM variant is expressed in an attenuated virus, an attenuated bacteria or a protozoa. The pharmaceutical composition of any one of the preceding embodiments, or the use of any one of the preceding embodiments, wherein said YopM, said YopM fragment or said YopM variant is linked to a cargo molecule as defined above is also envisaged. The present invention also relates to a YopM fragment or a YopM variant, essentially comprising one of the alpha helices of YopM, two of the alpha helices of YopM, one of the alpha helices of YopM and 1 to 3 YopM leucine-rich repeats or two of the alpha helices of YopM and 1 to 3 YopM leucine-rich repeats, wherein said YopM fragment or said YopM variant is capable of autopenetrating the cell membrane and of integrating into the cell cytosol without the requirement of additional factors. A YopM, a YopM fragment or a YopM variant, wherein said YopM fragment or YopM variant is capable of autopenetrating the cell membrane and of integrating into the cell cytosol without the requirement of additional factors wherein said YopM, said YopM fragment or said YopM variant is linked to at least one cargo molecule, with the proviso that said linkage is not a linkage by a peptide bond with one of the following cargos: β-lactamase, EGFP and adenylate cyclase domain of the Bordetella pertussis cyclolysin (Cya), is also envisaged. Said linkage may be formed by a cleavable linker, or includes a disulfide bond, a peptide bond or a streptavidin-biotin complex. Said linkage may be a linkage at the C-terminus or the N-terminus of said YopM, said YopM fragment or said YopM variant. Said cargo molecule may comprise at least one compound selected from the nucleic acids, polypeptides, organic molecules, small organic molecules, metals, nano-particles, viruses, modified viruses, viral vectors and plasmids. Said cargo molecule may comprises at least one compound selected from the group consisting of therapeutic proteins, suicide proteins, tumor suppressor proteins, transcription factors, kinase inhibitors, kinases, regulatory proteins, apoptotic proteins, anti-apoptotic proteins, microbial antigens, viral antigens, bacterial antigens, parasitic antigens, cellular antigens, differentiation factors, immortalisation factors, toxines, enyzmes, antisense constructs, diagnostic imaging or contrast agents, isotopes, dyes, antibacterial agents, antifungal agents, antiviral agents, antiproliferative agents, cytostatics, immunosuppressive agents, histamine receptor antagonists, vitamins, analgesic agents, anti-neoplastic agents, hormones, antiinflammatory agents, adhesion-molecules, receptor-molecules, therapeutic organic molecules, organic inhibitors, peptide inhibitors and antiaging agents. Said YopM fragment or said YopM variant may additionally be linked to a cell-specific targeting agent. Said cell-specific targeting agent may be selected form the group consisting of CD antigens, anti-CD antibodies, molecular danger signals, TLRs, bacterial toxins, vascular homing peptides, tumor homing peptides and DEC-205.

It is to be understood that this invention is not limited to the particular methodology, protocols, proteins, bacteria, vectors, reagents etc. described herein as these may vary. It is also to be understood that the terminology used herein is for the purpose of describing particular embodiments only, and is not intended to limit the scope of the present invention that will be limited only by the appended claims.

Several documents are cited throughout the text of this specification. Each of the documents cited herein (including all patents, patent applications, scientific publications, manufacturer's specifications, instructions, etc.), whether supra or infra, is hereby incorporated by reference in their entirety. Nothing herein is to be construed as an admission that the invention is not entitled to antedate such disclosure by virtue of prior invention.

It must be noted that as used herein and in the appended claims, the singular forms "a", "an", and "the", include plural referents unless the context clearly indicates otherwise. Thus, for example, reference to "a polypeptide" includes one or more of such polypeptides, and reference to "the method" includes reference to equivalent steps and methods known to those of ordinary skill in the art that could be modified or substituted for the methods described herein.

The figures show:

FIG. 1 shows the domain organization and functional regions of YopM. In particular, the figure shows type-III secretion (S) and translocation (T) signal required by the T3SS [N-terminal residues aa 34-40 (S) & aa 40-100 (T), (Ghosh 2004)] and NLS, nuclear localisation signal, NLS-I: three N-terminal LRRs and NLS-II: 32 C-terminal residues of YopM.

Figure 2:
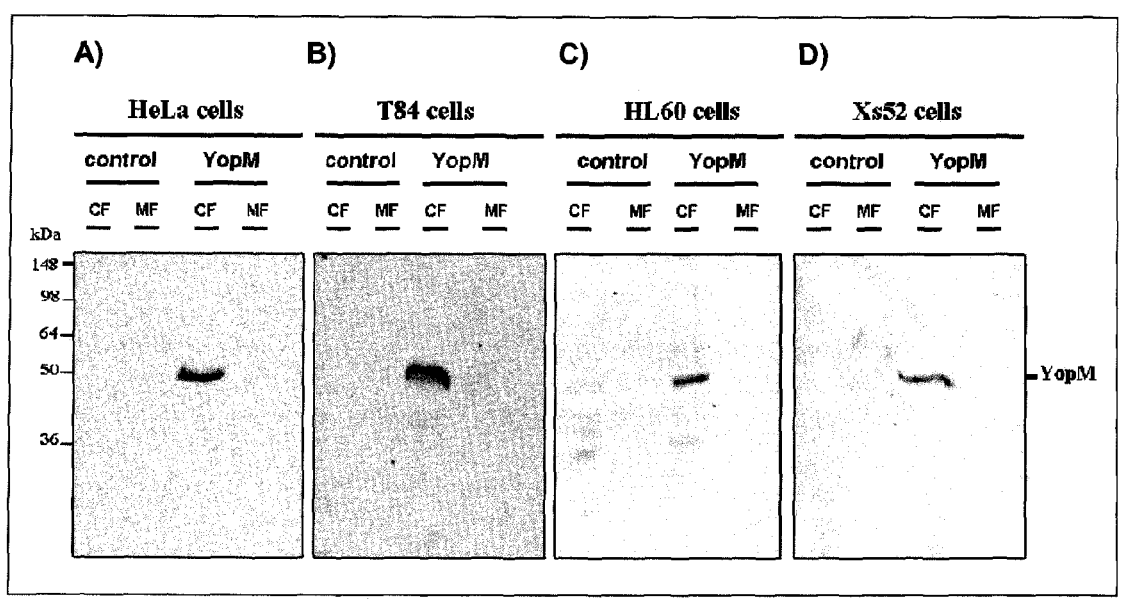

FIG. 2 shows the detection of YopM in eukaryotic cells. In particular, the figure relates to HeLa-(A), T84-(B), HL60-(C), and XS52-cells (D), which were incubated for 30 min at 37° C. with recombinant YopM or medium (control) and fractionated into soluble cytoplasmic proteins (CF) and into membrane proteins (MF). Precipitated proteins were separated by SDS-PAGE, blotted and probed with polyclonal YopM antibodies. Molecular masses (kDa) of standard proteins are indicated.

Figure 3:
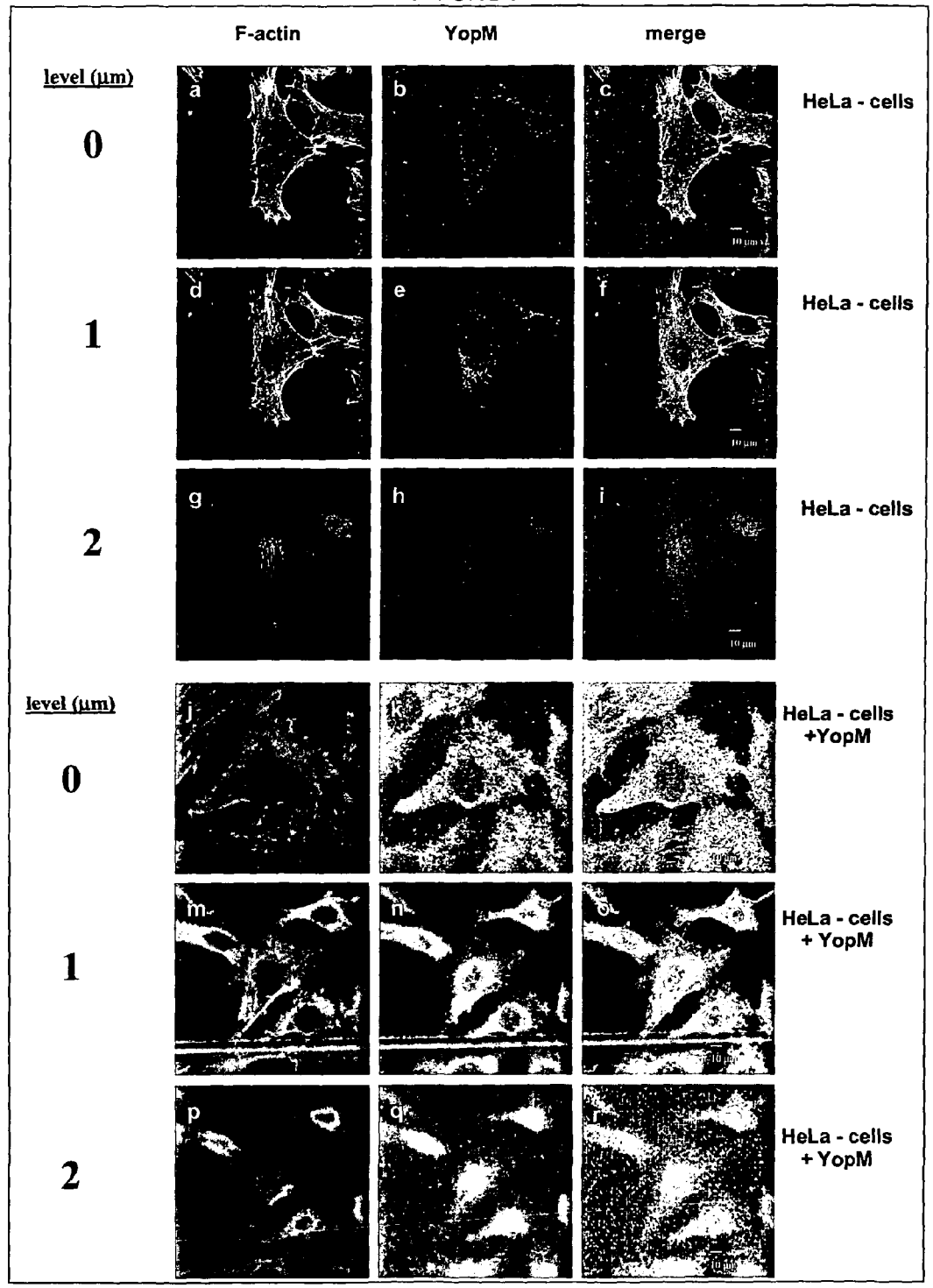

FIG. 3 shows the autopenetration of recombinant YopM into the host cell cytoplasm of HeLa cells. HeLa cells were incubated with recombinant YopM for 30 min at 37° C. (j-r), washed and incubated again with medium over-night (pulse-chase). Together with untreated cells as a control for the immunostaining (a-i), all cells were prepared for immunofluorescence microscopy. YopM was visualized with polyclonal anti-YopM primary antibodies and Cy2-conjugated secondary antibodies (green; b, e, h, k, n, q). F-actin was labelled with phalloidin/Texas-Red (red; a, d, g, j, m, p). Merged images of YopM and actin are indicated (c, f, i, l, o, r). Confocal scanning microscopy levels; level 0 corresponds to overview of the cell (a, b, c, j, k, l), scanning interval of 1 µm, level 1: (d, e, f, m, n, o) and level 2: 2 µm (g, h, i, p, q, r; magnification ×100).

FIG. 4 gives a schematic overview of the different truncated YopM versions (A) and detection of theses constructs in HeLa cells (B). The amino acids represented in the truncated YopM versions are indicated corresponding to full length YopM (1-367 aa). HeLa cells were incubated for 30 min at 37° C. with recombinant proteins of the different truncated YopM versions and fractionated into soluble cytoplasmic (CF) and membrane proteins (MF) (B). Precipitated proteins were separated by SDS-PAGE, blotted and probed with anti-His-tag antibodies or polyclonal YopM antibodies. Equal amounts of protein were loaded in each lane, and for control for contamination of MF with cytosolic proteins, both fractions were analysed for cytosolic β-actin with a monoclonal antibody raised against β-actin (B).

Figure 5:
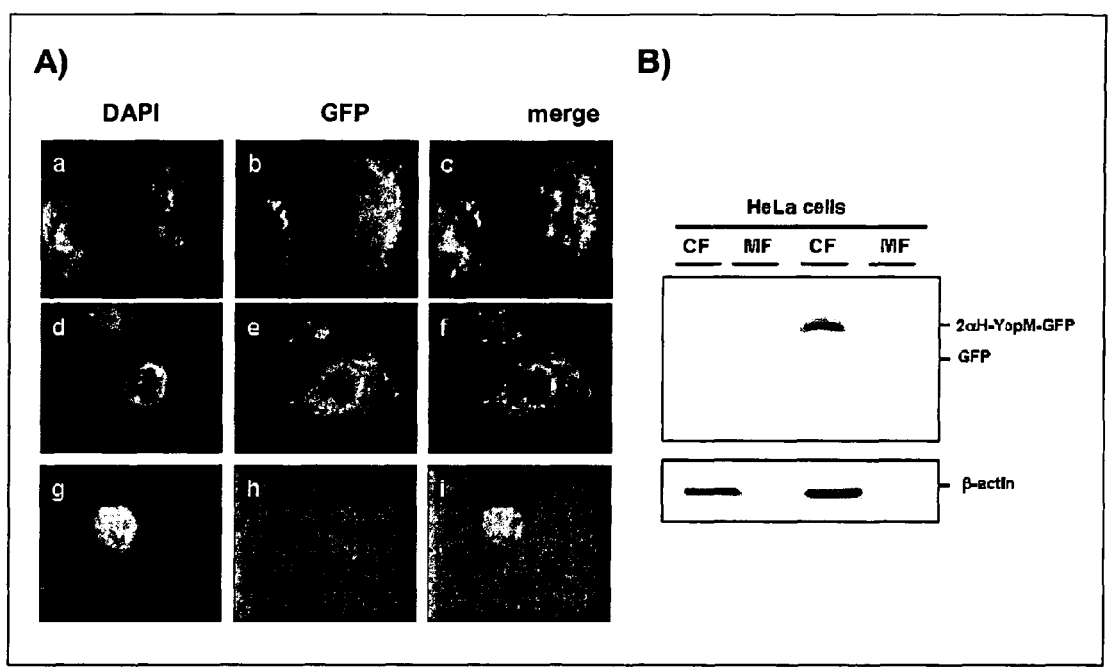
Figure 6:
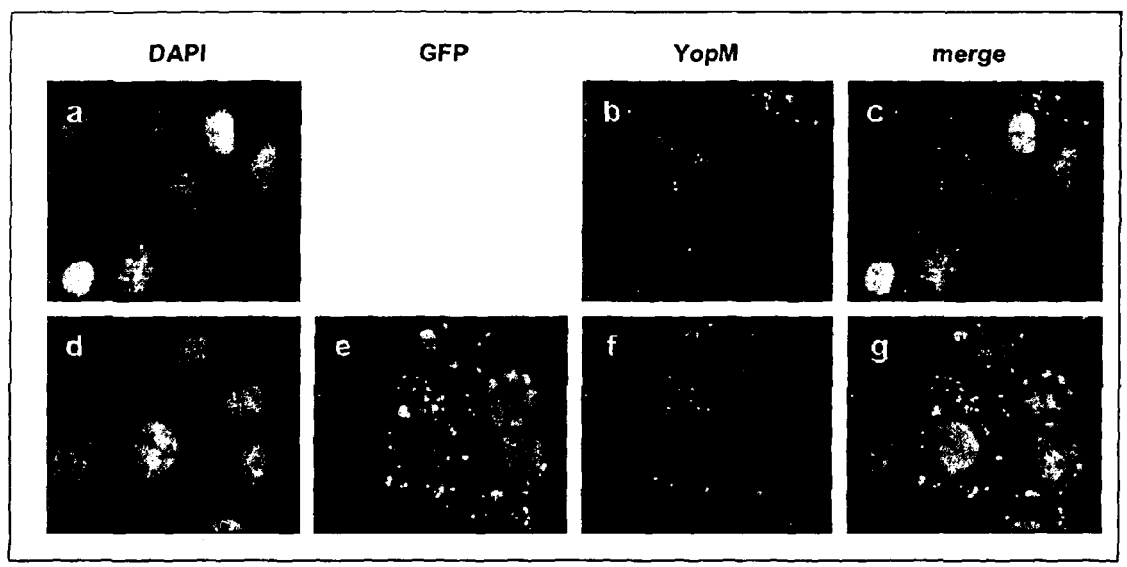

FIG. 5 shows the cargo-transport of 2αH-GFP by the amino-terminal helices of YopM. The ability of 2αH-GFP to autopenetrate host cell membranes was analyzed by fluorescence microscopy (A) and Western blotting (B). A: HeLa cells were incubated with recombinant 2αH-GFP (A: a, b, c) and with recombinant GFP (A: g, h, i) for 30 min at 37° C. In addition, HeLa cells were incubated with recombinant 2αH-GFP (A: d, e, f) for 5 min at 4° C., washed and incubated again with medium for 45 min at 37° C. (pulse-chase). Subsequently, HeLa cells were washed, fixed and permeabilized. DNA of HeLa cells was stained DAPI. Merged images of 2αH-GFP or GFP and DAPI are indicated (A: c, f, i). B: HeLa cells were incubated for 30 min at 37° C. with recombinant 2αH-GFP and GFP. After treatment, HeLa cells were fractionated into soluble cytoplasmic (CF) and into membrane fraction (MF). Precipitated proteins were separated by SDS-PAGE, blotted and probed with anti-His-tag antibodies. Equal amounts of proteins were loaded in each lane and for control of contamination of MF with cytosolic proteins, both fractions were analyzed for cytosolic β-actin with a β-actin specific monoclonal antibody.

FIG. 6 demonstrates that 2αH-GFP follows the same intracellular route as YopM. HeLa cells were incubated with recombinant YopM alone (a, b, c) or together with 2αH-GFP (d, e, f, g) for 5 min at 4° C., washed and incubated subsequently with medium for 15 min at 37° C. (pulse-chase). HeLa cells were then washed, fixed and permeabilized. DNA of HeLa cells were stained with DAPI. Merged images of 2αH-GFP, YopM and DAPI are indicated (c, g).

Figure 7:
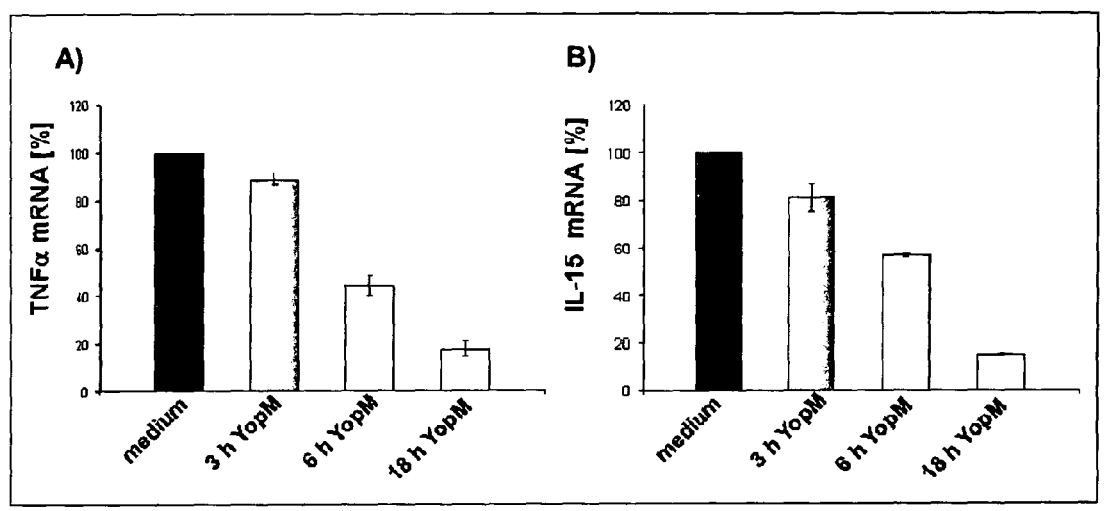

FIG. 7 shows the time course effect of YopM on induction of mRNA for TNFα (A) and IL-15 (B) in HL60 cells. Cells were differentiated into macrophages and incubated for 3 h, 6 h or 18 h with recombinant YopM. After treatment, cells were lysed and total RNA was extracted, reverse transcribed and analysed by quantitative Real Time RT-PCR using specific primers for TNFα and IL-15. The mRNA level of medium-treated cells was set as 100%.

Figure 8:
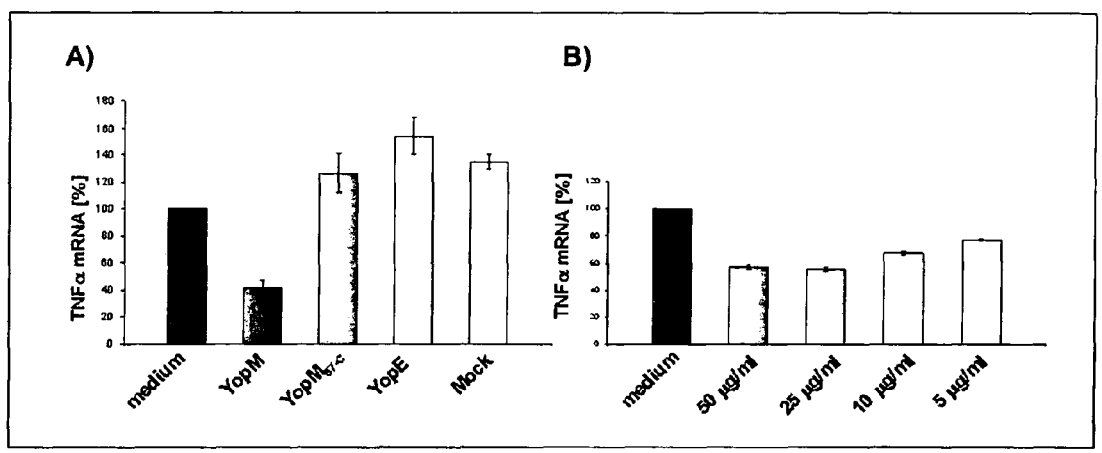

FIG. 8 shows under (A) the effect of YopM, YopM$_{87-C}$, YopE and Mock treatment on transcription of TNFα in HL60 cells. Under (B) the influence of different amounts of YopM (50, 25, 10 and 5 µg/ml) on transcription of TNFα in HL60 cells is illustrated. Cells were differentiated into macrophages and incubated for 6 h with protein. After treatment, cells were lysed and total RNA was extracted, reverse transcribed and analyzed by quantitative Real Time RT-PCR using specific primers for TNFα. The mRNA level of medium-treated cells was set as 100%.

Figure 9:
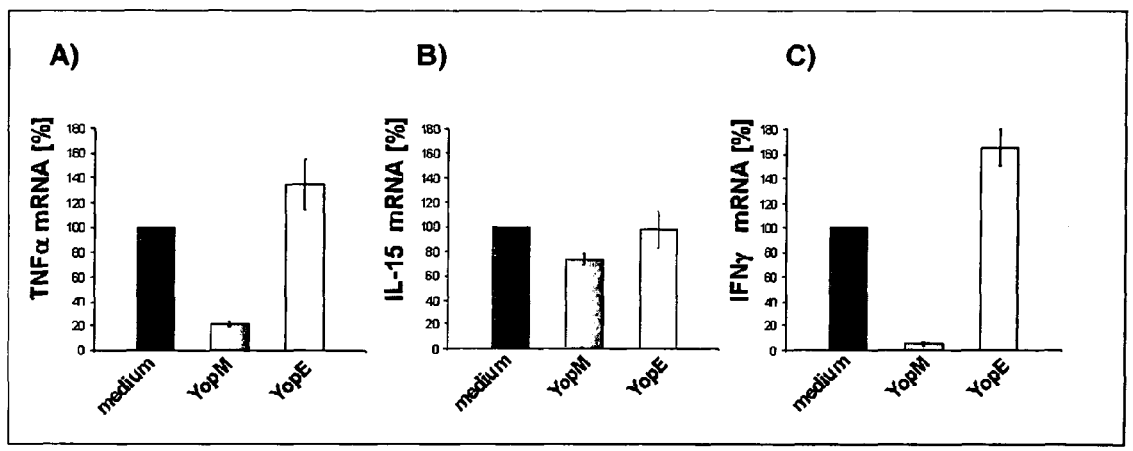

FIG. 9 shows the effect of YopM on induction of mRNA for TNFα (A), IL-15 (B) and IFNγ (C) in HeLa cells. Cells were incubated for 6 h with recombinant YopM and YopE (control). After treatment, cells were lysed, and total RNA was extracted, reverse transcribed and analysed by quantitative Real Time RT-PCR using specific Primers for TNFα, IL-15 and IFNγ. The mRNA level of medium-treated cells was set as 100%.

Figure 10:
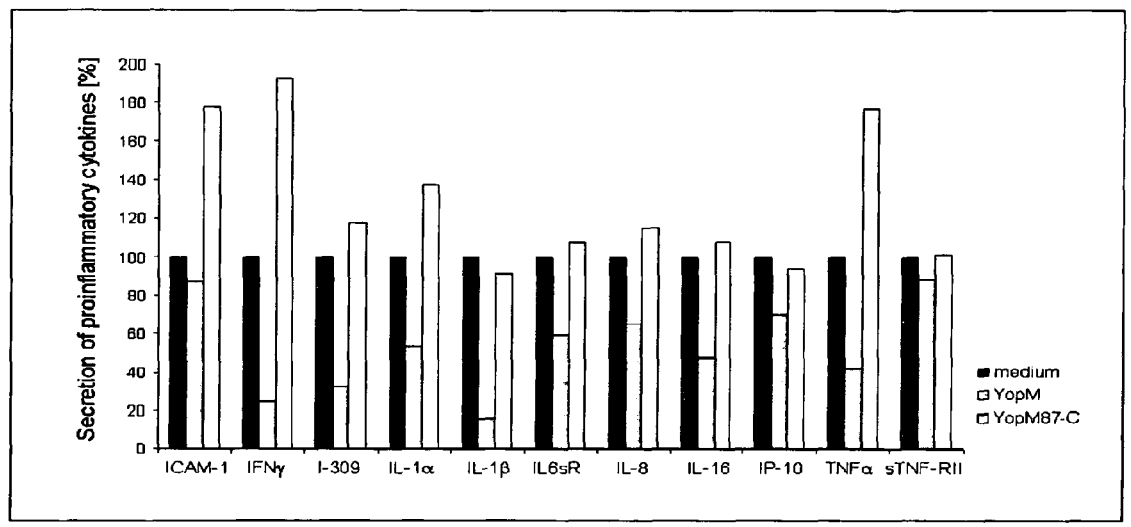

FIG. 10 shows the effect of YopM and YopM$_{87-C}$ on the secretion of proinflammatory cytokines in HL60 cells. Cells were differentiated into macrophages and incubated for 6 h with protein. After treatment, supernatants were analysed using the RayBio® Human Inflammation Antibody Array for proinflammatory cytokines. The amount of cytokines in medium-treated cells was set to 100%.

Figure 11:
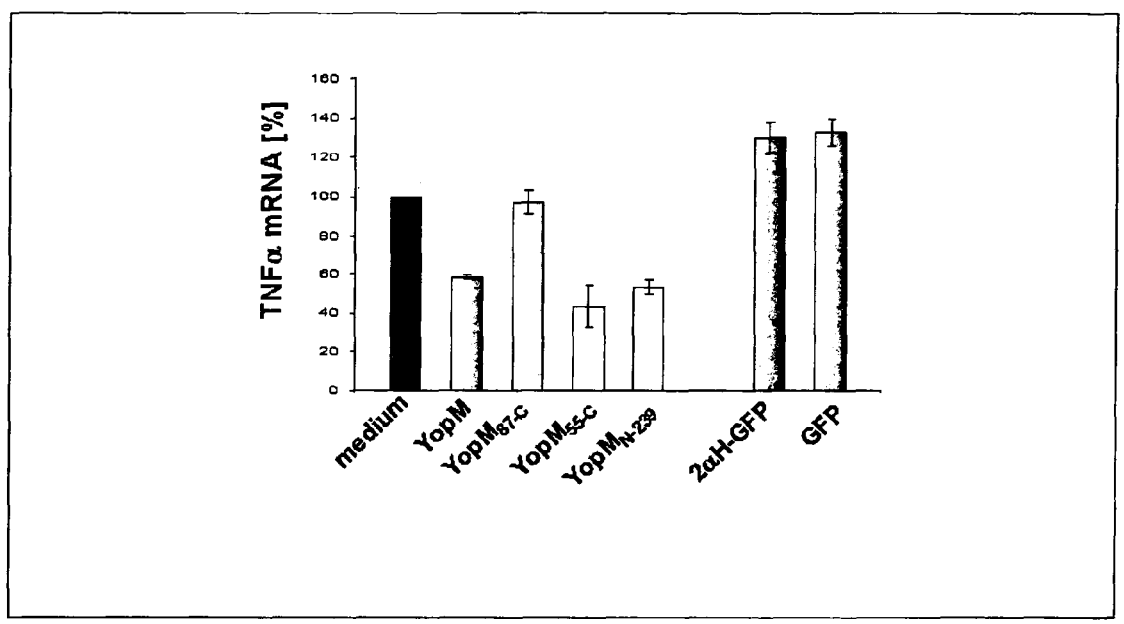

FIG. 11 shows the effect of several truncated versions of YopM on gene transcription of TNFα in HL60 cells. Cells were differentiated into macrophages and incubated for 6 h with YopM, YopM$_{87-C}$, YopM$_{55-C}$, YopM$_{N-239}$ (2.2), 2αH-GFP and GFP (2.3). After treatment, cells were lysed, and total RNA was extracted, reverse transcribed and analysed by qRT-PCR using specific primers for TNFα. The mRNA level of medium-treated cells was set as 100%.

Figure 12:
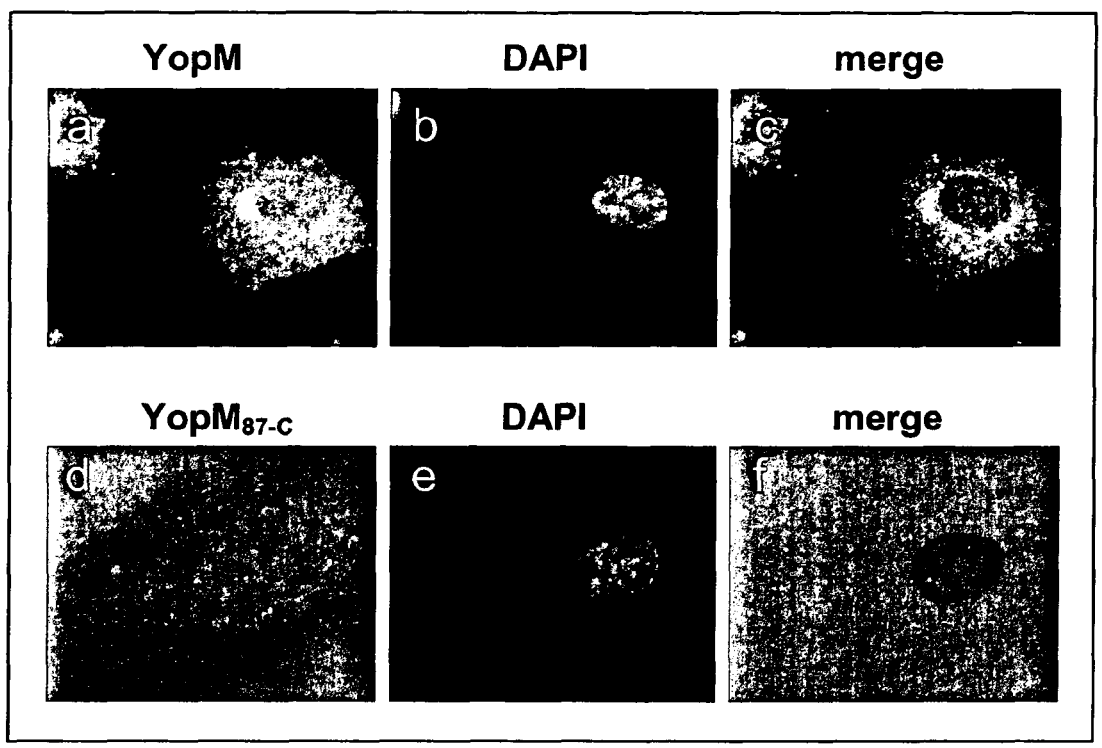

FIG. 12 shows the detection of YopM in the cytoplasm of human intestinal microvascular endothelial cells (HIMEC). HIMEC cells were incubated with recombinant YopM (a-c) or the non-penetrating derivative YopM$_{87-C}$ (d-f) for 1 h. Subsequently, cells were washed, fixed and prepared for immunofluorescence microscopy. YopM was visualised with polyclonal anti-YopM primary antibodies and Cy2-conjugated secondary antibodies (a, d). DNA of HIMEC cells was stained DAPI (b, e). Merged images of YopM and DAPI are indicated (c, f). Magnification ×100.

Figure 13:
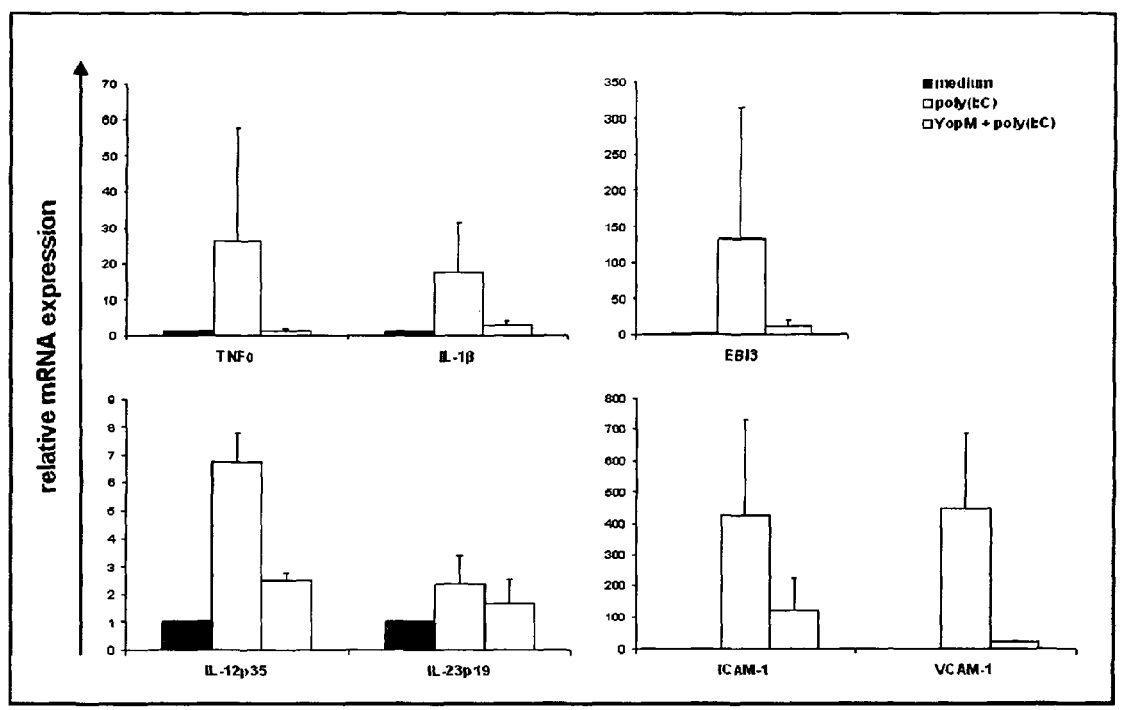

FIG. 13 shows the effect of YopM on poly(I:C)-induced mediators of immune responses in HIMECs. Cells were pre-incubated for 3 h with recombinant YopM and subsequently stimulated for an additional 16 h with poly(I:C) (100 µg/ml). Untreated (medium) and poly(I:C)-induced HIMECs were used as controls. After treatment, cells were washed, lysed, and total RNA was extracted. After reverse transcription, the cDNA was analysed by quantitative RT-PCR using specific Primers for TNFα, IL-β, IL12p35, IL23p19, EBI3, ICAM-1, and VCAM-1. The mRNA level of medium-treated cells was set as 1.

FIG. 14 shows autopenetration of YopM-Cy3 into rheumatoid arthritis synovial fibroblasts (RASFs). RASFs were incubated with Cy3-conjugated YopM for 30 min (a-c) and 1 h (d-f). Subsequently, cells were washed, fixed and prepared for fluorescence microscopy. YopM-Cy3 appears red (a, d). DNA of RASFs was stained by Draq5 (b, e). Merged images of YopM and Draq5 are indicated (c, f).

FIG. 15 shows the influence of YopM on the production of IL-6 and matrix-degrading molecules (MMP-1, MMP-3). RASFs were incubated with TNFα (10 ng/ml) and recombinant YopM for 6 h. In addition, RASFs were co-incubated with TNFα (10 ng/ml) and YopM for 6 h and 8 h. The production of IL-6, MMP-1 and MMP-3 by RASFs after TNFα and YopM treatment was determined using ELISA of the culture supernatant.

FIG. 16 shows the effect of YopM on osteoclastogenesis induced by RANKL in mouse bone marrow cells. The bone marrow cells were isolated from the cut shafts of mouse femurs and tibias, and osteoclastogenesis was induced by RANKL (20 ng/ml) and M-CSF (25 ng/ml) at a supra-optimal density of cells ($4.8 \times 10^5$ cells). In addition to M-CSF and RANKL treatment, cells were co-incubated with recombinant YopM and prepared for microscopy. Tartrate-resistant acid phosphatase (TRAP) was stained with Fast Garnett (leukocyte acid phosphatase kit, Sigma Diagnostics) in the presence of tartrate for 30 min at 37° C. (A) Light microscopy images were relayed to a computer via a colour camera and recorded using Histolab software. All images were taken from the central region of the wells. (B) TRAP-positive (TRAP$^+$) multinuclear osteoclasts were identified and quantified using light microscopy. Counted cells were differentiated into small (pre-) osteoclasts (2-10 nuclei) and larger osteoclasts (>10 nuclei) by their number of nuclei.

Figure 17:
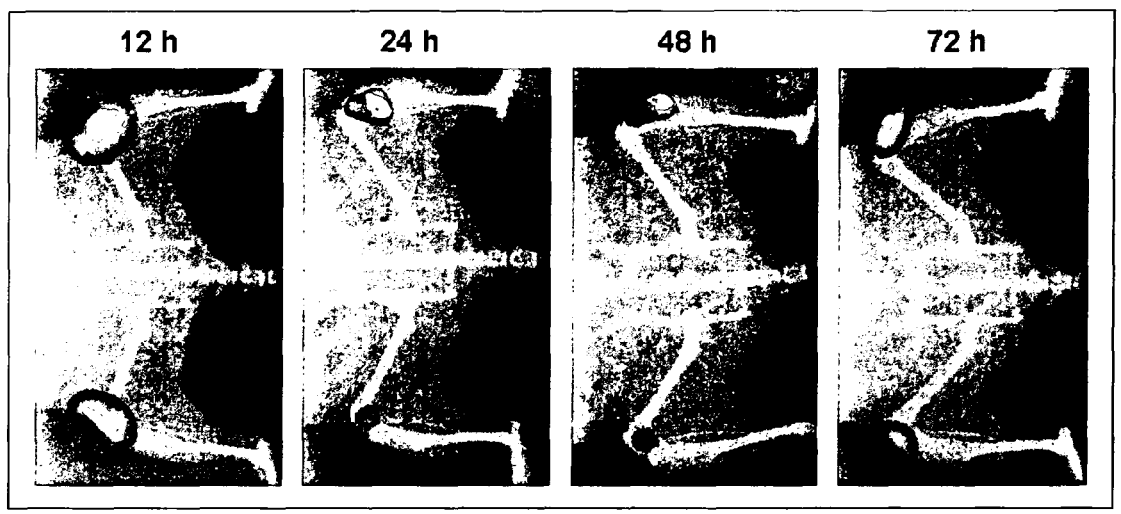

FIG. 17 shows Fluorescence Reflection Imaging (FR1) of mice after intra-articular (i.a.) injection of Cy5-conjugated YopM. YopM was Cy5-conjugated and injected i.a. into the joints of the hind leg of a sleeping hairless mouse. FR1 images after 12 h, 24 h and 48 h were overlayed with a radiograph of the mouse (acquisition time: 30 s; Exz/Em 680/730 nm).

FIG. 18: HeLa cells were incubated for 5 min-3 h (a-e) with gold-labelled recombinant YopM and prepared for electron microscopy. Early after incubation the gold-labelled YopM could be detected bound to the surface (5 min; a) and appeared to be associated with vesicular structures (15 min-1 h; b-d) as well as free in the cytosol at later time points of incubation (3 h; e, indicated by arrows), magnification 40.000×. Au 6 nm; ECM: extracellular matrix, PM: plasma membrane, NE: nuclear envelope, NP: nuclear plasma, MVB: multi-vesicular bodies.

Figure 19:
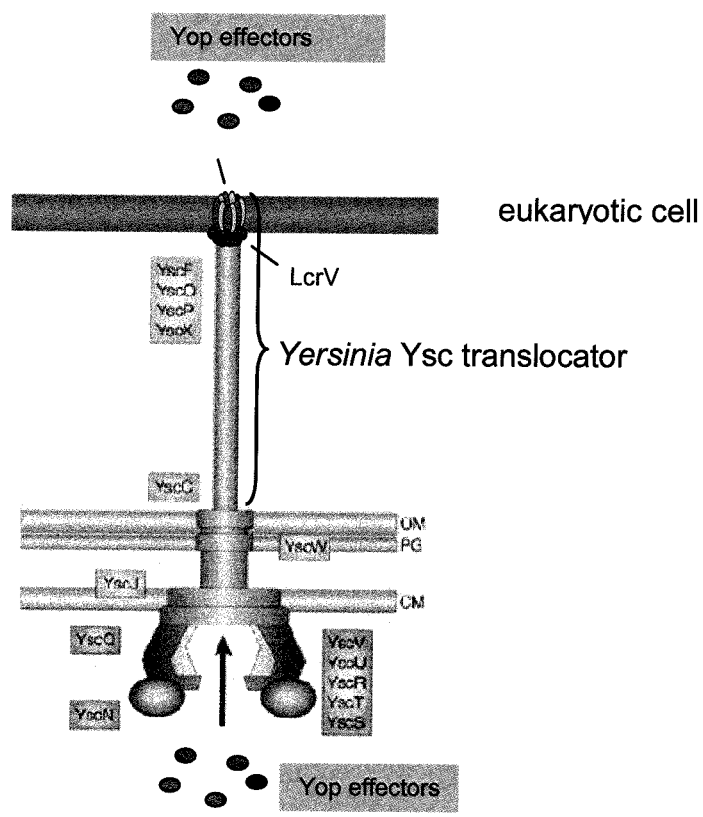

FIG. 19 depicts the *Yersinia* injectisome including the Yop translocators, modified according to Cornelis, G. R. (*Nat. Rev. Mol. Cell Biol.* 3, 742-754 (2002)),

EXAMPLE 1

T3SS Independent Autopenetration of YopM into the Host Cell Cytoplasm

According to a putative extracellular function of YopM, it was recently suggested that apolarly secreted YopM and also recombinant YopM might be able to penetrate host cell membranes independently of *Yersinia's* T3SS. To further analyse bacterial contact-independent delivery of YopM into the host cell cytoplasm, HeLa cells were incubated with recombinant YopM and subsequently separated into cytosolic (CF) and membrane protein fractions (MF), TCA-precipitated, separated by SDS-PAGE and analyzed by Western blotting.

After 30 min of incubation of HeLa cells with recombinant YopM, the protein could be detected in the CF but not in the MF (FIG. 2: A). Employing T84 epithelial cells as well as HL60- and XS52-cells, this process ('autopenetration') of YopM could be confirmed, showing that this is an intrinsic ability of YopM which is not restricted to certain eukaryotic cell types.

As shown for HeLa cells, recombinant YopM can only be detected in CF (not MF) in all analyzed cell lines (FIGS. 2 B, C, and D), indicating that the type III secretion system is not required for the integration of YopM into the host cell cytoplasm. Furthermore, this effect seems not to be facilitated by specific conditions or features of a single cell line that might enable YopM to penetrate host cell membranes of certain cell types. Similarly, YopM can be detected by immunofluorescence microscopy in cells incubated with recombinant YopM (FIG. 3). To this end, HeLa cells were incubated with recombinant YopM for 30 min, and then incubated with infection medium for 3 h. Then, cells were washed with D-PBS/Mg$^{2+}$. This is followed by an acid-wash with 0.2 M glycine, pH 2.0. After fixing, cells were permeabilized and incubated overnight with 5% goat serum and 1% BSA to block unspecific binding sites. The next day, cells were incubated with polyclonal YopM antiserum for 1 h, washed with PBS, and then with Cy2-labelled secondary antibody. To visualize the cytoskeleton of the HeLa cells they were stained with phalloidin-Texas Red. Subsequently, cells were analyzed by confocal scanning microscopy.

When examining YopM's cytoplasmic localization in the host cell after treatment of HeLa cells with recombinant protein by immunofluorescence microscopy, YopM appears to be distributed all over the cytoplasm and also seems to be localized inside the nucleus of the host cell (FIG. 3: level 0 overview: j, k, l). Moreover, YopM accumulated around the nucleus of the target cell (FIG. 3: level 1; m, n, o; level 2; p, q, r).

In order to determine YopM's intracellular localization, electron microscopy (EM) with gold-labelled YopM was done (FIG. 3B). Early after incubation of HeLa cells (5-15 min at 37° C.), YopM-Au was detected bound to the cell surface (FIG. 3 B; a) and also appeared to be associated with vesicles in the cytosol (FIG. 3B; b). Later after incubation (15-60 min), YopM-Au can be found in multi-vesicular bodies (MVB; FIG. 3B; c), which are a typical form of late endosomes (LE). Interestingly, we often observed YopM-associated structures without any distinct membrane (FIG. 3B; d). Moreover the vesicle membranes seemed to be dissolved, allowing YopM to escape from the endosomal compartment. Finally, YopM-Au was detected (3 h) free in the cytosol, as well as inside the nucleoplasma (FIG. 3B; f, indicated by black arrows). This indicates, that YopM initially enters host cells via a vesicle-associated mechanism before entering the cytoplasm at later time points, a process we termed autopenetration. After autopenetration, YopM appears free in the cytosol, accumulates in perinuclear regions and can enter the nucleus.

EXAMPLE 2

The N-Terminal α-Helices of YopM Mediate Autopenetration into the Host Cell Cytoplasm To further analyze and localize domains within YopM that mediate T3SS-independent autopenetration of YopM into the host cell cytoplasm, different N- or C-terminally truncated versions of recombinant His-tagged YopM were constructed (FIG. 4A). The cloning of YopM, YopM$_{N-239}$, YopM$_{172-C}$ and YopM$_{87-C}$ and the expression and purification of recombinant proteins has been previously described (Heusipp et al., 2006). YopM$_{55-C}$ was similarly constructed using primer pairs to delete amino acid (aa) residues 1 to 55 (FIG. 4A). Deletion of the second α-helix of YopM was achieved by inverse PCR with pET-yopM as template (FIG. 4A; YopM$_{\Delta 2\alpha H}$).

HeLa cells were incubated with the recombinant His-tagged YopM derivatives for 30 min and afterwards separated into cytosolic and membrane fractions. CF and MF of HeLa cells were analysed for the presence of YopM derivatives by Western blotting. As shown in FIG. 4B, YopM$_{N-239}$ missing the C-terminal aa residues 240-367 is still able to penetrate the host cell membrane and integrate into the cell cytosol, excluding a role of the C-terminus of the protein in autopenetration. In contrast, YopM$_{172-C}$ missing the N-terminal aa residues 1-171 and YopM$_{87-C}$ missing the N-terminal aa residues 1-86, cannot be detected in the cytosol of the cell (FIG. 4B). The fact that these derivatives are no longer able to penetrate membranes narrows down the potential autopenetration domain to the N-terminus of YopM. Moreover, the loss of the ability of YopM$_{87-C}$ to autopenetrate, directs the attention to the N-terminally located α-helices of the protein. Interestingly, the deletion of just one of these helices (FIG. 4A; YopM$_{55-C}$ and YopM$_{\Delta 2\alpha H}$) did not result in the loss of the autopenetration ability of one of the derivatives. YopM$_{55-C}$ and also YopM$_{\Delta 2\alpha H}$ can still be detected in the cell cytosol of HeLa cells (FIG. 4B). This might indicate that the helices work synergistically in enabling YopM to penetrate the membranes and enter into the host cell cytosol.

EXAMPLE 3

The N-Terminal α-Helices of YopM can be Used for Delivering Cargos

YopM's ability to autopenetrate host cell membranes was identified in the experiments described in Examples 1 and 2. Similar functions have been described for a group of proteins whose members are termed "cell penetrating peptides" (CPP). CPPs have been used to non-invasively transport small cargos like oligonucleotides and peptides into living cells. Recently, peptide-mediated cellular delivery of whole proteins was demonstrated. Transportan derived from the Tat protein of the HI-virus as well as the Antennapedia protein of *Drosophila melanogaster*, are able to deliver proteins into living cells (see: Dietz and Bähr, 2003).

The analysis of the T3SS-independent autopenetration of YopM into the host cell cytoplasm implicates the N-terminal α-helices of the protein as being involved in autopenetration. In analogy of previous studies with CPPs, it was investigated whether a cellular delivery of whole proteins might be possible by using the N-terminal α-helices of the YopM protein as cargo transporters. To this end GFP was used as a model protein to confirm that the N-terminal α-helices of YopM can indeed mediate the transduction of a foreign proteins into eukaryotic cells.

A corresponding construct was generated comprising both α-helices fused to GFP. To construct a vector for the expression of a 2αH-GFP fusion protein, an inverse PCR with pET-yopM as template was performed, resulting in the vector pET-2αH harbouring only the coding regions for the amino-terminal helices of YopM. The gene for gfp was amplified by PCR and inserted into the pET-2αH vector for protein expression. Proteins were isolated, purified and concentrated via carboxy-terminal 6×His tag by affinity chromatography.

To investigate whether the resulting fusion protein 2αH-GFP can autopenetrate the membranes of the host cells, HeLa cells were incubated with recombinant proteins 2αH-GFP and GFP for 30 min at 37° C. and analyzed by fluorescence microscopy (FIG. 5A) and Western blotting (FIG. 5B). In contrast to GFP, which alone is not able to enter the host cell cytoplasm, the fusion protein 2αH-GFP can penetrate the host cell membrane and accumulate inside the host cell cytoplasm, as shown by Western blotting analysis after cell fractionation of GFP- and 2αH-GFP-treated HeLa cells (FIG. 5B). Furthermore, the immunofluorescence microscopy images show that the fusion protein is localized in the cytoplasm and seems to appear in vesicle-like structures inside the cytosol (FIG. 5A: a, b, c). This cannot be observed in GFP-treated HeLa cells (FIG. 5A: d, e, f). Interestingly, after "pulse-chase" treatment of HeLa cells with 2αH-GFP at 4° C. (leading to an accumulation of the protein at the plasma membrane of target cells caused by inhibition of the energy dependent uptake mechanism), the mentioned vesicle-like structures containing 2αH-GFP shift more towards the cell center and finally concentrate in the perinuclear region, but do not appear inside the nucleus (FIG. 5A: d, e, f). This indicates that the fusion protein 2αH-GFP after autopenetration of the cytoplasmic membrane follows the same intracellular route as recombinant YopM. This observation suggests that the amino-terminal helices of YopM might encode the information for intracellular transport. This conclusion is nicely underlined by co-localization experiments after "pulse-chase" treatment of HeLa cells with 2αH-GFP and YopM at 4° C. (FIG. 6). While recombinant YopM also appears in vesicle-like structures after penetration of host cell membranes (FIG. 6: a, b, c), both proteins co-localize in these vesicle-like structures during combined incubation of HeLa cells with YopM and 2αH-GFP (FIG. 6: d, e, f, g).

Together these results demonstrate that the N-terminal α-helices of YopM can deliver cargo proteins into the cytoplasm of target cells and thus represent CPP motifs which might be used as new tools to deliver cargos into eukaryotic cells as had already been described for other CPPs.

EXAMPLE 4

Autopenetrating YopM Targets the Innate Immune System

The innate immune system comprises the cells and mechanisms that in a non-specific manner defend the host from infection by pathogens. The cells and components of the innate immune system recognize and respond to pathogens in a generic way that unlike the adaptive immune system, does not confer long-lasting or inducible immunity to the host. The major functions of the vertebrate innate immune system include the recruitment of immune cells to sites of infection and inflammation through cytokines. Cytokines and chemokines are redundant secreted proteins involved in growth stimulation, differentiation, and activation that regulate and determine the nature of the immune responses, control immune cell trafficking, and the cellular arrangement of immune organs (Borish and Steinke 2003). Furthermore, the innate immune system includes activation of the complement cascade and activation of the adaptive immune system through antigen presentation.

To analyze whether autopenetrated YopM is also able to interfere with the innate immune response, the transcription of several cytokines like tumor necrosis factor alpha (TNFα) *, interleukin 15 (IL-15)* or interferon γ (IFNγ)* as pro-inflammatory cytokines, was measured after treatment of cells with recombinant YopM.

* TNF represents two homologous proteins primarily derived from mononuclear phagocytes (TNFα) and lymphocytes (TNFβ). In addition to mononuclear phagocytes, TNFα may be produced by neutrophils, activated lymphocytes, NK cells, endothelial cells, mast cells, and cells of the intestinal epithelium. TNFα is a potent activator of neutrophils, induces chemotaxis of granulocytes to inflammatory loci and activates the respiratory burst. It also influences the adherence of endothelial cells (Beutler and Cerami, 1989; Perez et al., 1990; Tartaglia and Goeddel, 1992).

* IL-15 is a T-cell growth factor that is chemotactic for T lymphoctes and stimulates B-cell growth and differentiation. Moreover, it is crucial for the maintenance and activation of circulating NK cells, as well as NK cell development in bone marrow (Kennedy et al., 2000; Prlic et al., 2003; Ranson et al., 2003; Waldmann and Tagaya, 1999). Mononuclear phagocytic cells, epithelium, fibroblasts and placenta are the main sources of IL-15.

* IFNγ is the most important cytokine responsible for induction of cell-mediated immunity. It is primarily produced by T-helper lymphocytes, cytotoxic T-cells, and NK cells, but also other cell types have the capacity to synthesize IFNγ. Circulating IFNγ stimulates antigen presentation, monocyte effector functions and also cytokine production by monocytes (Borish and Steinke 2003).

For this purpose, HL60 cells were lysed after treatment with YopM for 3, 6 and 18 h, total RNA was extracted, measured, reverse transcribed and analyzed for the effect of YopM on transcription of TNFα and IL-15 by quantitative RT-PCR using specific primers for these cytokines (FIGS. 7A and B). After 3 h incubation, transcription of TNFα was only slightly decreased. However, mRNA amounts strongly decreased in the course of incubation (until 18 h; FIG. 7A). A similar pattern was seen for IL-15 mRNA in HL60 cells. The transcription of this cytokine was also strongly reduced during the time course, resulting in a plateau of reduction after 18 h of approximately 80% after YopM treatment, in relation to cells incubated with medium (control; FIG. 7B).

Further analyses of TNFα transcription after treatment of cells with proteins YopM$_{87-C}$ and YopE used as controls showed that these two proteins were not able to reduce transcription of TNFα. Moreover, incubation with both proteins, which are not able to penetrate membranes (2.2), resulted in an increased level of mRNA for TNFα in HL60 cells (FIG. 8A).

Because the increase of mRNA for TNFα was also detectable during mock incubation [mock: fractions of protein isolations, derived after induction of the overexpression vector pET24b(+) in *E. coli*], this effect might due to residual lipopolysaccharides (LPS) from protein expression and isolation from *E. coli*. Although the recombinant YopM used in our studies might still include residual LPS, YopM appears to counteract even this possible stimulatory effect of LPS on TNFα induction. This conclusion could already be confirmed by analyzing the TNFα transcription after co-incubation of HL60 cells with recombinant YopM and LPS derived from *E. coli* 0111:B4 (data not shown).

Further experiments revealed that YopM is able to down-regulate gene transcription at protein concentrations of 5 μg/ml. TNFα transcription is further down-regulated with increasing YopM concentrations up to 25 μg/ml. Higher YopM concentrations do not have further impact on TNFα transcription (FIG. 8 B).

Considering, that cells of the immune system are not the only source of cytokine synthesis, the transcription of TNFα, IL-15 and IFNγ was also analyzed after treatment of HeLa cells with recombinant YopM.

While treatment of HeLa cells with YopE as a control again showed slightly increased levels of mRNA for TNFα, IL-15 as well as for IFNγ, incubation with recombinant YopM lead to substantially reduced levels of mRNA in all cases (FIG. 9A, B, C). In contrast to cells incubated with YopE, the mRNA levels of TNFα and IFNγ were drastically reduced after treatment of YopM for 6 h. The mRNA levels for IL-15 were only slightly decreased. In summary, these results show that the effect of YopM on transcription of cytokines is not only limited to cells of the immune system and suggests that YopM can also act on other (ubiquitous) activator cells of the innate immune system.

EXAMPLE 5

Gene Array Analysis

Although autopenetrated YopM has the ability to down-regulate pro-inflammatory cytokines like TNFα, IL-15 or IFNγ, the total influence of YopM on gene transcription cannot be determined by an experiment based on TNFα, IL-15 or IFNγ, alone. To increase the knowledge about the transcriptional influence of YopM on additional cytokines as well as its influence on other so far unknown genes, a gene array analysis was performed. This technique allows the investigation of transcriptional changes of 40.000 genes in a single experiment.

Raw data of transcriptional changes in differentiated HL60 cells after incubation with recombinant YopM or YopM$_{87-C}$, and medium as a control, were analyzed with the ArrayAssist® software (Stratagene) and scanned for genes which are down or up-regulated after YopM treatment, and in addition are not differentially transcribed after incubation with YopM$_{87-C}$. This significance analysis ensured the filtering for effects caused by auto-penetrating YopM and not by other site effects of the treatment, like a putative LPS-contamination in isolated protein fractions. These analyses confirmed the down-regulation of transcription for TNFα and IL-15 and further identified the cytokines IFNα, IL-10, IL-8, IL-16 and IL-22 to be also transcriptionally down-regulated by YopM. Furthermore, the transcription of several receptors for cytokines such as the receptors for TNF, IL-6, IL-12β, IL-15 and IL-20 was found to be also down-regulated. Interestingly, genes that respond to the mentioned cytokines like TNFα-induced proteins or IFN-induced proteins as downstream targets of certain cytokines were also down-regulated.

Beside genes for cytokines, several other genes encoding transcription factors (zinc finger proteins), different kinases and apoptosis-inducing factors, showed a down-regulation of transcription. These genes are involved in central signalling pathways, such as MAPK signalling, G-protein signalling, JAK-STAT signalling, and apoptosis signalling, as well as in cell cycle control and cell growth. McDonald et al. (2003) described that YopM forms complexes with specific serine/threonine kinases, which may interact with a number of immunological signalling pathways as well as with cell cycle and cell growth. This model could offer a possible explanation for the results observed.

EXAMPLE 6

Human Inflammation Antibody Array

In order to assess translational changes and, moreover, alterations in the secretion of cytokines by YopM, a RayBio® Human Inflammation Antibody Array was used. For this purpose, differentiated HL60 cells were incubated for 6 h with recombinant YopM, YopM$_{87-C}$, or medium. Subsequently, the supernatants of incubated cells were analyzed for the amount of certain pro-inflammatory cytokines FIG. 10 shows the effect of YopM and YopM$_{87-C}$ on the secretion of pro-inflammatory cytokines in HL60 cells. Obviously, the incubation of HL60 cells with recombinant YopM reduced the secretion of certain cytokines, while incubation with the non-penetrating construct YopM$_{87-C}$ did not reduce the secretion. In fact, treatment with YopM$_{87-C}$ actually induced the pro-inflammatory response of the HL60 cells.

The reduction in secretion of the pro-inflammatory cytokines TNFα, IFNγ, IL-1β, IL-8 and IL-16 as well as of specific receptors for these cytokines after YopM treatment, confirm the data of quantitative Real Time RT-PCR and gene array analyses and indicate a drastic reduction of mediators of the innate immune response.

Also chemokines like I-309 or IP-10 were less secreted after YopM treatment. The effect of YopM on cytokines, chemokines and other factors could either be a direct effect of the protein, or a side effect resulting from an interference with specific signalling cascades by YopM.

EXAMPLE 7

Characterization of YopM Domains Necessary for Immunomodulation

To analyze and localize domains within YopM that mediate immunomodulation, the truncated versions of YopM previously described (see Example 2), were used to treat differentiated HL60 cells. Besides the control protein YopM$_{87-C}$, only those versions of YopM were used, that are all still able to penetrate host cell membranes (see Example 2), because we presumed that the autopenetration ability is required for immunomodulation.

While the control protein YopM$_{87-C}$, which does not autopenetrate cells, was not able to reduce transcription of TNFα, the autopenetrating versions, YopM$_{N-239}$, and YopM$_{55-C}$, were still able to reduce transcription of the TNFα (see FIG. 11). These results exclude a role of the C-terminus and the first amino-terminal helix of YopM in immunomodulation.

The fact that the fusion protein 2αH-GFP containing both α-helices of YopM, was no longer able to reduce transcription of TNFα (FIG. 11) indicates that the LRRs 1-8 of YopM harbour the potential immunomodulatory domain. Furthermore, this result excludes a role of the amino-terminal α-helices of YopM in immunomodulation.

EXAMPLE 8

Influence of YopM on the Expression of Interleukins in Human Intestinal Microvascular Endothelial Cells (HIMEC) as an In Vitro Model for IBD Inflammatory bowel diseases (IBD) are characterized by an overreactive immune system attacking various tissues of the digestive tract. The major types of IBD are Crohn's disease (CD) and ulcerative colitis (UC). While CD can affect any part of the gastrointestinal tract, UC is restricted to the colon and the rectum. Elevated levels of proinflammatory cytokines and in particular IL-12-related molecules are involved in cell-mediated immune responses as well as IBD (Larousserie, F., Pflanz, S., Coulomb-L'Herminé, A., Brousse, N., Kastelein, R., Devergne, O. *J. Pathol.* 202:164-171 (2004)). Recent work has suggested that human intestinal microvascular endothelial cells (HIMEC) are actively involved in the pathogenesis of IBD (Hatoum, O. A. and Binion, D. G. *Inflamm. Bowel Dis.* 11: 304-313 (2005)). The expression of proinflammatory cytokines and IL-12-related molecules in HIMEC can be induced by the TLR3 agonist poly(I:C) (Heidemann, J., Rüther, C., Kebschull, M., Domschke, W., Brüwer, M., Koch, S., Kucharzik, T., Maaser, C. *Am. J. Physiol. Gastrointest. Liver Physiol.* 293:G1315-1324 (2007)). Therefore, poly(I:C)-stimulated HIMECs represent an in vitro model for IBD in which the influence of YopM on mediators of human IBD can be investigated.

In an initial approach, we determined the ability of YopM to autopenetrate HIMEC. After incubation of HIMECs with recombinant YopM or the non-penetrating derivative YopM$_{87-C}$ for 1 h, the cells were prepared for immunofluorescence microscopy as described above (Example 1). YopM was visualized with polyclonal YopM antiserum and a Cy2-labelled secondary antibody. DNA was stained DAPI.

Immunofluorescence images revealed that HIMECs incubated with recombinant YopM show localization of the protein inside the cytoplasm (FIG. 14; a-c). Moreover, YopM is distributed all over the cytoplasm and accumulates in the perinuclear region as observed previously (Example 1). Internalization of the non-penetrating derivative YopM$_{87-C}$ was not detectable (FIG. 14; d-f). After we determined that YopM can indeed autopenetrate these primary cells, we investigated the influence on expression of proinflammatory cytokines, IL-12-related molecules, and endothelial cell adhesion molecules after stimulation of HIMECs with poly(I:C). To this end, HIMECs were pre-incubated with YopM for 3 h and subsequently stimulated for an additional 16 h with poly(I:C) (100 μg/ml). Total RNA was extracted, reverse transcribed, and analysed for the preventive effect of YopM on poly(I:C)-induced transcription of TNFα, IL-β, IL12p35, IL23p19, EBI3, ICAM-1, and VCAM-1 by quantitative RT-PCR (FIG. 13). As described by Heidemann et al., the stimulation of HIMECs with poly(I:C) resulted in strongly induced levels of the proinflammatory cytokines TNFα (26.5×) and IL-1β (17.95×) compared to untreated cells (FIG. 13). Additionally, transcriptional upregulation of genes coding for IL-12p35 (6.75×), IL-23p19 (2.36×), and Epstein-Barr virus-induced gene 3 (EBI3, 132×) was observed (FIG. 13). The EBI3 protein is structurally related to the IL-12 p40 subunit. After association with p28 both subunits constitute IL-27, which has been demonstrated to possess complex pro- and anti-inflammatory functions (Villarino, A. V., Huang, E., Hunter, C. A. *J Immunol* 173:715-720 (2004)). Besides poly(I:C)'s function as an inducer of proinflammatory cytokines and IL-12-related molecules in HIMEC, the TLR3 agonist also affects the regulation of the adhesion molecules ICAM-1 and VCAM-1 (FIG. 13), which are indicators of proinflammatory cell activation.

The incubation of poly(I:C)-treated HIMECs with YopM for 3 h resulted in a strong decrease in the effects of poly(I:C) on transcription of the investigated genes (FIG. 13). In particular, YopM pre-incubation inhibited poly(I:C) induction of TNFα (88%), IL-1β (86%), IL-12p35 (61%), IL-23p19 (29%), EBI3 (62%), ICAM-1 (65%), and VCAM-1 (95%) transcription. Our data show that—in addition to already described cell types—YopM has the ability to enter also human intestinal microvascular endothelial cells and that it can prevent the induction of mediators of inflammation in this in vitro model for human IBD.

EXAMPLE 9

Cell-Penetrated YopM Inhibits the Production of Rheumatoid Arthritis (RA)-Relevant Molecules in Human Synovial Fibroblasts Rheumatoid arthritis (RA) is a chronic, systemic autoimmune disorder that most commonly causes inflammation and tissue damage in joints (arthritis). The arthritis of RA is due to synovitis, which is an inflammation of the synovial membrane that lines joints and tendon sheaths. RA synovial fibroblasts (RASFs) together with synovial macrophages are active drivers of joint destruction in RA. In this destructive process, RASFs actively cause inflammation and degradation of the joint by producing inflammatory cytokines and matrix-degrading molecules (Müller-Ladner, U., Ospelt, C., Gay, S., Distler, O., Pap, T. *Arthritis Res Ther* 9:223-233 (2007)).

Due to the active involvement of RASFs in RA development, we investigated the interaction of recombinant YopM with this cell type. For this purpose, YopM was isolated and purified via Ni-NTA affinity chromatography, dialyzed against PBS and conjugated to the reactive fluorescent Cy3-dye as described in the manufacturer's instructions (Cy3-

DyeLight Ab labeling Kit; GE Healthcare). RASFs were incubated with YopM-Cy3 for 30 min and 1 h, respectively. After incubation, the cells were prepared for fluorescence microscopy. DNA was stained with Draq5 and the cells were analyzed by confocal laser scanning microscopy.

After 30 min of incubation with YopM-Cy3, the protein appeared in vesicle-like structures inside the cytoplasm of RASFs (FIG. 14; a-c), indicating that YopM also autopenetrates this cell type. After prolonged incubation for 1 h, the amount of YopM inside the cytoplasm of incubated RASFs increased, and the characteristic accumulation of YopM in perinuclear regions of the cells was observed (FIG. 14; d-f). After we confirmed the ability of YopM to penetrate RASFs, we were interested whether YopM might have an effect on inflammation and cartilage destruction. In this context, the secretion of IL-6 by RASFs induces acute phase reactions and inflammation in the synovium. The cartilage destruction observed in RA is caused by secretion and activation of matrix metalloproteinases (MMPs). MMP-1 and MMP-3 are the major enzymes produced by RASFs. MMP-1 degrades fibrillar collagens (collagens I, II, VII and X), whereas MMP-3 degrades a broad array of extracellular matrix substrates (Noh, E. M., Kim, J. S., Hur, H., Park, B. H., Song, E. K., Han, M. K., Kwon, K B., Yoo, W. H., Shim, I. K., Lee, S. J., Youn, H. J., Lee, Y. R. *Rheumatology* 48: 5-48 (2009)).

In order to analyze YopM's influence on secretion of IL-6, MMP-1 and MMP-3, RASFs were co-incubated with TNFα (10 ng/ml) and recombinant YopM for different time points. Subsequently, the production of IL-6, MMP-1 and MMP-3 in the culture supernatants of RASFs was determined by ELISA (FIG. 15 A-C; medium, TNFα and YopM). After incubation of RASFs with TNFα, the production of IL-6 is induced (at least 3-fold), while incubation with YopM resulted in a reduced IL-6 production compared to control cells (about 12-fold as compared to incubation with medium alone, FIG. 15 A). Co-incubation of RASFs with TNFα and YopM revealed a drastic inhibition of TNFα-induced IL-6 production. This effect persisted for 8 h of incubation with recombinant YopM (FIGS. 15 A; 6 h and 8 h). The production of MMP-1 and MMP-3 is also drastically reduced. Incubation of RASFs with YopM alone, as well as co-incubation with TNFα and YopM for 6 h and 8 h resulted in strongly reduced amounts of these cartilage-destroying molecules. Taken together, these results demonstrate that recombinant YopM can penetrate cells involved in the development of RA and has an inhibitory effect on the production of inflammatory and cartilage-destroying molecules. This underlines our claim that recombinant YopM can be beneficially applied in the treatment of autoimmune diseases such as RA.

EXAMPLE 10

Effect of YopM on RANKL-Induced Osteoclastogenesis of Mouse Bone Marrow Cells

In addition to controlling inflammation, prevention of structural damage is a key objective of anti-rheumatic therapy. One hallmark of RA is local bone erosion, which involves destruction of juxta-articular bone. This structural damage is based on formation of osteoclasts in and around the joint, which resorb mineralized cartilage and subchondral bone. The osteoclast are an integral part of the mixed cellular infiltrate of inflammatory arthritis and accumulation of these cells at sites of structural damage suggest that molecules involved in osteoclast formation are important players in the destructive processes of the disease (Schett, G. *Arthritis Res. Ther.* 9 Suppl 1:S2 (2007)). In this context, the Receptor Activator for Nuclear Factor κB Ligand (RANKL) and Macrophage Colony Stimulating Factor (M-CSF) are essential for the differentiation of osteoclasts from their precursor cells, and a lack of either molecule is sufficient to block osteoclast formation completely (Yoshida, H., Hayashi, S., Kunisada, T., Ogawa, M., Nishikawa, S., Okamura, H., Sudo, T., Shultz, L. D., Nishikawa, S. *Nature* 345: 442-444 (1990)).

In order to test a possible influence of YopM on osteoclastogenesis, bone marrow cells of adult mice of 8-12 weeks of age were isolated from the cut shafts of mouse femurs and tibias by fluid pressure applied by a syringe. Cultures were maintained in 200 µl α-MEM (supplemented with antibiotics and 10% FCS) for 5 days, with a change of medium every 2-3 days. Incubation of the cultures with soluble recombinant RANKL (50 ng/ml) and M-CSF (30 ng/ml) induces the development and fusion of tartrate-resistant acid phosphatase positive (TRAP$^+$) osteoclasts at 3-5 days (Gardner, C. R., *Cell Tissue Res.* 330:111-121 (2007)). Mouse bone marrow cells induced by RANKL and M-CSF were incubated with YopM (10 ng/ml) for 5 days, while control cells were incubated with RANKL/M-CSF only. Subsequently, cells were prepared for microscopy. TRAP$^+$-cells were stained with 200 µl of solution containing Fast Garnett (leukocyte acid phosphatase kit, Sigma Diagnostics) in the presence of tartrate, for 30 min at 37° C.

Examination of cells by light microscopy (10× and 43× magnification) revealed that control cells stimulated with M-CSF for 5 days did not show any formation of multinuclear (pre-)-osteoclasts, while co-stimulation with M-CSF and RANKL induced the development and fusion of TRAP$^+$ osteoclasts (FIG. 16A). In comparison, co-incubation with YopM in addition to stimulation with the two mediators of osteoclastogenesis lead to strong inhibition of osteoclastogenesis of bone marrow cells (FIG. 16, A). Of the YopM co-incubated cells, only few developed to small intermediate cells (2-10 nuclei), as also observed in control cells stimulated with M-CSF (FIG. 16, A). Furthermore, the quantification of TRAP$^+$-multinuclear osteoclasts by light microscopy revealed that M-CSF and RANKL stimulation induces development of TRAP$^+$ (pre-) osteoclast (2-10 nuclei) and also fusion of these cells to larger multinuclear osteoclasts (>10 nuclei; FIG. 16 B). As already shown by light microscopy, this effect was completely inhibited by co-incubation of YopM (FIG. 16B).

Taken together, our results indicate that YopM is able to reduce the production of inflammatory mediators relevant in RA (Example 9), and is capable of preventing structural damage by inhibition of osteoclastogenesis. Both of these YopM effects might be beneficial in an antirheumatic therapy against inflammation and structural damage.

EXAMPLE 11

Intra-particular Application of YopM-Cy3 into Synovial Joints of Mice

Concerning a potential in vivo delivery of cargos by the two N-terminal helices of YopM (2αH) as well as using the immunomodulatory ability of YopM to treat autoimmune diseases, particularly TNF-linked diseases such as e.g. rheumatoid arthritis (RA), we investigated the distribution of Cy5-conjugated YopM after intra-articular (i.a.) injection into the joints of the hind leg of a anaesthesized hairless mouse by Fluorescence Reflection Imaging (FR1). Recombinant YopM was isolated and purified via Ni-NTA chromatography, dialysed against PBS and conjugated to the reactive fluorescent Cy5 dye as described by the manufacturers instructions (Cy5-

DyeLight Ab labelling Kit; GE Healthcare). After i.a. injection into the joints of the hind leg of a mouse, YopM-Cy5 cell remained at the site of injection and did not disseminate systemically during a 72 h time period. The YopM-Cy5 signal disappeared over time, which is most probably due to degradation of the dye and/or the whole compound. This initial result indicates the feasibility of a focussed application of YopM into skeletal joints, further strengthening the potential of YopM as a novel therapeutic agent for the treatment of RA and other inflammatory diseases.

EXAMPLE 12

YopM's Intracellular Localization

In order to determine YopM's intracellular localization, electron microscopy (EM) with gold-labelled YopM was done (FIG. 18). Early after incubation of HeLa cells (5-15 min at 37° C.), YopM-Au was detected bound to the cell surface (FIG. 18; a) and also appeared to be associated with vesicles in the cytosol (FIG. 18; b). Later after incubation (15-60 min), YopM-Au can be found in multi-vesicular bodies (MVB; FIG. 18; c), which are a typical form of late endosomes (LE). Interestingly, we often observed YopM-associated structures without any distinct membrane (FIG. 18; d). Moreover the vesicle membranes seemed to be dissolved, allowing YopM to escape from the endosomal compartment. Finally, YopM-Au was detected (3 h) free in the cytosol, as well as inside the nucleoplasma (FIG. 18; f, indicated by black arrows). This indicates, that YopM initially enters host cells via a vesicle-associated mechanism before entering the cytoplasm at later time points, a process we termed autopenetration. After autopenetration, YopM appears free in the cytosol, accumulates in perinuclear regions and can enter the nucleus.

The invention claimed is:

1. A method for delivering at least one cargo molecule to cytosol of a cell, the method comprising a step of
contacting a eukaryotic cell with a composition comprising
(a) an isolated *Yersinia* outer protein M (YopM) or an isolated YopM fragment comprising at least one alpha helix of YopM capable of mediating autopenetration, independent of *Yersinia* type III secretion system (T3SS), and
(b) at least one cargo molecule,
wherein said at least one cargo molecule is delivered across a membrane to the cytosol of said cell, and wherein said YopM or YopM fragment independent of T3SS, autopenetrates the cell membrane and integrates into the cell cytosol of the eukaryotic cell.

2. The method of claim 1, wherein the YopM or fragment thereof is a YopM sequence of a YopM-encoding virulence plasmid of a naturally-occurring *Yersinia* strain.

3. The method of claim 1, wherein the YopM or fragment thereof is selected from YopM of the species *Yersinia enterocolitica*, *Yersinia pseudotuberculosis* or *Yersinia pestis*.

4. The method of claim 1, wherein the YopM comprises the amino acid sequence of any sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8.

5. The method of claim 1, wherein said cargo molecule comprises at least one compound selected from the group consisting of nucleic acids, polypeptides, organic molecules, small organic molecules, metals, nano-particles, viruses, modified viruses, viral vectors, antibodies and/or plasmids.

6. The method of claim 1, wherein said cargo displays therapeutical and/or diagnostic activity.

7. The method of claim 1, wherein said YopM or said YopM fragment is additionally linked to a cell-specific targeting agent.

8. The method of claim 1, wherein said YopM or said YopM fragment has essentially no immunomodulatory capability.

9. A pharmaceutical composition comprising isolated YopM or an isolated YopM fragment comprising at least one alpha helix of YopM, wherein said YopM or YopM fragment is independent of *Yersinia* type III secretion system (T3SS) and capable of autopenetrating the cell membrane and of integrating into the cell cytosol, and wherein said YopM or YopM fragment is linked to a cargo.

10. The method of claim 1 wherein the composition is in the form of a pharmaceutical composition and the step of contacting comprises administering the composition to a patient, wherein said method causes the downregulation of cytokines and/or cytokine receptors and/or genes which respond to cytokines and/or cartilage-destroying molecules and/or inhibiting osteoclastogenesis in the patient.

11. The method of claim 1 wherein the composition is in the form of a pharmaceutical composition and the step of contacting comprises administering the composition to a patient, wherein said method regulates inflammatory reactions of the immune system, treats diseases caused by autoimmunity of the patient, treats inflammation, chronic inflammation, gastroenteritis, chronic gastritis, inflammatory bowel diseases (IBD), Colitis ulcerosa, psoriasis, allergic reactions, Morbus Crohn, rheumatoid arthritis treats bone diseases characterized by changes in bone resorption, and/or suppresses the immune system.

12. A YopM fragment essentially comprising one of the alpha helices of YopM, two of the alpha helices of YopM, one of the alpha helices of YopM and 1 to 3 YopM leucine-rich repeats or two of the alpha helices of YopM and 1 to 3 YopM leucine-rich repeats, wherein said YopM fragment is independent of *Yersinia* type III secretion system (T3SS) and capable of autopenetrating the cell membrane and of integrating into the cell cytosol, wherein said YopM fragment is linked to at least one cargo molecule.

13. The method of claim 4, wherein YopM comprises SEQ ID NO: 4.

14. The pharmaceutical composition of claim 9, wherein said YopM or fragment comprises at least one leucine-rich repeat.

15. The method of claim 1 wherein the YopM fragment comprises amino acids 1-51 of SEQ ID NO: 4.

16. The method of claim 1 wherein the YopM fragment comprises amino acids 52-73 of SEQ ID NO: 4.

* * * * *